(12) United States Patent
Zanders et al.

(10) Patent No.: US 12,084,666 B2
(45) Date of Patent: Sep. 10, 2024

(54) COMPOSITIONS AND METHODS OF DUAL POISON-ANTIDOTE MEIOTIC DRIVERS

(71) Applicants: STOWERS INSTITUTE FOR MEDICAL RESEARCH, Kansas City, KS (US); FRED HUTCHINSON CANCER CENTER, Seattle, WA (US)

(72) Inventors: Sarah E. Zanders, Prairie Village, KS (US); Nicole Nuckolls, Shawnee, KS (US); Maria Angelical Bravo Nunez, Kansas City, KS (US); Harmit Singh Malik, Shoreline, WA (US)

(73) Assignees: STOWERS INSTITUTE FOR MEDICAL RESEARCH, Kansas City, MO (US); FRED HUTCHINSON CANCER CENTER, Seattle, WA (US)

( * ) Notice: Subject to any disclaimer, the term of this patent is extended or adjusted under 35 U.S.C. 154(b) by 1279 days.

(21) Appl. No.: 16/608,146

(22) PCT Filed: Apr. 27, 2018

(86) PCT No.: PCT/US2018/029997
§ 371 (c)(1),
(2) Date: Oct. 24, 2019

(87) PCT Pub. No.: WO2018/201073
PCT Pub. Date: Nov. 1, 2018

(65) Prior Publication Data
US 2020/0149054 A1 May 14, 2020

Related U.S. Application Data

(60) Provisional application No. 62/491,107, filed on Apr. 27, 2017.

(51) Int. Cl.
| | | |
|---|---|---|
| *C12N 15/81* | (2006.01) | |
| *C07K 14/39* | (2006.01) | |
| *C12N 1/00* | (2006.01) | |

(52) U.S. Cl.
CPC ............ *C12N 15/815* (2013.01); *C07K 14/39* (2013.01); *C12N 1/00* (2013.01); *C12N 2800/00* (2013.01); *C12N 2840/007* (2013.01)

(58) Field of Classification Search
CPC .... C12N 15/815; C12N 1/00; C12N 2800/00; C12N 2840/007; C07K 14/39
See application file for complete search history.

(56) References Cited

U.S. PATENT DOCUMENTS

2016/0044902 A1 2/2016 Alphey et al.

OTHER PUBLICATIONS

Hammond et al. 2012 PNAS IMolecular dissection of Neurospora Spore killer meiotic drive elements. I vol. 109 I No. 30 I 12093-12098 (Year: 2012).*
Zanders Supplemental File 1 [online] Jun. 24, 2014 [retrieved on Apr. 25, 2023] retrieved from https://elifesciences.org/articles/02630/figures#SD1-data (Year: 2014).*
UniProt A0A218N034 [online] [retrieved on Apr. 26, 2023] retrieved from https://www.uniprot.org/uniprotkb/A0A218N034/entry (Year: 2023).*
M.E. Thoma et al., Prevalence of infertility in the United States as estimated by the current duration approach and a traditional constructed approach. Fertil Steril 99, 1324-31 e1321 (2013).
L. Segurel, E.M. Leffler, M. Przeworski, The case of the fickle fingers: how the PRDM9 zinc finger protein specifies meiotic recombination hotspots in humans. PLoS Biol 9, e1001211 (2011).
D.C. Presgraves, The molecular evolutionary basis of species formation. Nat Rev Genet 11, 175-80 (2010).
N.A. Johnson, Hybrid incompatibility genes: remnants of a genomic battlefield? Trends Genet 26, 317-25 (2010).
A.K. Lindholm et al., The Ecology and Evolutionary Dynamics of Meiotic Drive. Trends Ecol Evol 31, 315-26 (2016).
L. Sandler, E. Novitski, Meiotic Drive as an Evolutionary Force. The American Naturalist 91, 105-110 (1957).
J.F. Crow, Why is Mendelian segregation so exact? Bioessays 31, 305-12 (1991).
J.P. Didion et al., A multi-megabase copy number gain causes maternal transmission ratio distortion on mouse chromosome 2. PLoS Genet 11, e1004850 (2015).
C S Ottolini et al, Genome-wide maps of recombination and chromosome segregation in human oocytes and embryos show selection for maternal recombination rates. Nat Genet 47, 727-35 (2015).
Grognet et al., Genes that bias Mendelian segregation. PLoS Genet 10, e1004387 (2014).
A. Burt, R. Trivers, Genes in conflict : the biology of selfish genetic elements. (Belknap Press of Harvard University Press, Cambridge, Mass., 2006), pp. viii, 602 p., 608 p. of plates.
A. M. Larracuente, D. C. Presgraves, The selfish Segregation Distorter gene complex of Drosophila melanogaster. Genetics 192, 33-53 (2012).
H. Bauer et al., The nucleoside diphosphate kinase gene Nme3 acts as quantitative trait locus promoting non-Mendelian inheritance. PLoS Genet 8, e1002567 (2012).
H. Bauer, N. Veron, J. Willert, B. G. Herrmann, The t-complex-encoded guanine nucleotide exchange factor Fgd2 reveals that two opposing signaling pathways promote transmission ratio distortion in the mouse. Genes Dev 21, 143-147 (2007).
H. Bauer, J. Willert, B. Koschorz, B. G. Herrmann, The t complex-encoded GTPase-activating protein Tagap1 acts as a transmission ratio distorter in mice. Nat Genet 37, 969-973 (2005).

(Continued)

*Primary Examiner* — Celine X Qian
*Assistant Examiner* — Tiffany Nicole Grooms
(74) *Attorney, Agent, or Firm* — Bryan Cave Leighton Paisner LLP

(57) ABSTRACT

The present disclosure provides, inter alia, meiotic drive genes derived from chromosome 3 of the fission yeasts *Schizosaccharomyces kambucha* and *S. pombe* and orthologs thereof. In certain embodiments, compositions, methods, and kits are provided for biasing organisms to express such genes and, optionally, to co-express one or more genes of interest in such organisms.

6 Claims, 23 Drawing Sheets
(20 of 23 Drawing Sheet(s) Filed in Color)
Specification includes a Sequence Listing.

(56) References Cited

OTHER PUBLICATIONS

T. M. Hammond, D. G. Rehard, H. Xiao, P. K. Shiu, Molecular dissection of Neurospora Spore killer meiotic drive elements. Proc Natl Acad Sci U S A 109, 12093-12098 (2012).
N. Rhind et al., Comparative functional genomics of the fission yeasts. Science 332, 930-936 (2011).
S. E. Zanders et al., Genome rearrangements and pervasive meiotic drive cause hybrid infertility in fission yeast. Elife 3, e02630 (2014).
A. T. Avelar, L. Perfeito, I. Gordo, M. G. Ferreira, Genome architecture is a selectable trait that can be maintained by antagonistic pleiotropy. Nat Commun 4, 2235 (2013).
N. Phadnis, R. W. Hyppa, G. R. Smith, New and old ways to control meiotic recombination. Trends Genet 27, 411-421 (2011).
K. Bomblies, Cheaters divide and conquer. Elife 3, e03371 (2014).
A. Moore, C. J. Donahue, K. D. Bauer, J. P. Mather, Simultaneous measurement of cell cycle and apoptotic cell death. Methods Cell Biol 57, 265-278 (1998).
N. J. Bowen, I. K. Jordan, J. A. Epstein, V. Wood, H. L. Levin, Retrotransposons and their recognition of pol II promoters: a comprehensive survey of the transposable elements from the complete genome sequence of Schizosaccharomyces pombe. Genome Res 13, 1984-1997 (2003).
J. Mata, R. Lyne, G. Burns, J. Bahler, The transcriptional program of meiosis and sporulation in fission yeast. Nat Genet 32, 143-147 (2002).
M. D. Daugherty, H. S. Malik, Rules of engagement: molecular insights from host-virus arms races. Annu Rev Genet 46, 677-700 (2012).
R. N. McLaughlin, Jr., H. S. Malik, Genetic conflicts: the usual suspects and beyond. J Exp Biol 220, 6-17 (2017).
C. I. Wu, T. W. Lyttle, M. L. Wu, G. F. Lin, Association between a satellite DNA sequence and the Responder of Segregation Distorter in *D. melanogaster*. Cell 54, 179-189 (1988).
A. M. Harvey et al., A critical component of meiotic drive in Neurospora is located near a chromosome rearrangement. Genetics 197, 1165-1174 (2014).
Z. Kuang, J. D. Boeke, S. Canzar, The dynamic landscape of fission yeast meiosis alternative-splice isoforms. Genome Res (2016).
M. A. Sheff, K. S. Thorn, Optimized cassettes for fluorescent protein tagging in *Saccharomyces cerevisiae*. Yeast 21, 661-670 (2004).
D. W. Hailey, T. N. Davis, E. G. Muller, Fluorescence resonance energy transfer using color variants of green fluorescent protein. Methods Enzymol 351, 34-49 (2002).
G. R. Smith, Genetic analysis of meiotic recombination in Schizosaccharomyces pombe. Methods Mol Biol 557, 65-76 (2009).
S. Henikoff, K. Ahmad, H. S. Malik, The centromere paradox: stable inheritance with rapidly evolving DNA. Science 293, 1098-1102 (2001).
W. Hu et al., A large gene family in fission yeast encodes spore killers that subvert Mendel's law Submitted.
K.Y. Lee, B.J. Lee, Structure, Biology, and Therapeutic Application of Toxin-Antitoxin Systems in Pathogenic Bacteria. Toxins (Basel) 8, (2016).
S.J. Unterholzner, B. Poppenberger, W. Rozhon, Toxin-antitoxin systems: Biology, identification, and application. Mob Genet Elements 3, e26219 (2013).
X. Wang et al., A new type V toxin-antitoxin system where mRNA for toxin GhoT is cleaved by antitoxin GhoS. Nat Chem Biol 8, 855-61 (2012).
L. C. De Veaux, N. A. Hoagland, G. R. Smith, Seventeen complementation groups of mutations decreasing meiotic recombination in Schizosaccharomyces pombe. Genetics 130, 251-262 (1992).
A. L. Goldstein, J. H. McCusker, Three new dominant drug resistance cassettes for gene disruption in *Saccharomyces cerevisiae*. Yeast 15, 1541-1553 (1999).
A. Wach, A. Brachat, R. Pohlmann, P. Philippsen, New heterologous modules for classical or PCR-based gene disruptions in *Saccharomyces cerevisiae*. Yeast 10, 1793-1808 (1994).
T.D. Wu et al., GMAP and GSNAP for Genomic Sequence Alignment: Enhancements to Speed, Accuracy, and Functionality. Methods Mol Biol 1418, 283-334 (2016).
H. Thorvaldsdottir, J.T. Robinson, J.P. Mesirov, Integrative Genomics Viewer (IGV): high-performance genomics data visualization and exploration. Brief Bioinform 14, 178-92 (2013).
A. Krogh, B. Larsson, G. von Heijne, E. L. Sonnhammer, Predicting transmembrane protein topology with a hidden Markov model: application to complete genomes. J Mol Biol 305, 567-580 (2001).
J. Z. Jacobs, K. M. Ciccaglione, V. Tournier, M. Zaratiegui, Implementation of the CRISPR-Cas9 system in fission yeast. Nat Commun 5, 5344 (2014).
J.A. Young et al., Meiotic recombination remote from prominent DNA break sites in S. pombe. Mol Cell 9, 253-63 (2002).
Burt, R. Trivers, Genes in conflict : the biology of selfish genetic elements. (Belknap Press of Harvard University Press, Cambridge, Mass., 2006), pp. viii, 602 p., 608 p. of plates.
Moore, C. J. Donahue, K. D. Bauer, J. P. Mather, Simultaneous measurement of cell cycle and apoptotic cell death. Methods Cell Biol 57, 265-278 (1998).
Nuckolls, et al. "WTF Genes are Prolific Dual Poison-Antidote Meiotic Drivers," eLife, Jun. 20, 2017 vol. 8, No. e26033.
Hammond, et al. "Molecular Dissection of Neurospora Spore Killer Meiotic Drive Elements," Proc Natl. Acad Aci Jul. 2, 2012 vol. 109.
Kuang, et al. "The Dynamic Landscape of Fission Yeast Meiosis Alternative-Splice Isoforms," Genome Res. Nov. 17, 2016, vol. 27.
Lindholm, et al. "The Ecology and Evolutionary Dynamics of Meiotic Drive," Trends Ecol Evol. Feb. 23, 2016 vol. 31.
Zanders, et al. "Genome Rearrangements and Pervasive Meiotic Drive Cause Hybrid Infertility in Fission Yeast," eLift Jun. 24, 2014, vol. 3, No. e02630.
Lopez Hernandez, et al. "Veni, Vidi, Vici: the Success of WTF Meiotic Drivers in Fission Yeast," Yeast, Feb. 21, 2018, vol. 35.
International Search Report for PCT/US2018/029997 dated Aug. 24, 2018.

* cited by examiner

FIG. 1C

C  *rec12Δ* introgression diploid phenotypes

| (diploid #) | genotype | % Ade⁻ Hyg^R progeny | % allele 2 (excluding Ade⁻ Hyg^R) in progeny |
|---|---|---|---|
| (1) | allele 1 — ade6Δ::hph<br>allele 2 — ade6⁺ | 78.9* | 87.5 |
| (2) | allele 1 — ade6Δ::hph<br>allele 2 — ade6⁺ | 72.0* | 85.3* |
| (3) | allele 1 — ade6Δ::hph<br>allele 2 — ade6⁺ | 75.6* | 93.7* |
| (4) | allele 1 — ade6Δ::hph<br>allele 2 — ade6⁺ | 77.2* | 2.6* |
| (5) | allele 1 — ade6⁺<br>allele 2 — ade6Δ::hph | 79.5* | 8.6* |
| (6) | allele 1 — ade6⁺<br>allele 2 — ade6Δ::hph | 65.6* | 6.4* |
| (7) | allele 1 — ade6⁺<br>allele 2 — ade6Δ::hph | 53.2* | 27.5* |
| (8) | allele 1 — ade6⁺<br>allele 2 — ade6Δ::hph | 96.5* | 52.9 |
| (9) | allele 1 — ade6Δ::hph<br>allele 2 — ade6⁺ | 38.0 | 85.2* |
| (10) | allele 1 — ade6Δ::hph<br>allele 2 — ade6⁺ | 28.9 | 53.1 |

FIG. 1F

| Diploid # | Strain (SZY#) | Introgression | Left boundary | Right boundary |
|---|---|---|---|---|
| 1 | 565 | Left | 55,477 | 55,555 |
|   |   | Right | 236,991 | 237,572 |
| 2 | 566 |   | 243,529 | 252,650 |
| 3 | 564 |   | 1,060,764 | 1,150,476 |
| 4 | 562 | Left | 200,230 | 201,437 |
|   |   | Middle | 1,394,572 | 1,397,380 |
|   |   | Right | 1,804,477 | 1,810,659 |
| 5 | 581 | Left | 243,529 | 252,650 |
|   |   | Middle | 865,843 | 891,682 |
|   |   | Right | 1,804,477 | 1,810,659 |
| 6 | 589 | Left | 816,613 | 821,264 |
|   |   | Right | 1,804,477 | 1,810,659 |
| 7 | 591 | Left | 762,873 | 763,460 |
|   |   | Right | 1,804,477 | 1,810,659 |
| 8 | 582 |   | 1,804,477 | 1,810,659 |
| 9 | 679 | Left | 207,954 | 210,312 |
|   |   | Right | 236,991 | 237,572 |

FIG. 1G

| Diploid # | allele 1 SZY# | ade6 GENOTYPE | allele 2 SZY# | ade6 GENOTYPE | ade6 allele transmission Ade+ HygS | Ade- HygR | Ade+ HygR | # progeny assayed | % disomy % Ade+ HygR | p value for disomy | % allele 2 (excluding disomes) | p value for % allele 2 (excluding disomes) | # diploids assayed |
|---|---|---|---|---|---|---|---|---|---|---|---|---|---|
| 1 | 565 | ade6Δ::hphMX4 | 196 | ade6+ | 21 | 3 | 90 | 114 | 78.9 | 3.2E-08 | 87.5 | 0.12 | 2 |
| 2 | 566 | ade6Δ::hphMX4 | 196 | ade6+ | 122 | 21 | 368 | 511 | 72.0 | 1.2E-12 | 85.3 | 3.9E-03 | 9 |
| 3 | 564 | ade6Δ::hphMX4 | 196 | ade6+ | 74 | 5 | 245 | 324 | 75.6 | 3.9E-12 | 93.7 | 3.6E-03 | 6 |
| 4 | 582 | ade6Δ::hphMX4 | 196 | ade6+ | 1 | 38 | 132 | 171 | 77.2 | 1.1E-09 | 2.6 | 8.8E-07 | 3 |
| 5 | 581 | ade6+ | 296 | ade6Δ::hphMX4 | 32 | 3 | 136 | 171 | 79.5 | 2.8E-10 | 8.0 | 1.8E-04 | 3 |
| 6 | 589 | ade6+ | 296 | ade6Δ::hphMX4 | 102 | 7 | 208 | 317 | 65.6 | 8.3E-09 | 6.4 | 2.6E-11 | 8 |
| 7 | 591 | ade6+ | 296 | ade6Δ::hphMX4 | 58 | 22 | 91 | 171 | 53.2 | 4.4E-04 | 27.5 | 9.7E-03 | 3 |
| 8 | 582 | ade6+ | 296 | ade6Δ::hphMX4 | 8 | 9 | 470 | 487 | 96.5 | 2.2E-16 | 52.9 | 0.99 | 9 |
| 9 | 679 | ade6Δ::hphMX4 | 196 | ade6+ | 247 | 43 | 179 | 469 | 38.0 | 0.06 | 85.2 | 6.3E-04 | 9 |
| 10 | 208 | ade6Δ::hphMX4 | 196 | ade6+ | 129 | 114 | 99 | 342 | 28.9 | control | 53.1 | control | >2 |

FIG. 2A

| (diploid #) | genotype | | % allele 1 in progeny | % PI-excluding spores |
|---|---|---|---|---|
| (11) | allele 1 | *wtf4* ━━━◆━━━ | 86.6* | 80.6* |
|  | allele 2 | ━━━━◆━━━━ |  |  |
| (12) | allele 1 | *wtf4Δ* ━━━◆━━━ | 66.0* | 95.6 |
|  | allele 2 | ━━━━◆━━━━ |  |  |
| (13) | allele 1 | *wtf4* ━━━◆━━━ | 44.4 | 92.0 |
|  | allele 2 | *wtf4* ━━━◆━━━ |  |  |
| (14) | allele 1 | *wtf4* ━━━◆━━━ | 92.8* | 59.2* |
|  | allele 2 | *wtf4Δ* ━━━◆━━━ |  |  |
| (15) | allele 1 | *wtf4Δ* ━━━◆━━━ | 55.8 | 92.4 |
|  | allele 2 | *wtf4Δ* ━━━◆━━━ |  |  |
| (16) | allele 1 | vector ━━━◆━━━ | 51.3 | 96.4 |
|  | allele 2 | ━━━━◆━━━━ |  |  |
| (17) | allele 1 | *wtf4* ━━━◆━━━ | 95.9* | 54.3* |
|  | allele 2 | ━━━━◆━━━━ |  |  |
| (18) | allele 1 | *wtf4* ━━━◆━━━ | 49.8 | 96.9 |
|  | allele 2 | *wtf4* ━━━◆━━━ |  |  |
| (19) | allele 1 | *wtf28* ━━━◆━━━ | 89.8* | 56.8* |
|  | allele 2 | ━━━━◆━━━━ |  |  |

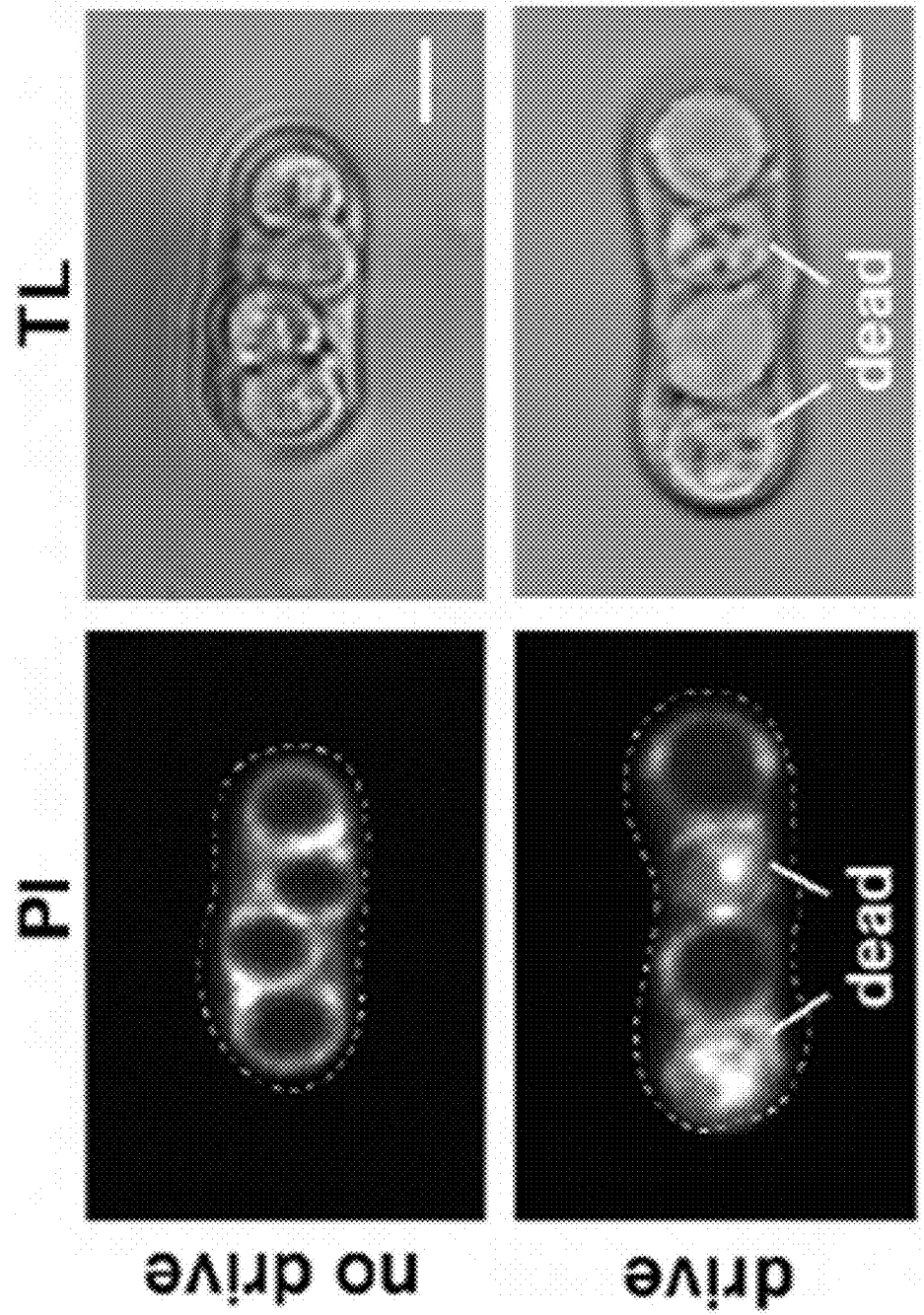

FIG. 2C

| Diploid # | allele 1 SZY# | ade6 GENOTYPE | allele 2 SZY# | ade6 GENOTYPE | % PI excluding cells | Viable Spore Yield |
|---|---|---|---|---|---|---|
| — | 643 | ade6+ | 44 | ade6+ | 98.58 | 1.7 ± 0.14 |
| 17 | 887 | ade6::Sk wtf4:kanMX4 | 44 | ade6+ | 54.25 | 1.0 ± 0.42 |
| 27 | 1049 | ade6::Sk wtf4<sup>smut</sup>-GFP:kanMX4 | 44 | ade6+ | 49.6 | 0.25 ± 0.057 |
| 22 | 1051 | ade6::Sk wtf4<sup>apmut</sup>::kanMX4 | 44 | ade6+ | 14.09 | 0.072 ± 0.0081 |

FIG. 4B

| (diploid #) | genotype | % allele 1 in progeny | % PI-excluding spores |
|---|---|---|---|
| (20) allele 1 / allele 2 | wtf4 antidote | 46.1 | 97.8 |
| (21) allele 1 / allele 2 | wtf4 / wtf4 antidote | 53.7 | 94.1 |
| (22) allele 1 / allele 2 | wtf4 poison | 37.7 * | 14.1 * |
| (23) allele 1 / allele 2 | wtf4 / wtf4 poison | 96.5 * | 56.9 * |
| (24) allele 1 / allele 2 | wtf4 antidote / wtf4 poison | 88.0 * | 44.6 * |

FIG. 5B

| (diploid #) | genotype | % allele 1 in progeny | % PI-excluding spores |
|---|---|---|---|
| (25) allele 1 / allele 2 | mCh----wtf4 / ———— | 89.7 * | -- |
| (26) allele 1 / allele 2 | wtf4 / mCh----wtf4 | 48.4 | -- |
| (27) allele 1 / allele 2 | wtf4----GFP / ———— | 56.0 | 49.6 * |
| (28) allele 1 / allele 2 | wtf4 / wtf4----GFP | 91.5 * | 55.0 * |

| Diploid # | allele 1 SZY# | allele 2 SZY# | ura4-wt#4 GENOTYPE | # PI-stained spores (dead) | # PI-excluding spores (alive) | % PI-excluding spores | # asci assayed | p-value | # diploids assayed |
|---|---|---|---|---|---|---|---|---|---|
| 11 | 861 | 702 | | 103 | 429 | 80.64 | 133 | 2.22E-16 | 2 |
| 12 | 863 | 703 | | 13 | 283 | 95.61 | 74 | 0.0194 | 2 |
| Diploid # | allele 1 SZY# | allele 2 SZY# | ura4-wt#4 GENOTYPE | | | | | | |
| 13 | 861 | 160 | | 22 | 262 | 92.25 | 71 | control | 3 |
| Diploid # | allele 1 SZY# | allele 2 SZY# | ura4-wt#4 GENOTYPE | | | | | | |
| 14 | 871 | 876 | | 111 | 146 | 56.8 | 68 | 2.22E-16 | 3 |
| 15 | 863 | 876 | | 26 | 289 | 92.4 | 83 | 0.964 | 3 |
| Diploid # | allele 1 SZY# | allele 2 SZY# | ade6 GENOTYPE | | | | | | |
| 16 | 825 | 44 | empty vector.kanMX4 | | | | | | |
| GFP clipout | 898 | 843 | | 29 | 771 | 96.38 | 200 | control | 2 |
| 17 | 897 | 44 | GFP.kanMX4 | 282 | 276 | 94.33 | 127 | 0.01989 | 2 |
| Diploid # | allele 1 SZY# | allele 2 SZY# | ade6 GENOTYPE | 352 | 416 | 54.23 | 192 | 2.22E-16 | 3 |
| 18 | 1064 | 867 | | ? | 212 | 96.88 | 86 | 0.6662 | 2 |
| Diploid # | allele 1 SZY# | allele 2 SZY# | ade6 GENOTYPE | | | | | | |
| 19 | 1033 | 44 | 5x wwd.kanMX4 | 143 | 188 | 56.79 | 83 | 2.22E-16 | 2 |
| 20 | 1033 | 44 | 5x wwd.kanMX4 | 96 | 696 | 87.63 | 225 | 0.01989 | 2 |
| 22 | 1051 | 44 | 5x wwd.kanMX4 | 244 | 40 | 14.09 | 71 | 2.22E-16 | 2 |
| Diploid # | allele 1 SZY# | allele 2 SZY# | ade6 GENOTYPE | | | | | | |
| 21 | 1084 | 1033 | 5x wwd.kanMX4 | 13 | 222 | 94.18 | 59 | 9.09 | 3 |
| 23 | 1084 | 1051 | | 61 | 116 | 56.58 | 51 | 2.22E-16 | 2 |
| Diploid # | allele 1 SZY# | allele 2 SZY# | ade6 GENOTYPE | | | | | | |
| 24 | 1110 | 1051 | 5x wwd.kanMX4 | 122 | 100 | 44.95 | 97 | 2.22E-16 | 3 |
| Diploid # | allele 1 SZY# | allele 2 SZY# | ade6 GENOTYPE | | | | | | |
| 25 | 1085 | 44 | mn2b.kanMX4 | | | | | | |
| 27 | 1043 | 44 | GFP.kanMX4 | 416 | 409 | 49.6 | 206 | 2.22E-16 | 3 |
| Diploid # | allele 1 SZY# | allele 2 SZY# | ade6 GENOTYPE | | | | | | |
| 28 | 1064 | 1035 | 5x wwd.kanMX4 | 163 | | | | | 3 |
| 29 | 1084 | 1049 | GFP.kanMX4 | | 222 | 54.98 | 101 | 2.22E-16 | 2 |

SEQUENCE LISTING

```
<160> NUMBER OF SEQ ID NOS: 76

<210> SEQ ID NO 1
<211> LENGTH: 295
<212> TYPE: PRT
<213> ORGANISM: Schizosaccharomyces

<400> SEQUENCE: 1

Met Leu Ser Glu Ile Trp Lys Tyr Ile Lys Thr Val Ser Glu Asp Ser
1               5                   10                  15

Ser Thr Gly Pro Thr Glu Thr Thr Asn Pro Asn Val Glu Arg Arg Gln
            20                  25                  30

Glu Phe Lys Asp Ser His Pro Asn Ile Tyr Ser Leu Leu Arg Leu Leu
        35                  40                  45

Ile Ser Val Leu Ala Val Ile Val Val Phe Phe Thr Ala Trp Val Cys
    50                  55                  60

Val Asn Pro Leu Glu Lys Ser Ile Phe Gly Lys Val Ala Phe Phe Val
65                  70                  75                  80

Thr Ile Gly Ile Thr Cys Pro Ile Leu Leu Ile Thr Ile Phe Cys Phe
                85                  90                  95

Phe Glu Thr Trp Thr Gln Ala Val Ala Gln Cys Ile Lys Val Thr Val
            100                 105                 110

Ile Phe Leu Ala Gln Cys Val Lys Val Thr Ala Val Gly Leu Tyr Asn
        115                 120                 125

Ser Arg Glu Lys Trp Val Val Ile Ile Trp Leu Leu Trp Val Val Ile
    130                 135                 140

Cys Tyr Thr Leu Phe Leu Arg Ser Lys Phe Gly Asn Leu Asn Leu Asn
145                 150                 155                 160
```

```
Lys Ala Leu Ile Cys Ser Thr Cys Ser Ile Ser Ala Ala Leu Leu Leu
            165                 170                 175

Phe Leu Leu Tyr Val Arg Leu Pro Phe Trp Thr Leu Lys His Met Phe
            180                 185                 190

Ser Gly Leu Phe Gln Val Leu Gly Val Gln Ser Cys Val Val Ile Val
            195                 200                 205

Thr Lys Gly Leu Thr Tyr Leu Phe Asp Lys His Ile Asp Ala Thr Gly
            210                 215                 220

Tyr Glu Ile Glu Ala Ser Ser Leu Phe Val Ile Gly Asn Phe Leu Phe
225                 230                 235                 240

Phe Tyr Glu Met Glu Cys Pro Gly Ala Leu Lys Arg Met Pro Lys Phe
            245                 250                 255

Ile Arg Asn Gly Ile Ala Ser Phe Leu Glu Gly Ile Gly Asn Ile Gly
            260                 265                 270

Arg Ala Phe Arg Gly Ala Asn Asp Asn Asp Ile Pro Leu Gly Glu
            275                 280                 285

Met Glu Val Glu Ser Glu Val
            290                 295

<210> SEQ ID NO 2
<211> LENGTH: 337
<212> TYPE: PRT
<213> ORGANISM: Schizosaccharomyces

<400> SEQUENCE: 2

Met Lys Asn Lys Asp Tyr Pro Leu Arg Ser Ser Met Asp Glu Leu Ser
1               5                   10                  15

Thr Lys Asn Asp Asn Glu Ile Asp Leu Glu Lys Gly Pro Leu Pro Glu
            20                  25                  30

Tyr Asn Ser Glu Asp Glu Ser Thr Leu Pro Pro Tyr Ser Glu Ile Trp
            35                  40                  45

Lys Tyr Ile Lys Thr Val Ser Glu Asp Ser Ser Thr Gly Pro Thr Glu
    50                  55                  60

Thr Thr Asn Pro Asn Val Glu Arg Arg Gln Glu Phe Lys Asp Ser His
65                  70                  75                  80

Pro Asn Ile Tyr Ser Leu Leu Arg Leu Leu Ile Ser Val Leu Ala Val
                85                  90                  95

Ile Val Val Phe Phe Thr Ala Trp Val Cys Val Asn Pro Leu Glu Lys
            100                 105                 110

Ser Ile Phe Gly Lys Val Ala Phe Phe Val Thr Ile Gly Ile Thr Cys
            115                 120                 125

Pro Ile Leu Leu Ile Thr Ile Phe Cys Phe Phe Glu Thr Trp Thr Gln
            130                 135                 140

Ala Val Ala Gln Cys Ile Lys Val Thr Val Ile Phe Leu Ala Gln Cys
145                 150                 155                 160

Val Lys Val Thr Ala Val Gly Leu Tyr Asn Ser Arg Glu Lys Trp Val
            165                 170                 175

Val Ile Ile Trp Leu Leu Trp Val Val Ile Cys Tyr Thr Leu Phe Leu
            180                 185                 190

Arg Ser Lys Phe Gly Asn Leu Asn Leu Asn Lys Ala Leu Ile Cys Ser
            195                 200                 205

Thr Cys Ser Ile Ser Ala Ala Leu Leu Leu Phe Leu Leu Tyr Val Arg
            210                 215                 220

Leu Pro Phe Trp Thr Leu Lys His Met Phe Ser Gly Leu Phe Gln Val
```

-continued

```
                225                 230                 235                 240
Leu Gly Val Gln Ser Cys Val Val Ile Val Thr Lys Gly Leu Thr Tyr
                245                 250                 255

Leu Phe Asp Lys His Ile Asp Ala Thr Gly Tyr Glu Ile Glu Ala Ser
                260                 265                 270

Ser Leu Phe Val Ile Gly Asn Phe Leu Phe Tyr Glu Met Glu Cys
                275                 280                 285

Pro Gly Ala Leu Lys Arg Met Pro Lys Phe Ile Arg Asn Gly Ile Ala
                290                 295                 300

Ser Phe Leu Glu Gly Ile Gly Asn Ile Gly Arg Ala Phe Arg Gly Ala
305                 310                 315                 320

Asn Asp Asn Asn Asp Ile Pro Leu Gly Glu Met Glu Val Glu Ser Glu
                    325                 330                 335

Val

<210> SEQ ID NO 3
<211> LENGTH: 342
<212> TYPE: PRT
<213> ORGANISM: Schizosaccharomyces

<400> SEQUENCE: 3

Met Gly Gln Asn Ile Thr Lys Leu Phe Asn Trp Asn Lys Ser Thr Thr
1               5                   10                  15

Pro Pro Asp Tyr Asp Glu Asn Arg Leu Pro Ile Thr Asp Glu Gly Asn
                20                  25                  30

Asn Pro Pro Asn Thr His Arg Glu Asn His Ser Ser Gly Thr Ala Asp
            35                  40                  45

Asn Ser Ser Pro Phe Leu Ile Lys Leu Ile Ile Ser Phe Thr Pro Ile
50                  55                  60

Phe Val Leu Asn Val Pro Ala Val Cys Tyr Leu Thr Tyr Lys Asp Ala
65                  70                  75                  80

Leu Phe Lys Asp Tyr Gly Lys Asp Glu Trp Val Tyr Phe Gly Val Trp
                85                  90                  95

Cys Ala Ile Cys Leu Met Ser Phe Ile Ser Leu Trp Cys Phe Tyr Glu
            100                 105                 110

Thr Trp Thr Lys Ala Val Lys Val Thr Val Ile Phe Leu Ala Gln Cys
        115                 120                 125

Val Lys Val Thr Val Ile Phe Leu Ala Gln Cys Val Lys Val Thr Ala
    130                 135                 140

Ile Phe Ser Ala Gln Cys Ile Lys Val Thr Val Ile Ser Leu Ala Lys
145                 150                 155                 160

Cys Val Lys Val Ile Ala Val Gly Leu Tyr Asn Ser Lys Lys Asp Leu
                165                 170                 175

Val Val Thr Ile Trp Leu Ala Trp Val Val Ile Cys Phe Ile Leu Phe
            180                 185                 190

Gly Cys Val Lys Asp Gly Arg Leu Asn Leu Asn Lys Ala Leu Ile Cys
        195                 200                 205

Ser Thr Ser Ser Ile Ser Ala Ala Leu Phe Phe Ile Leu Leu Leu Val
    210                 215                 220

Cys Ile Pro Ile Trp Thr Leu Lys His Met Leu Phe Gly Leu Phe Gln
225                 230                 235                 240

Val Leu Gly Val Gln Ser Cys Val Val Ile Val Thr Lys Gly Leu Met
                245                 250                 255

Tyr Leu Phe Asp Lys His Ile Asp Ala Thr Gly Tyr Glu Ile Glu Ala
```

```
            260                 265                 270
Ser Ser Leu Phe Val Ile Gly Asn Phe Leu Phe Phe Tyr Glu Met Glu
        275                 280                 285

Arg Pro Gly Ala Leu Lys Arg Met Pro Lys Phe Ile Arg Asn Gly Ile
290                 295                 300

Ala Ser Phe Leu Gly Gly Ile Ala Asn Ala Phe Gly Gly Ile Ala Asn
305                 310                 315                 320

Ala Ile Arg Gly Ala Asn Asp Asn Asn Asp Ile Pro Leu Gly Glu Met
                325                 330                 335

Glu Val Glu Ser Glu Val
                340

<210> SEQ ID NO 4
<211> LENGTH: 397
<212> TYPE: PRT
<213> ORGANISM: Schizosaccharomyces

<400> SEQUENCE: 4

Met Lys Asn Lys Tyr Tyr Pro Leu Arg Ser Ser Met Asp Glu Leu Ser
1               5                   10                  15

Thr Lys Asn Asp Asn Glu Ile Asp Leu Glu Lys Gly Pro Leu Pro Glu
            20                  25                  30

Tyr Asn Ser Glu Asp Gly Asn Thr Leu Pro Pro Tyr Ser Glu Asn Ile
        35                  40                  45

Asn Leu Lys Asp Pro Lys Gln Met Gly Gln Asn Ile Thr Lys Leu Phe
    50                  55                  60

Asn Trp Asn Lys Ser Thr Thr Pro Pro Asp Tyr Asp Glu Asn Arg Leu
65                  70                  75                  80

Pro Ile Thr Asp Glu Gly Asn Asn Pro Pro Asn Thr His Arg Glu Asn
                85                  90                  95

His Ser Ser Gly Thr Ala Asp Asn Ser Ser Pro Phe Leu Ile Lys Leu
            100                 105                 110

Ile Ile Ser Phe Thr Pro Ile Phe Val Leu Asn Val Pro Ala Val Cys
        115                 120                 125

Tyr Leu Thr Tyr Lys Asp Ala Leu Phe Lys Asp Tyr Gly Lys Asp Glu
    130                 135                 140

Trp Val Tyr Phe Gly Val Trp Cys Ala Ile Cys Leu Met Ser Phe Ile
145                 150                 155                 160

Ser Leu Trp Cys Phe Tyr Glu Thr Trp Thr Lys Ala Val Lys Val Thr
                165                 170                 175

Val Ile Phe Leu Ala Gln Cys Val Lys Val Thr Val Ile Phe Leu Ala
            180                 185                 190

Gln Cys Val Lys Val Thr Ala Ile Phe Ser Ala Gln Cys Ile Lys Val
        195                 200                 205

Thr Val Ile Ser Leu Ala Lys Cys Val Lys Val Ile Ala Val Gly Leu
    210                 215                 220

Tyr Asn Ser Lys Lys Asp Leu Val Val Thr Ile Trp Leu Ala Trp Val
225                 230                 235                 240

Val Ile Cys Phe Ile Leu Phe Gly Cys Val Lys Asp Gly Arg Leu Asn
                245                 250                 255

Leu Asn Lys Ala Leu Ile Cys Ser Thr Ser Ile Ser Ala Ala Leu
            260                 265                 270

Phe Phe Ile Leu Leu Leu Val Cys Ile Pro Ile Trp Thr Leu Lys His
        275                 280                 285
```

```
Met Leu Phe Gly Leu Phe Gln Val Leu Gly Val Gln Ser Cys Val Val
        290                 295                 300

Ile Val Thr Lys Gly Leu Met Tyr Leu Phe Asp Lys His Ile Asp Ala
305                 310                 315                 320

Thr Gly Tyr Glu Ile Glu Ala Ser Ser Leu Phe Val Ile Gly Asn Phe
                325                 330                 335

Leu Phe Phe Tyr Glu Met Glu Arg Pro Gly Ala Leu Lys Arg Met Pro
            340                 345                 350

Lys Phe Ile Arg Asn Gly Ile Ala Ser Phe Leu Gly Gly Ile Ala Asn
        355                 360                 365

Ala Phe Gly Gly Ile Ala Asn Ala Ile Arg Gly Ala Asn Asp Asn Asn
370                 375                 380

Asp Ile Pro Leu Gly Glu Met Glu Val Glu Ser Glu Val
385                 390                 395

<210> SEQ ID NO 5
<211> LENGTH: 100
<212> TYPE: DNA
<213> ORGANISM: Artificial Sequence
<220> FEATURE:
<223> OTHER INFORMATION: Oligo

<400> SEQUENCE: 5
tattacatca gtgcgctatc agtttaaaag gttgggccta ctaacttaac atatactaca      60
cctcaagaaa aagaaagaac acatacgatt taggtgacac                           100

<210> SEQ ID NO 6
<211> LENGTH: 100
<212> TYPE: DNA
<213> ORGANISM: Artificial Sequence
<220> FEATURE:
<223> OTHER INFORMATION: Oligo

<400> SEQUENCE: 6
tttgcacagc agaaatttga ttattgcttg gctcaagtac atggtgagta tgacattatt      60
attgagaacg acctggcata atacgactca ctataggga                            100

<210> SEQ ID NO 7
<211> LENGTH: 41
<212> TYPE: DNA
<213> ORGANISM: Artificial Sequence
<220> FEATURE:
<223> OTHER INFORMATION: Oligo

<400> SEQUENCE: 7
gtcggatccc attcgttatc gttccaagtg tgctgccgtc g                          41

<210> SEQ ID NO 8
<211> LENGTH: 55
<212> TYPE: DNA
<213> ORGANISM: Artificial Sequence
<220> FEATURE:
<223> OTHER INFORMATION: Oligo

<400> SEQUENCE: 8
gtcagatctc tgttttggaa acttttttat cctctaacga tgacgataaa tttac           55

<210> SEQ ID NO 9
<211> LENGTH: 44
<212> TYPE: DNA
<213> ORGANISM: Artificial Sequence
<220> FEATURE:
```

<223> OTHER INFORMATION: Oligo

<400> SEQUENCE: 9
gtcgagctca atacaggtaa atggtctaaa tcagtatgta agcc    44

<210> SEQ ID NO 10
<211> LENGTH: 42
<212> TYPE: DNA
<213> ORGANISM: Artificial Sequence
<220> FEATURE:
<223> OTHER INFORMATION: Oligo

<400> SEQUENCE: 10
gtcactagtg ctatgattcc gggaattgat gtttcttctg ac    42

<210> SEQ ID NO 11
<211> LENGTH: 29
<212> TYPE: DNA
<213> ORGANISM: Artificial Sequence
<220> FEATURE:
<223> OTHER INFORMATION: Oligo

<400> SEQUENCE: 11
ctctgaagac gcaggtagta aaaaacccg    29

<210> SEQ ID NO 12
<211> LENGTH: 31
<212> TYPE: DNA
<213> ORGANISM: Artificial Sequence
<220> FEATURE:
<223> OTHER INFORMATION: Oligo

<400> SEQUENCE: 12
gtgagtatgt accttcaata cacccttgat g    31

<210> SEQ ID NO 13
<211> LENGTH: 29
<212> TYPE: DNA
<213> ORGANISM: Artificial Sequence
<220> FEATURE:
<223> OTHER INFORMATION: Oligo

<400> SEQUENCE: 13
ctgcgtagct gacatgttat tgcgataac    29

<210> SEQ ID NO 14
<211> LENGTH: 29
<212> TYPE: DNA
<213> ORGANISM: Artificial Sequence
<220> FEATURE:
<223> OTHER INFORMATION: Oligo

<400> SEQUENCE: 14
gcattgcttg aaagattctg cgatgttgg    29

<210> SEQ ID NO 15
<211> LENGTH: 35
<212> TYPE: DNA
<213> ORGANISM: Artificial Sequence
<220> FEATURE:
<223> OTHER INFORMATION: Oligo

<400> SEQUENCE: 15
ggttagagta aattacagga atatataacg aaccc    35

```
<210> SEQ ID NO 16
<211> LENGTH: 35
<212> TYPE: DNA
<213> ORGANISM: Artificial Sequence
<220> FEATURE:
<223> OTHER INFORMATION: Oligo

<400> SEQUENCE: 16
gggttcgtta tatattcctg taatttactc taacc                           35

<210> SEQ ID NO 17
<211> LENGTH: 29
<212> TYPE: DNA
<213> ORGANISM: Artificial Sequence
<220> FEATURE:
<223> OTHER INFORMATION: Oligo

<400> SEQUENCE: 17
ctaccttgcc gaatatcgac ttctccaac                                  29

<210> SEQ ID NO 18
<211> LENGTH: 29
<212> TYPE: DNA
<213> ORGANISM: Artificial Sequence
<220> FEATURE:
<223> OTHER INFORMATION: Oligo

<400> SEQUENCE: 18
gttggagaag tcgatattcg gcaaggtag                                  29

<210> SEQ ID NO 19
<211> LENGTH: 26
<212> TYPE: DNA
<213> ORGANISM: Artificial Sequence
<220> FEATURE:
<223> OTHER INFORMATION: Oligo

<400> SEQUENCE: 19
ctgaacgagg cagtggattg cttctg                                     26

<210> SEQ ID NO 20
<211> LENGTH: 26
<212> TYPE: DNA
<213> ORGANISM: Artificial Sequence
<220> FEATURE:
<223> OTHER INFORMATION: Oligo

<400> SEQUENCE: 20
cagaagcaat ccactgcctc gttcag                                     26

<210> SEQ ID NO 21
<211> LENGTH: 30
<212> TYPE: DNA
<213> ORGANISM: Artificial Sequence
<220> FEATURE:
<223> OTHER INFORMATION: Oligo

<400> SEQUENCE: 21
gttatgatgg agaacccgga aattagaggc                                 30

<210> SEQ ID NO 22
<211> LENGTH: 51
<212> TYPE: DNA
<213> ORGANISM: Artificial Sequence
<220> FEATURE:
<223> OTHER INFORMATION: Oligo
```

<400> SEQUENCE: 22
gtgtcaccta atcgtatgt ggggaacaga aataaacaag tctaaagtgc c         51

<210> SEQ ID NO 23
<211> LENGTH: 52
<212> TYPE: DNA
<213> ORGANISM: Artificial Sequence
<220> FEATURE:
<223> OTHER INFORMATION: Oligo

<400> SEQUENCE: 23
ctccctatag tgagtcgtat taaactgcgt agctgacatg acactgaatt tc        52

<210> SEQ ID NO 24
<211> LENGTH: 30
<212> TYPE: DNA
<213> ORGANISM: Artificial Sequence
<220> FEATURE:
<223> OTHER INFORMATION: Oligo

<400> SEQUENCE: 24
ccaggcaaca tccattctca tcagatgagg                                 30

<210> SEQ ID NO 25
<211> LENGTH: 33
<212> TYPE: DNA
<213> ORGANISM: Artificial Sequence
<220> FEATURE:
<223> OTHER INFORMATION: Oligo

<400> SEQUENCE: 25
atttctgttc cccacatacg atttaggtga cac                             33

<210> SEQ ID NO 26
<211> LENGTH: 35
<212> TYPE: DNA
<213> ORGANISM: Artificial Sequence
<220> FEATURE:
<223> OTHER INFORMATION: Oligo

<400> SEQUENCE: 26
cagctacgca gtttaatacg actcactata gggag                           35

<210> SEQ ID NO 27
<211> LENGTH: 22
<212> TYPE: DNA
<213> ORGANISM: Artificial Sequence
<220> FEATURE:
<223> OTHER INFORMATION: Oligo

<400> SEQUENCE: 27
cattttcaca aatggttcga gt                                         22

<210> SEQ ID NO 28
<211> LENGTH: 22
<212> TYPE: DNA
<213> ORGANISM: Artificial Sequence
<220> FEATURE:
<223> OTHER INFORMATION: Oligo

<400> SEQUENCE: 28
tcgaaccatt tgtgaaaatg tt                                         22

<210> SEQ ID NO 29
<211> LENGTH: 29

```
<212> TYPE: DNA
<213> ORGANISM: Artificial Sequence
<220> FEATURE:
<223> OTHER INFORMATION: Oligo

<400> SEQUENCE: 29
tggttaagca tgtgatcttc atacgacgc                                          29

<210> SEQ ID NO 30
<211> LENGTH: 29
<212> TYPE: DNA
<213> ORGANISM: Artificial Sequence
<220> FEATURE:
<223> OTHER INFORMATION: Oligo

<400> SEQUENCE: 30
agaaattcag tgtcatgtca gctacgcag                                          29

<210> SEQ ID NO 31
<211> LENGTH: 27
<212> TYPE: DNA
<213> ORGANISM: Artificial Sequence
<220> FEATURE:
<223> OTHER INFORMATION: Oligo

<400> SEQUENCE: 31
atgagcgaaa aacaggttgt agggatc                                            27

<210> SEQ ID NO 32
<211> LENGTH: 29
<212> TYPE: DNA
<213> ORGANISM: Artificial Sequence
<220> FEATURE:
<223> OTHER INFORMATION: Oligo

<400> SEQUENCE: 32
ggtacctgac ctgaattgtg aggccgagg                                          29

<210> SEQ ID NO 33
<211> LENGTH: 25
<212> TYPE: DNA
<213> ORGANISM: Artificial Sequence
<220> FEATURE:
<223> OTHER INFORMATION: Oligo

<400> SEQUENCE: 33
ccatagcagc caaaagggag ggttg                                              25

<210> SEQ ID NO 34
<211> LENGTH: 44
<212> TYPE: DNA
<213> ORGANISM: Artificial Sequence
<220> FEATURE:
<223> OTHER INFORMATION: Oligo

<400> SEQUENCE: 34
cacaattcag gtcaggtacc caacacccaa ctctcgactt ccac                         44

<210> SEQ ID NO 35
<211> LENGTH: 33
<212> TYPE: DNA
<213> ORGANISM: Artificial Sequence
<220> FEATURE:
<223> OTHER INFORMATION: Oligo

<400> SEQUENCE: 35
```

```
gggttgtaat gttacctatc actaatatag ctc                              33

<210> SEQ ID NO 36
<211> LENGTH: 38
<212> TYPE: DNA
<213> ORGANISM: Artificial Sequence
<220> FEATURE:
<223> OTHER INFORMATION: Oligo

<400> SEQUENCE: 36
gcttaattat cattttttcc atttgtttaa tggtttac                         38

<210> SEQ ID NO 37
<211> LENGTH: 31
<212> TYPE: DNA
<213> ORGANISM: Artificial Sequence
<220> FEATURE:
<223> OTHER INFORMATION: Oligo

<400> SEQUENCE: 37
cgggtaagta aagaatcatt catacagttg g                                31

<210> SEQ ID NO 38
<211> LENGTH: 24
<212> TYPE: DNA
<213> ORGANISM: Artificial Sequence
<220> FEATURE:
<223> OTHER INFORMATION: Oligo

<400> SEQUENCE: 38
ccgctaacac gcagttcgtc ttcc                                        24

<210> SEQ ID NO 39
<211> LENGTH: 30
<212> TYPE: DNA
<213> ORGANISM: Artificial Sequence
<220> FEATURE:
<223> OTHER INFORMATION: Oligo

<400> SEQUENCE: 39
cccttctgag actactaata tcagttcttg                                  30

<210> SEQ ID NO 40
<211> LENGTH: 30
<212> TYPE: DNA
<213> ORGANISM: Artificial Sequence
<220> FEATURE:
<223> OTHER INFORMATION: Oligo

<400> SEQUENCE: 40
ggaatcgagt cagcagttgt tatcaacggg                                  30

<210> SEQ ID NO 41
<211> LENGTH: 30
<212> TYPE: DNA
<213> ORGANISM: Artificial Sequence
<220> FEATURE:
<223> OTHER INFORMATION: Oligo

<400> SEQUENCE: 41
cccgttgata acaactgctg actcgattcc                                  30

<210> SEQ ID NO 42
<211> LENGTH: 28
<212> TYPE: DNA
<213> ORGANISM: Artificial Sequence
```

```
<220> FEATURE:
<223> OTHER INFORMATION: Oligo

<400> SEQUENCE: 42
ctgaatatgg aggcaatgtg ctctcatc                                              28

<210> SEQ ID NO 43
<211> LENGTH: 37
<212> TYPE: DNA
<213> ORGANISM: Artificial Sequence
<220> FEATURE:
<223> OTHER INFORMATION: Oligo

<400> SEQUENCE: 43
atgaagaata aagattatcc cttgaggtcg tctatgg                                    37

<210> SEQ ID NO 44
<211> LENGTH: 46
<212> TYPE: DNA
<213> ORGANISM: Artificial Sequence
<220> FEATURE:
<223> OTHER INFORMATION: Oligo

<400> SEQUENCE: 44
taaaccagca ccgtcaccga cttcgctttc aacttccatt tccccc                          46

<210> SEQ ID NO 45
<211> LENGTH: 46
<212> TYPE: DNA
<213> ORGANISM: Artificial Sequence
<220> FEATURE:
<223> OTHER INFORMATION: Oligo

<400> SEQUENCE: 45
gggggaaatg gaagttgaaa gcgaagtcgg tgacggtgct ggttta                          46

<210> SEQ ID NO 46
<211> LENGTH: 42
<212> TYPE: DNA
<213> ORGANISM: Artificial Sequence
<220> FEATURE:
<223> OTHER INFORMATION: Oligo

<400> SEQUENCE: 46
aatataggag ctctggttaa gcatgtgatc ttcatacgac gc                              42

<210> SEQ ID NO 47
<211> LENGTH: 42
<212> TYPE: DNA
<213> ORGANISM: Artificial Sequence
<220> FEATURE:
<223> OTHER INFORMATION: Oligo

<400> SEQUENCE: 47
aatataggag ctcagaaatt cagtgtcatg tcagctacgc ag                              42

<210> SEQ ID NO 48
<211> LENGTH: 41
<212> TYPE: DNA
<213> ORGANISM: Artificial Sequence
<220> FEATURE:
<223> OTHER INFORMATION: Oligo

<400> SEQUENCE: 48
aatatagagc tcagaaattc agtgtcatgt cagctacgca g                               41
```

<210> SEQ ID NO 49
<211> LENGTH: 33
<212> TYPE: DNA
<213> ORGANISM: Artificial Sequence
<220> FEATURE:
<223> OTHER INFORMATION: Oligo

<400> SEQUENCE: 49
aatatagagc tccggggacg aggcaagcta aac                                    33

<210> SEQ ID NO 50
<211> LENGTH: 49
<212> TYPE: DNA
<213> ORGANISM: Artificial Sequence
<220> FEATURE:
<223> OTHER INFORMATION: Oligo

<400> SEQUENCE: 50
aatatagagc tcaatgcttc aaaataattt tgtaaatcat gttatgccg                   49

<210> SEQ ID NO 51
<211> LENGTH: 40
<212> TYPE: DNA
<213> ORGANISM: Artificial Sequence
<220> FEATURE:
<223> OTHER INFORMATION: Oligo

<400> SEQUENCE: 51
aatatagagc tctctatcac aaaaaaggtt gcagcggagc                             40

<210> SEQ ID NO 52
<211> LENGTH: 41
<212> TYPE: DNA
<213> ORGANISM: Artificial Sequence
<220> FEATURE:
<223> OTHER INFORMATION: Oligo

<400> SEQUENCE: 52
aatatagagc tccggctact gataattgcc ttgcactctt c                           41

<210> SEQ ID NO 53
<211> LENGTH: 44
<212> TYPE: DNA
<213> ORGANISM: Artificial Sequence
<220> FEATURE:
<223> OTHER INFORMATION: Oligo

<400> SEQUENCE: 53
aatatagagc tccgaattga gtttgtagga agaaacaaag ttcc                        44

<210> SEQ ID NO 54
<211> LENGTH: 44
<212> TYPE: DNA
<213> ORGANISM: Artificial Sequence
<220> FEATURE:
<223> OTHER INFORMATION: Oligo

<400> SEQUENCE: 54
aatatagagc tcggctcttc gatgcaaagt aaggtaagta gttg                        44

<210> SEQ ID NO 55
<211> LENGTH: 43
<212> TYPE: DNA
<213> ORGANISM: Artificial Sequence
<220> FEATURE:
<223> OTHER INFORMATION: Oligo

<400> SEQUENCE: 55
aatatagagc tccatctcta aacccgtatt tggtagaaac ggc                43

<210> SEQ ID NO 56
<211> LENGTH: 43
<212> TYPE: DNA
<213> ORGANISM: Artificial Sequence
<220> FEATURE:
<223> OTHER INFORMATION: Oligo

<400> SEQUENCE: 56
aatatagagc tcccgaagta tcatatcaac gtagtacacc atg                43

<210> SEQ ID NO 57
<211> LENGTH: 36
<212> TYPE: DNA
<213> ORGANISM: Artificial Sequence
<220> FEATURE:
<223> OTHER INFORMATION: Oligo

<400> SEQUENCE: 57
aatatagagc tcggaggcaa agccaaacgt tctagc                        36

<210> SEQ ID NO 58
<211> LENGTH: 45
<212> TYPE: DNA
<213> ORGANISM: Artificial Sequence
<220> FEATURE:
<223> OTHER INFORMATION: Oligo

<400> SEQUENCE: 58
aatataggag ctctataata gatcacaaag gaaaactcgc cgcag              45

<210> SEQ ID NO 59
<211> LENGTH: 48
<212> TYPE: DNA
<213> ORGANISM: Artificial Sequence
<220> FEATURE:
<223> OTHER INFORMATION: Oligo

<400> SEQUENCE: 59
aatataggag ctcctgcgta gcttacatgt tattgcgata acatttcg           48

<210> SEQ ID NO 60
<211> LENGTH: 56
<212> TYPE: DNA
<213> ORGANISM: Artificial Sequence
<220> FEATURE:
<223> OTHER INFORMATION: Oligo

<400> SEQUENCE: 60
gtgtatatca ttcaataata gattgttttt aagaatagaa gataaagat tatccc   56

<210> SEQ ID NO 61
<211> LENGTH: 56
<212> TYPE: DNA
<213> ORGANISM: Artificial Sequence
<220> FEATURE:
<223> OTHER INFORMATION: Oligo

<400> SEQUENCE: 61
gggataatct ttattcttct attcttaaaa acaatctatt attgaatgat atacac  56

<210> SEQ ID NO 62

```
<211> LENGTH: 43
<212> TYPE: DNA
<213> ORGANISM: Artificial Sequence
<220> FEATURE:
<223> OTHER INFORMATION: Oligo

<400> SEQUENCE: 62
aatatagagc tcgcgttatt aatgtagttg tcgctacagt tgg          43

<210> SEQ ID NO 63
<211> LENGTH: 49
<212> TYPE: DNA
<213> ORGANISM: Artificial Sequence
<220> FEATURE:
<223> OTHER INFORMATION: Oligo

<400> SEQUENCE: 63
aatatagagc tccttcttat tcaccccaac ttagatttcc ttatgcatc    49

<210> SEQ ID NO 64
<211> LENGTH: 72
<212> TYPE: DNA
<213> ORGANISM: Artificial Sequence
<220> FEATURE:
<223> OTHER INFORMATION: Oligo

<400> SEQUENCE: 64
ccaaatttca aaagttattt attttattat acctttcaga aatttggaaa tatattaaaa    60
ctgtatctga ag                                                        72

<210> SEQ ID NO 65
<211> LENGTH: 70
<212> TYPE: DNA
<213> ORGANISM: Artificial Sequence
<220> FEATURE:
<223> OTHER INFORMATION: Oligo

<400> SEQUENCE: 65
cttcagatac agttttaata tatttccaaa tttctgaaag gtataataaa ataataact     60 tttgaaattt                                                           70

<210> SEQ ID NO 66
<211> LENGTH: 33
<212> TYPE: DNA
<213> ORGANISM: Artificial Sequence
<220> FEATURE:
<223> OTHER INFORMATION: Oligo

<400> SEQUENCE: 66
gtactcaatt catccttaag acgacctcaa ggg          33

<210> SEQ ID NO 67
<211> LENGTH: 32
<212> TYPE: DNA
<213> ORGANISM: Artificial Sequence
<220> FEATURE:
<223> OTHER INFORMATION: Oligo

<400> SEQUENCE: 67
cccttgaggt cgtcttagga tgaattgagt ac           32

<210> SEQ ID NO 68
<211> LENGTH: 30
<212> TYPE: DNA
<213> ORGANISM: Artificial Sequence
```

```
<220> FEATURE:
<223> OTHER INFORMATION: Oligo

<400> SEQUENCE: 68
aaatggaatg cccatcctga tcttaacttg                                30

<210> SEQ ID NO 69
<211> LENGTH: 55
<212> TYPE: DNA
<213> ORGANISM: Artificial Sequence
<220> FEATURE:
<223> OTHER INFORMATION: Oligo

<400> SEQUENCE: 69
tccctacaac ctgttttttcg ctcatcgtga tgcaaaacta ctcttttcaa ttaga    55

<210> SEQ ID NO 70
<211> LENGTH: 60
<212> TYPE: DNA
<213> ORGANISM: Artificial Sequence
<220> FEATURE:
<223> OTHER INFORMATION: Oligo

<400> SEQUENCE: 70
aaagttggtt ggaaaaatta ttctgcatag agatgaattg gattatgtca ggaaaagaac 60

<210> SEQ ID NO 71
<211> LENGTH: 30
<212> TYPE: DNA
<213> ORGANISM: Artificial Sequence
<220> FEATURE:
<223> OTHER INFORMATION: Oligo

<400> SEQUENCE: 71
gtgaacgatt agggacgaat tatcaactgt                                30

<210> SEQ ID NO 72
<211> LENGTH: 55
<212> TYPE: DNA
<213> ORGANISM: Artificial Sequence
<220> FEATURE:
<223> OTHER INFORMATION: Oligo

<400> SEQUENCE: 72
tctaattgaa aagagtagtt ttgcatcacg atgagcgaaa acaggttgt aggga       55

<210> SEQ ID NO 73
<211> LENGTH: 60
<212> TYPE: DNA
<213> ORGANISM: Artificial Sequence
<220> FEATURE:
<223> OTHER INFORMATION: Oligo

<400> SEQUENCE: 73
gttcttttcc tgacataatc caattcatct ctatgcagaa taatttttcc aaccactttt 60

<210> SEQ ID NO 74
<211> LENGTH: 21
<212> TYPE: DNA
<213> ORGANISM: Artificial Sequence
<220> FEATURE:
<223> OTHER INFORMATION: Oligo

<400> SEQUENCE: 74
taacgccgcc atccagtgtc g                                         21
```

```
<210> SEQ ID NO 75
<211> LENGTH: 25
<212> TYPE: DNA
<213> ORGANISM: Artificial Sequence
<220> FEATURE:
<223> OTHER INFORMATION: Oligo

<400> SEQUENCE: 75
gccgaatatc gacttctcca acggg                                          25

<210> SEQ ID NO 76
<211> LENGTH: 34
<212> TYPE: DNA
<213> ORGANISM: Artificial Sequence
<220> FEATURE:
<223> OTHER INFORMATION: Oligo

<400> SEQUENCE: 76
gccctgttag acgaatttat gctcgtaata tgtc                                34
```

COMPOSITIONS AND METHODS OF DUAL POISON-ANTIDOTE MEIOTIC DRIVERS

CROSS-REFERENCE TO RELATED APPLICATIONS

The present application is the National Stage of International Application No. PCT/US2018/029997, filed on Apr. 27, 2018, which claims benefit to U.S. Provisional Patent Application No. 62/491,107, filed Apr. 27, 2017. The entire contents of the above applications are incorporated by reference as if recited in full herein.

GOVERNMENT FUNDING

This invention was made with government support under grant nos. RO1 GM031693, R35 GM118120, RO1 GM074108, and K99/R00 GM114436 awarded by the National Institutes of Health. The government has certain rights in the invention.

FIELD OF THE DISCLOSURE

The present disclosure relates to meiotic drive genes which are selfish genes that bias their transmission into gametes, defying Mendelian inheritance. It further relates to use of meiotic drive genes to bias transmission of a gene of interest into a population of an organism.

INCORPORATION BY REFERENCE OF SEQUENCE LISTING

This application contains references to amino acids and/or nucleic acid sequences that have been filed as sequence listing text file "1065334-000153_ST25.txt", file size of 25 KB, created on May 12, 2020. The aforementioned sequence listing is hereby incorporated by reference in its entirety pursuant to 37 C.F.R. § 1.52(e)(5).

BACKGROUND OF THE INVENTION

Engineering the genome of organism populations may be useful for population control or population replacement of pest organisms and disease carrying organisms. This strategy, however, requires the forced spread of specific traits through a population of an organism with minimal human intervention. Thus, there is a need for engineered gene drive systems in organisms capable of effectively and specifically biasing the organisms' offspring toward having a specific gene or trait.

Gamete-killing meiotic drive alleles are one such class of selfish genes that can be used to engineer the genome of a population of organism. These genes act by killing the gametes that do not inherit them, increasing their transmission into up to 100% of the progeny of a heterozygote (2, 3). Meiotic drivers can also indirectly promote infertility or other disease states by short-circuiting the way natural selection usually works to choose the best adapted alleles. Natural selection cannot, for example, 'see' the potential fitness benefits of an allele carried in a gamete destroyed by a driver. Conversely, meiotic drivers can promote the spread of maladapted alleles that are genetically linked to the drive locus within a population (3, 4).

Gamete-killing meiotic drive has been observed in eukaryotes ranging from plants to mammals (2). With the broadening implementation of high-throughput sequencing, meiotic drivers are being discovered at an accelerated rate and it is hypothesized that these selfish genes are common (2, 5-8). However, relatively little is known about the actual prevalence of meiotic drivers. Only a handful of genes involved in meiotic drive have been mapped. Their lack of homology makes it nearly impossible to identify novel drive loci from genome sequences alone. Instead, rigorous genetic analyses are required to detect and map meiotic drive loci. These efforts are frequently impeded by the complexity of many drive systems; they often have multiple components and are found within chromosome rearrangements that are recalcitrant to genetic mapping (9, 10). Even in the case of well-studied meiotic drive systems where one or more components have been identified, a complete understanding of the mechanistic basis of drive or its suppression has been elusive (7, 9, 11-13).

SUMMARY OF THE INVENTION

According to some aspects, the present disclosure provides compositions, methods, and kits for spreading a meiotic drive gene and/or a gene of interest into the population of an organism.

Meiotic drivers are selfish genes that bias their transmission into gametes, defying Mendelian inheritance. According to some aspects, the present disclosure provides meiotic drive genes derived from, for example, chromosome 3 of the fission yeasts *Schizosaccharomyces kambucha* and *S. pombe* and orthologs thereof. *S. kambucha* wtf4 is identified as a gene that acts to kill gametes that do not inherit the gene from heterozygotes. wtf4 utilizes dual, overlapping transcripts to encode both a gamete-killing poison and an antidote to the poison. To enact drive, all gametes are poisoned, whereas only those that inherit wtf4 are rescued by the antidote. According to some embodiments, proliferation of the wtf multigene family due to meiotic drive is capable of shaping genomes, even while imposing costs to fertility.

According to some embodiments, the present disclosure provides a meiotic drive composition comprising a recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; wherein the first peptide sequence and the second peptide sequence are derived from alternative transcriptional start sites on the recombinant DNA sequence; and wherein the recombinant DNA sequence, when expressed in a diploid organism, is effective to bias offspring toward having the recombinant DNA.

According to some embodiments, the present disclosure provides a meiotic drive composition comprising: a recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; and wherein the recombinant DNA sequence, when expressed in a diploid organism, is effective to bias offspring toward having the recombinant DNA.

According to some embodiments, the present disclosure provides a meiotic drive composition comprising: a recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence and the second peptide sequence are derived from alternative transcriptional start sites on the recombinant DNA sequence; and wherein the recombinant DNA sequence, when expressed in a diploid organism, is effective to bias offspring toward having the recombinant DNA.

In some embodiments, the recombinant DNA sequence does not naturally occur in the diploid organism. In some embodiments, the recombinant DNA sequence is adapted to integrate into the genome of the diploid organism. In some embodiments, the present disclosure provides a vector comprising the recombinant DNA sequence and a heterologous DNA sequence.

According to some embodiments, the present disclosure provides a method of propagating a recombinant DNA sequence in a diploid organism's offspring comprising the steps of: expressing the recombinant DNA sequence in the diploid organism, wherein the DNA sequence encodes a first peptide sequence and a second peptide sequence, the first peptide sequence capable of destroying a gamete of the organism and the second peptide sequence capable of rescuing a gamete of the organism from the first peptide sequence; wherein the first peptide sequence is transported outside of a cell and the second peptide sequence is not transported outside of a cell; wherein the first peptide sequence and the second peptide sequence are derived from alternative transcriptional start sites on the recombinant DNA sequence; and wherein the recombinant DNA sequence, when expressed in a diploid organism, is effective to bias offspring toward having the recombinant DNA sequence; and permitting reproduction of the organism.

According to some embodiments, the present disclosure provides a method of propagating a recombinant DNA sequence in a diploid organism's offspring comprising the steps of: expressing the recombinant DNA sequence in the diploid organism, wherein the DNA sequence encodes a first peptide sequence and a second peptide sequence, the first peptide sequence capable of destroying a gamete of the organism and the second peptide sequence capable of rescuing a gamete of the organism from the first peptide sequence; wherein the first peptide sequence is transported outside of a cell and the second peptide sequence is not transported outside of a cell; and wherein the recombinant DNA sequence, when expressed in a diploid organism, is effective to bias offspring toward having the recombinant DNA sequence; and permitting reproduction of the organism.

According to some embodiments, the present disclosure provides a method of propagating a recombinant DNA sequence in a diploid organism's offspring comprising the steps of: expressing the recombinant DNA sequence in the diploid organism, wherein the DNA sequence encodes a first peptide sequence and a second peptide sequence, the first peptide sequence capable of destroying a gamete of the organism and the second peptide sequence capable of rescuing a gamete of the organism from the first peptide sequence; wherein the first peptide sequence and the second peptide sequence are derived from alternative transcriptional start sites on the recombinant DNA sequence; and wherein the recombinant DNA sequence, when expressed in a diploid organism, is effective to bias offspring toward having the recombinant DNA sequence; and permitting reproduction of the organism.

In some embodiments, the recombinant DNA sequence does not naturally occur in the diploid organism. In some embodiments, the recombinant DNA sequence is adapted to integrate into the genome of the diploid organism.

According to some embodiments, the present disclosure provides a meiotic drive composition comprising: a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; wherein the first peptide sequence and the second peptide sequence are derived from alternative transcriptional start sites on the first recombinant DNA sequence; and a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence.

According to some embodiments, the present disclosure provides a meiotic drive composition comprising: a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; and a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence.

According to some embodiments, the present disclosure provides a meiotic drive composition comprising: a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence and the second peptide sequence are derived from alternative transcriptional start sites on the first recombinant DNA sequence; and a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence.

In some embodiments, the first recombinant DNA sequence does not naturally occur in the diploid organism. In some embodiments, the second recombinant DNA sequence does not naturally occur in the diploid organism. In some embodiments, the first recombinant DNA sequence and/or second recombinant DNA sequence is adapted to integrate into the genome of the diploid organism. In some embodiments, the present disclosure provides a vector comprising the first recombinant DNA sequence and/or second recombinant DNA sequence and a heterologous DNA sequence. In some embodiments, the second recombinant DNA sequence is operably linked to the first recombinant DNA sequence via proximity of the first and second recombinant DNA sequences on a chromosome. In some embodiments, the second recombinant DNA sequence is adjacent to the first recombinant DNA sequence and there is continuous transcription of the first and second recombinant DNA sequences.

According to some embodiments, the present disclosure provides a method of propagating one or more recombinant DNA sequences in a diploid organism's offspring comprising the steps of: (i) expressing in the organism a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; wherein the first peptide sequence and the second peptide sequence are derived from alternative transcriptional start sites on the first recombinant DNA sequence; and (ii) expressing in the organism a second recombinant DNA sequence operably linked to the first recombinant DNA sequence, wherein the second recombinant DNA sequence encodes a gene of interest; and (iii) permitting reproduction of the organism; wherein the first recombinant DNA sequence, when expressed in the organism, is effective to bias offspring toward having both the first recombinant DNA sequence and the second recombinant DNA sequence.

According to some embodiments, the present disclosure provides a method of propagating one or more recombinant DNA sequences in a diploid organism's offspring comprising the steps of: (i) expressing in the organism a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence and the second peptide sequence are derived from alternative transcriptional start sites on the first recombinant DNA sequence; and (ii) expressing in the organism a second recombinant DNA sequence operably linked to the first recombinant DNA sequence, wherein the second recombinant DNA sequence encodes a gene of interest; and (iii) permitting reproduction of the organism; wherein the first recombinant DNA sequence, when expressed in the organism, is effective to bias offspring toward having both the first recombinant DNA sequence and the second recombinant DNA sequence.

According to some embodiments, the present disclosure provides a method of propagating one or more recombinant DNA sequences in a diploid organism's offspring comprising the steps of: (i) expressing in the organism a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; (ii) expressing in the organism a second recombinant DNA sequence operably linked to the first recombinant DNA sequence, wherein the second recombinant DNA sequence encodes a gene of interest; and (iii) permitting reproduction of the organism; wherein the first recombinant DNA sequence, when expressed in the organism, is effective to bias offspring toward having both the first recombinant DNA sequence and the second recombinant DNA sequence.

In some embodiments, the first recombinant DNA sequence does not naturally occur in the diploid organism. In some embodiments, the second recombinant DNA sequence does not naturally occur in the diploid organism. In some embodiments, the first recombinant DNA sequence and/or second recombinant DNA sequence is adapted to integrate into the genome of the diploid organism. In some embodiments, the second recombinant DNA sequence is linked to the first recombinant DNA sequence via proximity of the first and second recombinant DNA sequences on a chromosome. In some embodiments, the second recombinant DNA sequence is adjacent to the first recombinant DNA sequence and there is continuous transcription of the first and second recombinant DNA sequences.

According to some embodiments, the present disclosure provides a kit comprising: (1) a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; wherein the first peptide sequence and the second peptide sequence are derived from alternative transcriptional start sites on the first recombinant DNA sequence; (2) a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence; (3) reagents for expressing the first recombinant DNA sequence and/or the second recombinant DNA sequence in the diploid organism.

According to some embodiments, the present disclosure provides a kit comprising: (1) a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence and the second peptide sequence are derived from alternative transcriptional start sites on the first recombinant DNA sequence; (2) a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence; (3) reagents for expressing the first recombinant DNA sequence and/or the second recombinant DNA sequence in the diploid organism.

According to some embodiments, the present disclosure provides a kit comprising: (1) a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; (2) a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence; and (3) reagents for expressing the first recombinant DNA sequence and/or the second recombinant DNA sequence in the diploid organism.

In some embodiments, the first peptide sequence has at least 70% identity to the group of peptide sequences selected from SEQ ID NOs: 1 and 3. In some embodiments, the first peptide sequence has at least 80% identity to the group of peptide sequences selected from SEQ ID NOs: 1 and 3. In some embodiments, the first peptide sequence has at least 90% identity to the group of peptide sequences selected from SEQ ID NOs: 1 and 3. In some embodiments, the second peptide sequence has at least 70% identity to the group of peptide sequences selected from SEQ ID NOs: 2 and 4. In some embodiments, the second peptide sequence has at least 80% identity to the group of peptide sequences selected from SEQ ID NOs: 2 and 4. In some embodiments, the second peptide sequence has at least 90% identity to the group of peptide sequences selected from SEQ ID NOs: 2 and 4.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 1A to FIG. 1G shows a complex meiotic drive landscape on Sk and Sp chromosome 3, revealed by recombination mapping. FIG. 1A shows that a cross between Sk and Sp generates a heterozygote that has low fertility and preferentially transmits Sk alleles on all three chromosomes into viable gametes (18). FIG. 1B shows generation of chromosome 3 introgression diploids 1-8. Sk-derived DNA is shown in purple while Sp-derived DNA is shown in green. The origin of the Sp/Sk mosaic chromosome is depicted in FIG. 1E. FIG. 1C shows phenotypes of rec12Δ/rec12Δ introgression/Sk diploids. See FIG. 1F for breakpoints between Sk-derived DNA (purple) and Sp-derived DNA (green). Chromosome transmission was followed using the heterozygous markers at the ade6 locus: hph is short for the hphMX4 marker gene which confers resistance to hygromycin (HygR). The percentage of gametes that inherit both markers (heterozygous disomes, likely aneuploids and diploids) and (after excluding the heterozygous disomes) the percent of gametes that inherit the marker from the pure Sk chromosome are shown. Over 100 viable gametes were tested for each diploid; raw data can be found in FIG. 1G. * indicates p-value<0.01 (G-test) compared to rec12Δ/rec12Δ Sk control (from (18)). FIG. 1D shows fine-scale mapping of the drive locus starting with the introgression from diploid 1. Strains that were recombinant between the ura4 locus and an introduced kanMX4 marker gene were selected and their phenotypes were tested in crosses to Sk. The recombinant strain with the smallest amount of Sp DNA that retained the phenotype (sensitivity to drive by an Sk chromosome) is shown in detail. This introgression strain was mated to Sk to generate diploid 9. These analyses identified a ~30 kb candidate region (see blow up) containing a drive locus. In Sp, this region contains wtf4 and the wtf3 pseudogene. The syntenic region in Sk contains only one wtf gene, wtf4.

FIG. 1E shows the generation of mosaic chromosome 3 used in FIG. 1B. The goal of these crosses was to generate a strain containing mostly Sp-derived DNA on chromosome 3 in an otherwise Sk background. This effort was complicated by the different karyotypes of Sp and Sk chromosomes 2 and 3 (18). rec12Δ strains were used to limit recombination, but rare recombinants (e.g. SZY239 and SZY247) can still be obtained via selection. Markers derived from the Sk parent are shown in purple while Sp-derived markers are green. First isolated hybrids were obtained in which Sk and Sp markers on chromosomes 2 and 3 were uncoupled, suggesting rare recombination events had occurred between Sk and Sp chromosomes 2 and 3. Such events have the potential to generate chromosome 3 variants with mostly Sp DNA, but with an Sk karyotype, as occurred in SZY247. The illustrated crosses were then performed to move that chromosome into a different strain background with pure Sk chromosomes 1 and 2. SZY558 was finally sequenced and verified the strain has Sk chromosomes 1 and 2 and Sp DNA on chromosome 3 until between SNPs at positions 1,804,477 and 1,810,659.

FIG. 1F shows breakpoints between Sp and Sk-derived DNA sequences. The introgression strains used in diploids 1-8 were sequenced and genotyped for single-nucleotide polymorphisms (SNPs) that reliably distinguish Sk and Sp as in (18). The SNPs flanking the recombination event (left and right boundaries) that generated each breakpoint between Sp and Sk DNA for each introgression strain are shown. The coordinates refer to the position of the SNP on Sp chromosome 3. For the introgression used in diploid 9, SNPs were genotyped via PCR and Sanger sequencing.

FIG. 1G shows the raw data underlying FIG. 1C. Diploids 1-10 (column 1) were generated by crossing the indicated haploid strains (columns 2 and 4). The diploid numbers correspond to those in FIG. 1 and the text. All strains are rec12Δ and transmission of chromosome 3 was followed using heterozygous markers at the ade6 locus (columns 3 and 5). hphMX4 confers resistance to hygromycin (HygR). The number of viable progeny inheriting one or both ade6 markers is indicated (columns 6-8), as are the percentage of the progeny that inherited both markers (column 10). These strains have two copies of chromosome 3, so we refer to them as disomes, although other homozygous disomes could be present in the Ade$^+$ Hyg$^S$ and Ade$^-$ Hyg$^R$ classes as well. Amongst the progeny that inherit only one ade6 marker, we show the percent that inherit allele 2 (column 12), which is the allele from the pure Sk chromosome. For the statistical analyses (G-tests), we compared the observed heterozygous disomy and allele 2 transmission to the values observed in diploid 10, which is a pure Sk rec12Δ control (columns 11 and 13). The last column indicates the number of independent diploids that were generated and assayed of each genotype.

FIG. 2A to FIG. 2B shows that Sk wtf4 is a self-sufficient meiotic driver that kills gametes that do not inherit the gene.

FIG. 2A shows allele transmission and propidium iodide (PI) staining phenotypes of diploids 11-19. Sk-derived DNA is purple, Sp-derived DNA is green. The cartoons depict chromosome 3. Chromosomes 1 and 2 are derived from Sk in diploids 11-15, but are from Sp in diploids 16-19. For diploids 11-15, allele transmission was monitored by following heterozygous markers at the ura4 locus, which is tightly linked to wtf4 (estimated 7-17 cM based on physical distance (45)). PI dye is excluded from living spores, but not dead spores that have lost membrane integrity, such as those destroyed by drive. The percent of spores that exclude PI is shown as a proxy of fertility (FIG. 2C). The PI phenotypes and ura4 locus allele transmission for diploids 11, 12, 14 and 15 were compared to those of the wild-type Sk control (diploid 13). * indicates p-value<0.01 (G-test). For diploids 16-19, allele transmission was followed using markers at the ade6 locus, which is where the empty vector or wtf gene constructs are integrated. The integrations introduced a dominant drug resistance gene and mutated ade6$^+$. Because these diploids all had codominant alleles at ade6, we could detect progeny that inherited both ade6 alleles (less than 10% of the total population). These progeny are excluded from the data presented above, but all the raw data are presented in FIG. 6. The PI phenotypes and allele transmission for diploids 17-19 were compared to the empty vector control (diploid 16) and * indicates p-value<0.01 (G-test). See FIG. 6 for the markers used for each diploid and the raw data for allele transmission and FIG. 7 for the PI staining raw data. Over 200 viable gametes were scored for allele transmission and over 200 spores (>50 4-spore asci) were assayed for PI staining. FIG. 2B shows images of PI staining and transmitted light (TL) in an ascus with no drive containing all alive spores (top) and in an ascus with drive where two of the four spores are dead (bottom). Scale bar represents 3 microns.

FIG. 2C shows that PI staining correlates with viable spore yield as a measure of fertility in wild-type and wtf heterozygous crosses. The fertility of the indicated diploids was assayed using both the established viable spore yield assay and by PI staining. We avoided tetrad dissection because we found that it was complicated by disintegration of spores destroyed by drive. The viable spore yield assay is a plating assay that measures the number of viable spores produced per viable diploid induced to undergo meiosis (32). PI is excluded from viable spores, but enters those destroyed by wtf drivers (FIG. 2B). Although PI staining likely will not detect spore death by other causes that do not disrupt membrane integrity, the percent of PI-excluding cells correlates with viable spore yield in wild-type and wtf heterozygous crosses. Diploids of four genotypes are shown. Three of the diploids are used elsewhere in the paper (diploids 17, 22, and 27) and the diploid number (column 1) corresponds to the diploid numbers used in the main text and figures. The two strains that were mated to generate the diploids are shown in columns 2 and 4. The drive-relevant genotypes of these parental strains is shown in columns 3 and 5. The last two columns show the PI-staining and viable spore yield phenotypes of each diploid.

FIG. 3A shows a model for meiotic drive of Sk wtf4 via a poison-antidote mechanism. FIG. 3B shows that Sk wtf4 creates a long and an alternative short transcript. See FIG. 3E for a depiction of the long-read RNA sequencing data on which this model is based (29). FIG. 3C shows Sk Wtf4-GFP localization in diploids where drive does (right panels) or does not occur (left panels). Cells were imaged prior to the first meiotic division (top) and as mature asci (bottom). FIG. 3D shows asci generated by diploids of the same genotypes as in FIG. 3C stained with PI to label dead cells (those lacking wtf4).

FIG. 4A to FIG. 4B shows that Sk wtf4 creates two proteins using alternate transcripts: an antidote and a gamete-killing poison. FIG. 4A shows separation of function wtf4 alleles. The red stars indicate start codon mutations. FIG. 4B shows allele transmission and PI staining phenotypes of Sp diploids with the indicated Sk wtf4 alleles integrated at ade6 on chromosome 3, as in diploids 16-19 in FIG. 2A. Spores that inherited both alleles at ade6 are eliminated from the data presented above, but the complete data are found in FIG. 6. * indicates p-value<0.01 (G-test) compared to empty vector (or wild-type control) for allele transmission and fertility as assayed by PI staining. See FIG. 6 for raw data and the markers used to monitor allele transmission for each diploid and FIG. 7 for the PI staining raw data. Over 200 viable gametes were scored for allele transmission for all diploids except diploid 24, from which we genotyped 50. Over 200 spores (>50 4-spore asci) were assayed for PI staining of each diploid.

FIG. 5A to FIG. 5D shows that wtf4 antidote is spore-specific and Wtf4 poison spreads throughout the ascus. FIG. 5A shows constructs tagging either the Wtf4 antidote (top) or poison (bottom) proteins. The red stars indicate start codon mutations. FIG. 5B shows allele transmission and fertility (as assayed by PI staining) for tagged alleles. See FIG. 6 for raw data and the markers used to monitor allele transmission for each diploid and FIG. 7 for the PI staining raw data. PI to assay fertility of mCherry tagged strains could not be reliably used, but in viable spore yield assays the mCherry$^{antidote}$-wtf4 allele gave a similar phenotype to wtf4 (29). * indicates p-value<0.01 (G-test) compared to empty vector (or wild-type control). FIG. 5C shows Wtf4 poison (cyan) and antidote (magenta) protein localization prior to the first meiotic division (left panels) and in a mature ascus (right panels). Scale bar represents 3 microns. FIG. 5D shows that spectral unmixing verifies true signal. FIG. 5D shows wtf4 poison (cyan) and antidote (magenta) protein localization in a mature ascus processed using linear unmixing (top panels) and unprocessed (bottom panels). Scale bar represents 3 microns.

FIG. 6 shows the raw data and markers used to monitor allele transmission for each diploid.

FIG. 7 shows the PI staining raw data.

DETAILED DESCRIPTION OF THE INVENTION

Figure 1A:
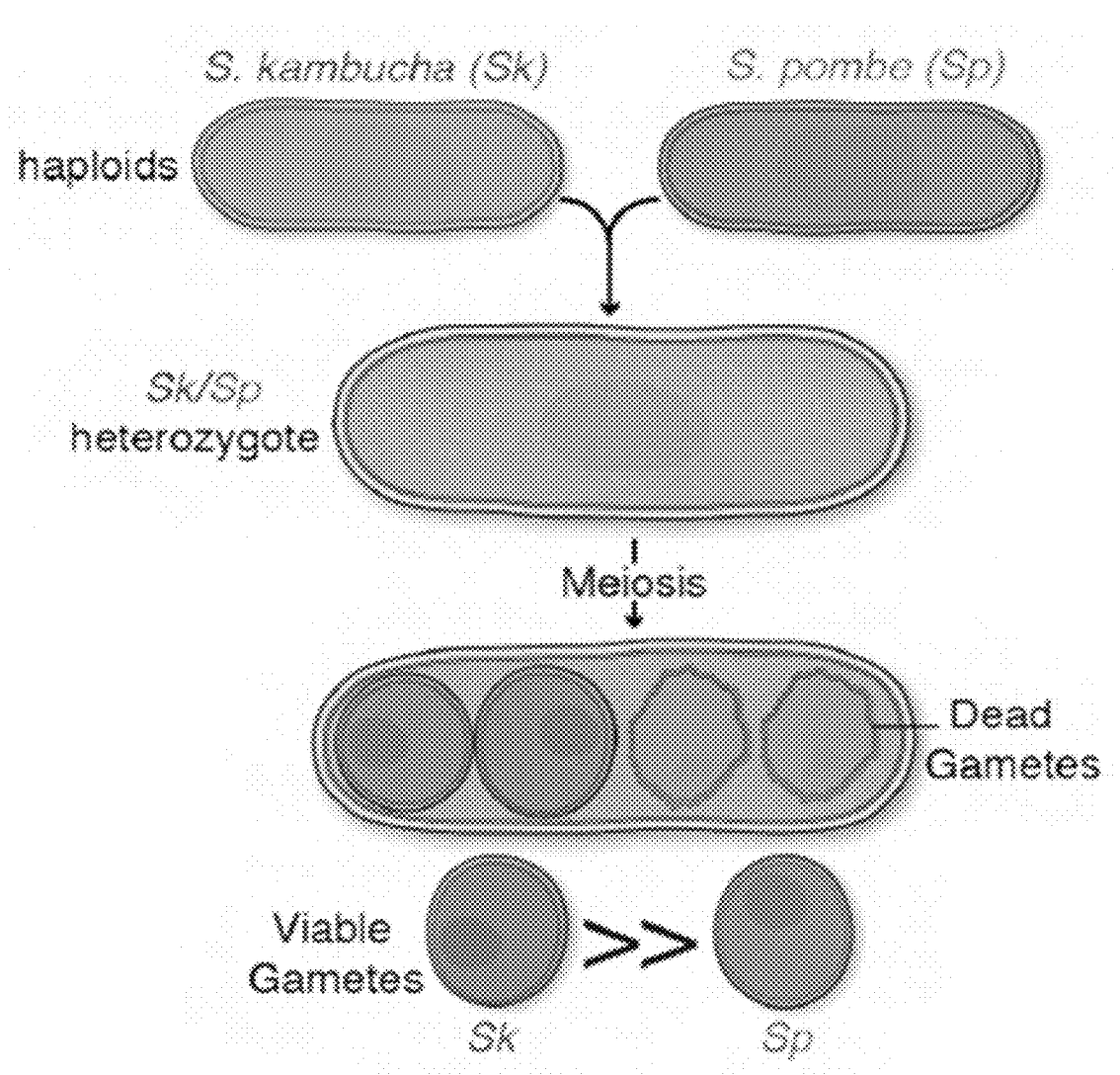

The present disclosure provides a meiotic drive composition comprising a recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; wherein the first peptide sequence and the second peptide sequence are derived from alternative transcriptional start sites on the recombinant DNA sequence; and wherein the recombinant DNA sequence, when expressed in a diploid organism, is effective to bias offspring toward having the recombinant DNA.

As used herein, the term "recombinant DNA sequence" means a DNA molecule formed through recombination methods to splice fragments of DNA from a different source or from different parts of the same source. For example, in some embodiments, two or more different sources of DNA are cleaved using restriction enzymes and joined together using ligases.

As used herein, the term "destroying a gamete" and grammatical versions thereof means killing a gamete, preventing a gamete from uniting with another haploid cell, or preventing or reducing viability of a zygote arising from a gamete. As used herein, the term "rescuing a gamete" and grammatical versions thereof means preventing one or more agents from destroying a gamete or increasing the viability of a gamete relative to a non-rescued gamete.

As used herein, the term "transport outside of a cell" and grammatical versions thereof means any form of movement from the interior of a cell (or subcellular compartment) to the outside of the cell. The forms of transport outside of a cell include, but are not limited to, active transport, passive transport, and transport through one or more of endoplasmic reticulum, golgi, endosome, and secretory vesicles. In some embodiment, some or all of a protein translated inside of a cell may be transported outside of a cell. For example, in some embodiments, some or all of a peptide sequence may move from the interior of a cell to the outside of the cell (e.g. released into intercellular space or tethered to the outer membrane) where the peptide sequence may contact other cells.

As used herein, the terms "polypeptide," "peptide," and "protein" are used interchangeably herein to refer to a polymer of amino acid residues. The term "peptide sequence" refers to the sequence of amino acid residues comprising the peptide. In some embodiments, the peptide sequence is encoded by one or more nucleic acids. "Nucleic acid" as used herein means at least two nucleotides covalently linked together. Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

As used herein, the term "alternative transcriptional start site," and grammatical versions thereof, means that there is more than one location where transcription starts at the 5' end of a nucleotide sequence. In some embodiments, the alternative transcription start sites result in distinct translation start sites to produce alternative isoforms of protein sequences. In some embodiments, the alternative transcripts encode distinct meiotic drive components. For example, in some embodiments, the alternative transcripts of Sk wtf 4 or Sp wtf 4 genes encode the two meiotic drive components of a poison peptide sequence (capable of destroying a gamete) and an antidote peptide sequence (capable of rescuing a gamete). In some embodiments, the alternative transcriptional start site is an alternative first exon transcriptional start site or an alternative tandem transcriptional start site.

According to some embodiments, a meiotic drive composition comprises a recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; and wherein the recombinant DNA sequence, when expressed in a diploid organism, is effective to bias offspring toward having the recombinant DNA.

According to some embodiments, a meiotic drive composition comprises a recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence and the second peptide sequence are derived from alternative transcriptional start sites on the recombinant DNA sequence; and wherein the recombinant DNA sequence, when expressed in a diploid organism, is effective to bias offspring toward having the recombinant DNA.

According to some embodiments, the recombinant DNA sequence does not naturally occur in the diploid organism. As used herein, the term "does not naturally occur" and grammatical versions thereof means that the recombinant DNA sequence is not present in the endogenous genomic DNA sequence of the organism or comprises at least one nucleotide substitution relative to the endogenous genomic DNA sequence. In some embodiments, the organism is selected from any vertebrate or invertebrate animal, including but not limited to, rodents, fleas, mosquitos, worms, ticks, lice, and flies, among many others.

According to some embodiments, the recombinant DNA sequence is adapted to integrate into the genome of a diploid organism. As used herein, the term "integrate into the genome" and grammatical versions thereof means to combine a DNA sequence with the whole of a chromosome or genome. The term includes, without limitation, site specific integration, random integration, reversible integration, or irreversible integration.

In some embodiments, the first and second peptide sequence may be encoded by any meiotic drive gene that, when expressed in a diploid organism, is capable of biasing offspring of such organism to express such gene and other genes that may be operatively linked to such genes. For example, the first peptide sequence may be SEQ ID NOs.: 1 and/or 3 or orthologs thereof. And, for example, the second peptide sequence may be SEQ ID NOs.: 2 and/or 4 or orthologs thereof. In addition, according to some embodiments, the first peptide sequence has at least 70% identity to SEQ ID NO: 1. According to some embodiments, the first peptide sequence has at least 80% identity to SEQ ID NO: 1. According to some embodiments, the first peptide sequence has at least 90% identity to SEQ ID NO: 1. According to some embodiments, the second peptide sequence has at least 70% identity to SEQ ID NO: 2. According to some embodiments, the second peptide sequence has at least 80% identity to SEQ ID NO: 2. According to some embodiments, the second peptide sequence has at least 90% identity to SEQ ID NO: 2.

According to some embodiments, the first peptide sequence has at least 70% identity to SEQ ID NO: 3. According to some embodiments, the first peptide sequence has at least 80% identity to SEQ ID NO: 3. According to some embodiments, the first peptide sequence has at least 90% identity to SEQ ID NO: 3. According to some embodiments, the second peptide sequence has at least 70% identity to SEQ ID NO: 4. According to some embodiments, the second peptide sequence has at least 80% identity to SEQ ID NO: 4. According to some embodiments, the second peptide sequence has at least 90% identity to SEQ ID NO: 4.

As used herein, the term "identity" and grammatical versions thereof means the extent to which two nucleotide or amino acid sequences have the same residues at the same positions in an alignment. Percent (%) identity is calculated by multiplying the number of matches in a sequence alignment by 100 and dividing by the length of the aligned region, including internal gaps. In some embodiments, one or more peptides have at least 70, 80, 90, 95, 96, 97, 98, or 99% identity to one or more of SEQ ID NOs: 1-4.

In some embodiments, the first and/or second peptides comprise structural features, such as transmembrane helices. In some embodiments, SEQ ID NO: 1 comprises transmembrane helices between one or more of the following amino acid ranges: 41-63, 78-97, 110-129, 133-150, 162-184, and 194-216. In some embodiments, SEQ ID NO: 2 comprises transmembrane helices between one or more of the following amino acid ranges: 83-105, 120-139, 152-171, 175-192, 204-226, and 236-258. In some embodiments, SEQ ID NO: 3 comprises transmembrane helices between one or more of the following amino acid ranges: 53-75, 90-111, 118-140, 176-195, 208-230, 235-257, and 303-325. In some embodiments, SEQ ID NO: 4 comprises transmembrane helices between one or more of the following amino acid ranges: 108-130, 145-166, 173-195, 231-250, 263-285, 290-312, and 358-380.

In some embodiments, the first peptide sequence comprises the short form of the wtf 4 protein, which is capable of destroying a gamete. In some embodiments, the second peptide sequence comprises the long form of the wtf 4 protein, which is capable of rescuing a gamete from the first (short form) of the wtf4 protein.

In some embodiments, the recombinant DNA sequence encodes the first and second peptide sequences as distinct genes having separate regulatory sequences (e.g. promoter, enhancer, terminator) and separate open reading frame (e.g. protein coding region and intron). In some embodiments, the regulatory sequences of the distinct genes comprises one or more of a constitutive promoter, tissue-specific promoter, developmental stage-specific promoter, inducible promoter, or a synthetic promoter. In some embodiments, the promoter is selected for expression of the first and second peptide sequence in a specific organism. In some embodiments, Eukaryotic promoters include, but are not limited to, one or more of CMV, EF 1a, SV40, PGK1, CAG, TRE, UAS, Ac5, and Polyhedrin.

In some embodiments, the recombinant DNA sequence encodes the first and second peptide sequence as a single gene that results in more than one protein product. For example, in some embodiments, the recombinant DNA sequence is continuously transcribed but produces the first and second peptides as distinct proteins. In some embodiments, the recombinant DNA sequence comprises an internal ribosomal entry site (IRES), which results in more than one protein product from a single transcript.

The present disclosure also provides a vector or analogous construct comprising the recombinant DNA sequences described above and heterologous DNA sequences. As used herein, the term "heterologous DNA sequences" and grammatical versions thereof means a sequence of DNA that does not naturally occur in the context in which it is present. For example, a vector may comprise DNA sequences from one or more organisms that do not naturally occur together. Those sequences may comprise, without limitation, promoters, ribosomal binding sites, start codons, termination codons, and transcription termination sequences from one or more organisms.

The present disclosure also provides a method of propagating a recombinant DNA sequence in a diploid organism's offspring comprising the steps of expressing the recombinant DNA sequence in the diploid organism, wherein the DNA sequence encodes a first peptide sequence and a second peptide sequence, the first peptide sequence capable of destroying a gamete of the organism and the second peptide sequence capable of rescuing a gamete of the organism from the first peptide sequence; wherein the first peptide sequence is transported outside of a cell and the second peptide sequence is not transported outside of a cell; wherein the first peptide sequence and the second peptide sequence are derived from alternative transcriptional start sites on the recombinant DNA sequence; and wherein the recombinant DNA sequence, when expressed in a diploid organism, is effective to bias offspring toward having the recombinant DNA sequence; and permitting reproduction of the organism.

As used herein, the term "propagating a recombinant DNA sequence in a diploid organism's offspring" and grammatical versions thereof means that the recombinant DNA sequence is caused to be over represented in the gametes which are formed, which results in over representation (e.g., higher than expected according to Mendelian genetics) of the recombinant DNA sequence in the next generation of the organism. In this manner, the recombinant DNA sequences are able to spread through a population of an organism during reproduction.

According to some embodiments, a method of propagating a recombinant DNA sequence in a diploid organism's offspring comprises the steps of expressing the recombinant DNA sequence in the diploid organism, wherein the DNA sequence encodes a first peptide sequence and a second peptide sequence, the first peptide sequence capable of destroying a gamete of the organism and the second peptide sequence capable of rescuing a gamete of the organism from the first peptide sequence; wherein the first peptide sequence is transported outside of a cell and the second peptide sequence is not transported outside of a cell; and wherein the recombinant DNA sequence, when expressed in a diploid organism, is effective to bias offspring toward having the recombinant DNA sequence; and permitting reproduction of the organism.

According to some embodiments, a method of propagating a recombinant DNA sequence in a diploid organism's offspring comprises the steps of expressing the recombinant DNA sequence in the diploid organism, wherein the DNA sequence encodes a first peptide sequence and a second peptide sequence, the first peptide sequence capable of destroying a gamete of the organism and the second peptide sequence capable of rescuing a gamete of the organism from the first peptide sequence; wherein the first peptide sequence and the second peptide sequence are derived from alternative transcriptional start sites on the recombinant DNA sequence; and wherein the recombinant DNA sequence, when expressed in a diploid organism, is effective to bias offspring toward having the recombinant DNA sequence; and permitting reproduction of the organism.

According to some embodiments, the recombinant DNA sequence does not naturally occur in the diploid organism. According to some embodiments, the recombinant DNA sequence is adapted to integrate into the genome of the diploid organism.

In some embodiments, the first and second peptide sequence may be encoded by any meiotic drive gene that, when expressed in a diploid organism, is capable of biasing offspring of such organism to express such gene and other genes that may be operatively linked to such genes. For example, the first peptide sequence may be SEQ ID NOs.: 1 and/or 3 or orthologs thereof. And, for example, the second peptide sequence may be SEQ ID NOs.: 2 and/or 4 or orthologs thereof. In addition, according to some embodiments, the first peptide sequence has at least 70% identity to SEQ ID NO: 1. According to some embodiments, the first peptide sequence has at least 80% identity to SEQ ID NO: 1. According to some embodiments, the first peptide sequence has at least 90% identity to SEQ ID NO: 1. According to some embodiments, the second peptide sequence has at least 70% identity to SEQ ID NO: 2. According to some embodiments, the second peptide sequence has at least 80% identity to SEQ ID NO: 2. According to some embodiments, the second peptide sequence has at least 90% identity to SEQ ID NO: 2.

According to some embodiments, the first peptide sequence has at least 70% identity to SEQ ID NO: 3. According to some embodiments, the first peptide sequence has at least 80% identity to SEQ ID NO: 3. According to some embodiments, the first peptide sequence has at least 90% identity to SEQ ID NO: 3. According to some embodiments, the second peptide sequence has at least 70% identity to SEQ ID NO: 4. According to some embodiments, the second peptide sequence has at least 80% identity to SEQ ID NO: 4. According to some embodiments, the second peptide sequence has at least 90% identity to SEQ ID NO: 4.

The present disclosure also provides a meiotic drive composition comprising a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; wherein the first peptide sequence and the second peptide sequence are derived from alternative transcriptional start sites on the first recombinant DNA sequence; and a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence.

The term "operably linked" refers to the association of nucleic acid sequences on a single nucleic acid fragment so that the function of one is regulated by the other or is not hindered by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, two proteins can be operably linked, such that the function of either protein is not compromised. Generally, operably linked means that the nucleic acid sequences being linked are contiguous and, where necessary to join two protein coding regions, contiguous and in the same reading frame. In addition, the term "operatively linked" and grammatical versions thereof means that two or more sequences are inherited together more than 50% of the time. For example, two or more DNA sequences may be located in close proximity to one another on a chromosome such that it is unlikely the two sequences will be separated during the process of homologous recombination. In this regard, according to some embodiments, two or more DNA sequences are inherited together more than 60% of the time. According to some embodiments, two or more DNA sequences are inherited together more than 70% of the time. According to some embodiments, two or more DNA sequences are inherited together more than 80% of the time. According to some embodiments, two or more DNA sequences are inherited together more than 90% of the time.

As used herein, the term "gene of interest" and grammatical versions thereof includes, without limitation, genetic tags, selection genes (e.g. anti-biotic resistance genes), or any other, gene or nucleotide sequence or fragment thereof, that confers a desired phenotype. The gene of interest may be from the same or different organism as the first DNA sequence or may be a synthetic construct. In some embodiments, the gene of interest is a gene that confers infertility to an animal that carries one or more copies. In some embodiments, the gene of interest is effective to cause a crash in the population of a disease vector (e.g. mosquitos) by reducing the population's reproductive capacity.

According to some embodiments, a meiotic drive composition comprises a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; and a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence.

According to some embodiments, a meiotic drive composition comprises a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence and the second peptide sequence are derived from alternative transcriptional start sites on the first recombinant DNA sequence; and a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence.

According to some embodiments, the first recombinant DNA sequence does not naturally occur in the diploid organism. According to some embodiments, the second recombinant DNA sequence does not naturally occur in the diploid organism.

According to some embodiments, the first recombinant DNA sequence and/or second recombinant DNA sequence is adapted to integrate into the genome of the diploid organism.

The present disclosure also provides a vector or analogous construct comprising the first recombinant DNA sequence and/or second recombinant DNA sequence as described above and one or more heterologous DNA sequences.

According to some embodiments, the second recombinant DNA sequence may be linked to the first recombinant DNA sequence via proximity of the first and second recombinant DNA sequences on a chromosome.

According to some embodiments, the second recombinant DNA sequence may be adjacent to the first recombinant DNA sequence and there is continuous transcription of the first and second recombinant DNA sequences.

As used herein, the term "continuous transcription" of recombinant DNA sequences and grammatical versions thereof means that the recombinant DNA sequences are organized into a single transcriptional unit and are transcribed into a continuous transcript. According to some embodiments, the continuous transcript is translated into a continuous amino acid sequence. According to some embodiments, the continuous transcript is translated into two or more amino acid sequences. For example, in some embodiments, an adjacent DNA sequence comprises an internal ribosomal entry site (IRES), resulting in production of two or more proteins from a single transcript.

In some embodiments, the first and second peptide sequence may be encoded by any meiotic drive gene that, when expressed in a diploid organism, is capable of biasing offspring of such organism to express such gene and other genes that may be operatively linked to such genes. For example, the first peptide sequence may be SEQ ID NOs.: 1 and/or 3 or orthologs thereof. And, for example, the second peptide sequence may be SEQ ID NOs.: 2 and/or 4 or orthologs thereof. In addition, according to some embodiments, the first peptide sequence has at least 70% identity to SEQ ID NO: 1. According to some embodiments, the first peptide sequence has at least 80% identity to SEQ ID NO: 1. According to some embodiments, the first peptide sequence has at least 90% identity to SEQ ID NO: 1. According to some embodiments, the second peptide sequence has at least 70% identity to SEQ ID NO: 2. According to some embodiments, the second peptide sequence has at least 80% identity to SEQ ID NO: 2. According to some embodiments, the second peptide sequence has at least 90% identity to SEQ ID NO: 2.

According to some embodiments, the first peptide sequence has at least 70% identity to SEQ ID NO: 3. According to some embodiments, the first peptide sequence has at least 80% identity to SEQ ID NO: 3. According to some embodiments, the first peptide sequence has at least 90% identity to SEQ ID NO: 3. According to some embodiments, the second peptide sequence has at least 70% identity to SEQ ID NO: 4. According to some embodiments, the second peptide sequence has at least 80% identity to SEQ ID NO: 4. According to some embodiments, the second peptide sequence has at least 90% identity to SEQ ID NO: 4.

The present disclosure also provides a method of propagating one or more recombinant DNA sequences in a diploid organism's offspring comprising the steps of (i) expressing in the organism a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; wherein the first peptide sequence and the second peptide sequence are derived from alternative transcriptional start sites on the first recombinant DNA sequence; (ii) expressing in the organism a second recombinant DNA sequence linked to the first recombinant DNA sequence, wherein the second recombinant DNA sequence encodes a gene of interest; and (iii) permitting reproduction of the organism; wherein the first recombinant DNA sequence, when expressed in the organism, is effective to bias offspring toward having both the first recombinant DNA sequence and the second recombinant DNA sequence.

According to some embodiments, a method of propagating one or more recombinant DNA sequences in a diploid organism's offspring comprises the steps of: (i) expressing in the organism a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence and the second peptide sequence are derived from alternative transcriptional start sites on the first recombinant DNA sequence; and (ii) expressing in the organism a second recombinant DNA sequence operably linked to the first recombinant DNA sequence, wherein the second recombinant DNA sequence encodes a gene of interest; and (iii) permitting reproduction of the organism; wherein the first recombinant DNA sequence, when expressed in the organism, is effective to bias offspring toward having both the first recombinant DNA sequence and the second recombinant DNA sequence.

According to some embodiments, a method of propagating one or more recombinant DNA sequences in a diploid organism's offspring comprising the steps of: (i) expressing in the organism a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; (ii) expressing in the organism a second recombinant DNA sequence operably linked to the first recombinant DNA sequence, wherein the second recombinant DNA sequence encodes a gene of interest; and (iii) permitting reproduction of the organism; wherein the first recombinant DNA sequence, when expressed in the organism, is effective to bias offspring toward having both the first recombinant DNA sequence and the second recombinant DNA sequence.

According to some embodiments, the first recombinant DNA sequence does not naturally occur in the diploid organism. According to some embodiments, the second recombinant DNA sequence does not naturally occur in the diploid organism.

According to some embodiments, the first recombinant DNA sequence and/or second recombinant DNA sequence is adapted to integrate into the genome of the diploid organism.

According to some embodiments, the second recombinant DNA sequence is operably linked to the first recombinant DNA sequence via, e.g., proximity of the first and second recombinant DNA sequences on a chromosome. According to some embodiments, the second recombinant DNA sequence is, e.g., adjacent to the first recombinant DNA sequence and there is continuous transcription of the first and second recombinant DNA sequences.

In some embodiments, the first and second peptide sequence may be encoded by any meiotic drive gene that, when expressed in a diploid organism, is capable of biasing offspring of such organism to express such gene and other genes that may be operatively linked to such genes. For example, the first peptide sequence may be SEQ ID NOs.: 1 and/or 3 or orthologs thereof. And, for example, the second peptide sequence may be SEQ ID NOs.: 2 and/or 4 or orthologs thereof. In addition, according to some embodiments, the first peptide sequence has at least 70% identity to SEQ ID NO: 1. According to some embodiments, the first peptide sequence has at least 80% identity to SEQ ID NO: 1. According to some embodiments, the first peptide sequence has at least 90% identity to SEQ ID NO: 1. According to some embodiments, the second peptide sequence has at least 70% identity to SEQ ID NO: 2. According to some embodiments, the second peptide sequence has at least 80% identity to SEQ ID NO: 2. According to some embodiments, the second peptide sequence has at least 90% identity to SEQ ID NO: 2.

According to some embodiments, the first peptide sequence has at least 70% identity to SEQ ID NO: 3. According to some embodiments, the first peptide sequence has at least 80% identity to SEQ ID NO: 3. According to some embodiments, the first peptide sequence has at least 90% identity to SEQ ID NO: 3. According to some embodiments, the second peptide sequence has at least 70% identity to SEQ ID NO: 4. According to some embodiments, the second peptide sequence has at least 80% identity to SEQ ID NO: 4. According to some embodiments, the second peptide sequence has at least 90% identity to SEQ ID NO: 4.

The present disclosure also provides a kit comprising: (1) a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; wherein the first peptide sequence and the second peptide sequence are derived from alternative transcriptional start sites on the first recombinant DNA sequence; (2) a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence; and (3) reagents for expressing the first recombinant DNA sequence and/or the second recombinant DNA sequence in the diploid organism.

In addition to the above components, the subject kits will further include instructions for use of the components and/or practicing the subject methods. These instructions may be present in the subject kits in a variety of forms, one or more of which may be present in the kit. One form in which these instructions may be present is as printed information on a suitable medium or substrate, such as a piece or pieces of paper on which the information is printed, in the packaging of the kit, or in a package insert. Yet another means would be a computer readable medium, such as diskette, or CD, on which the information has been recorded. Further, another means by which the instructions may be present is a website address used via the internet to access the information at a removed site. Any convenient means may be present in the kits.

The components of the kits may be packaged either in aqueous media or in lyophilized form. The kits will generally be packaged to include at least one vial, test tube, flask, bottle, syringe or other container means, into which the described reagents may be placed, and preferably, suitably aliquoted. Where additional components are provided, the kit will also generally contain a second, third or other additional container into which such component may be placed.

The kits of the present disclosure will also typically include a means for containing the reagent containers in close confinement for commercial sale. Such containers may include injection or blow-molded plastic containers into which the desired vials are retained.

According to some embodiments, a kit comprises: (1) a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence and the second peptide sequence are derived from alternative transcriptional start sites on the first recombinant DNA sequence; (2) a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence; (3) reagents for expressing the first recombinant DNA sequence and/or the second recombinant DNA sequence in the diploid organism.

According to some embodiments, a kit comprises: (1) a first recombinant DNA sequence encoding a first peptide sequence and a second peptide sequence, the first peptide sequence capable of destroying a gamete and the second peptide sequence capable of rescuing a gamete from the first peptide sequence; wherein the first peptide sequence is transported outside of a cell and the second peptide sequence is not transported outside of a cell; (2) a second recombinant DNA sequence operably linked to the first recombinant DNA sequence, wherein the second recombinant DNA sequence encodes a gene of interest; wherein the first recombinant DNA sequence, when expressed in a diploid organism, is effective to bias offspring toward having both the first recombinant DNA sequence and the second recombinant DNA sequence; and (3) reagents for expressing the first recombinant DNA sequence and/or the second recombinant DNA sequence in the diploid organism.

In some embodiments, the first and second peptide sequence may be encoded by any meiotic drive gene that, when expressed in a diploid organism, is capable of biasing offspring of such organism to express such gene and other genes that may be operatively linked to such genes. For example, the first peptide sequence may be SEQ ID NOs.: 1 and/or 3 or orthologs thereof. And, for example, the second peptide sequence may be SEQ ID NOs.: 2 and/or 4 or orthologs thereof. In addition, according to some embodiments, the first peptide sequence has at least 70% identity to SEQ ID NO:1 or SEQ ID NO: 3. According to some embodiments, the first peptide sequence has at least 80% identity to SEQ ID NO:1 or SEQ ID NO: 3. According to some embodiments, the first peptide sequence has at least 90% identity to SEQ ID NO:1 or SEQ ID NO: 3. According to some embodiments, the first peptide sequence has at least 70% identity to SEQ ID NO:2 or SEQ ID NO: 4. According to some embodiments, the first peptide sequence has at least 80% identity to SEQ ID NO: 2 or SEQ ID NO: 4. According to some embodiments, the first peptide sequence has at least 90% identity to SEQ ID NO: 2 or SEQ ID NO: 4.

| SEQ ID NO: | Amino Acid Sequence |
|---|---|
| SEQ ID NO: 1 | MLSEIWKYIKTVSEDSSTGPTETTNPNVERRQEFKDSHPNIYSLLRL<br>LISVLAVIVVFFTAWVCVNPLEKSIFGKVAFFVTIGITCPILLITIFCFF<br>ETWTQAVAQCIKVTVIFLAQCVKVTAVGLYNSREKWVVIIWLLWV<br>VICYTLFLRSKFGNLNLNKALICSTCSISAALLLFLLYVRLPFWTLKH<br>MFSGLFQVLGVQSCVVIVTKGLTYLFDKHIDATGYEIEASSLFVIGN<br>FLFFYEMECPGALKRMPKFIRNGIASFLEGIGNIGRAFRGANDNNDI<br>PLGEMEVESEV |
| SEQ ID NO: 2 | MKNKDYPLRSSMDELSTKNDNEIDLEKGPLPEYNSEDESTLPPYSEI<br>WKYIKTVSEDSSTGPTETTNPNVERRQEFKDSHPNIYSLLRLLISVL<br>AVIVVFFTAWVCVNPLEKSIFGKVAFFVTIGITCPILLITIFCFFETWT<br>QAVAQCIKVTVIFLAQCVKVTAVGLYNSREKWVVIIWLLWVVICY<br>TLFLRSKFGNLNLNKALICSTCSISAALLLFLLYVRLPFWTLKHMFS<br>GLFQVLGVQSCVVIVTKGLTYLFDKHIDATGYEIEASSLFVIGNFLF<br>FYEMECPGALKRMPKFIRNGIASFLEGIGNIGRAFRGANDNNDIPLG<br>EMEVESEV |
| SEQ ID NO: 3 | MGQNITKLFNWNKSTTPPDYDENRLPITDEGNNPPNTHRENHSSGT<br>ADNSSPFLIKLIISFTPIFVLNVPAVCYLTYKDALFKDYGKDEWVYF<br>GVWCAICLMSFISLWCFYETWTKAVKVTVIFLAQCVKVTVIFLAQC<br>VKVTAIFSAQCIKVTVISLAKCVKVIAVGLYNSKKDLVVTIWLAWV<br>VICFILFGCVKDGRLNLNKALICSTSSISAALFFILLLVCIPIWTLKHM<br>LFGLFQVLGVQSCVVIVTKGLMYLFDKHIDATGYEIEASSLFVIGNF<br>LFFYEMERPGALKRMPKFIRNGIASFLGGIANAFGGIANAIRGANDN<br>NDIPLGEMEVESEV |
| SEQ ID NO: 4 | MKNKYYPLRSSMDELSTKNDNEIDLEKGPLPEYNSEDGNTLPPYSE<br>NINLKDPKQMGQNITKLFNWNKSTTPPDYDENRLPITDEGNNPPNT<br>HRENHSSGTADNSSPFLIKLIISFTPIFVLNVPAVCYLTYKDALFKDY<br>GKDEWVYFGVWCAICLMSFISLWCFYETWTKAVKVTVIFLAQCVK<br>VTVIFLAQCVKVTAIFSAQCIKVTVISLAKCVKVIAVGLYNSKKDLV<br>VTIWLAWVVICFILFGCVKDGRLNLNKALICSTSSISAALFFILLLVCI<br>PIWTLKHMLFGLFQVLGVQSCVVIVTKGLMYLFDKHIDATGYEIEA<br>SSLFVIGNFLFFYEMERPGALKRMPKFIRNGIASFLGGIANAFGGIAN<br>AIRGANDNNDIPLGEMEVESEV |

The present disclosure provides Sk wtf4 as an autonomous gamete-killing meiotic drive gene. Data show that Sk wtf4 generates two transcripts from alternate start sites: a long transcript encoding an antidote and a short transcript encoding a gamete-killing poison. Whereas the poison protein is found in all the gametes, the antidote protein is enriched only in the gametes encoding Sk wtf4, thereby ensuring that gametes that do not inherit the selfish allele are destroyed. This gene is a member of the large, rapidly evolving wtf gene family that has 25 members in Sp. The present disclosure provides that wtf4 is not the only driver amongst wtfs. According to some embodiments, a novel mechanism by which meiotic drivers can act is used to bias the meiotic driver alone or with one or more genes of interest into a population of an organism.

The terminology used herein is for the purpose of describing particular embodiments only and is not intended to be limiting. As used in the specification and the appended claims, the singular forms "a," "an," and "the" include plural referents unless the context clearly dictates otherwise.

The following examples are provided to further illustrate the methods of the present invention. These examples are illustrative only and are not intended to limit the scope of the invention in any way.

Example 1

Materials and Methods

Crosses

For the mapping crosses, fertility and meiotic drive assays, the crosses were carried out similar to the description in (18). This required making stable diploids, because many of the strains used are homothallic (h90) and their self-mating would generate many non-informative spores. Briefly, ~200 μL of overnight culture from each haploid parent were mixed in a microcentrifuge tube, spun down and plated on either SPA (1% glucose, 7.3 nM $KH_2PO_4$, vitamins, agar) or MEA (3% malt extract, agar) for 12-15 hours at room temperature to allow the cells to mate. No differences were observed in meiotic drive phenotypes for diploids generated on SPA vs. MEA. SPA was generally used, but for some matings there was more success isolating stable diploids from MEA. The mated cells were scraped off and spread on a medium to select heterozygous diploids (generally minimal yeast nitrogen base plates). Diploid colonies were grown overnight in 5 mL of rich YEL broth (0.5% yeast extract, 3% glucose, 250 mg/L of adenine, lysine, histidine, and uracil). A small amount of the cultures <100 μL were then plated onto SPA to induce sporulation, and a diluted sample plated onto YEA (same as YEL, but with agar). The colonies that grew on the YEA plate were screened via replica plating to diagnostic media to verify that the culture was comprised of heterozygous diploid cells. If not, the culture was not assayed further. After 3-7 days, the mixture of cells, asci, and spores from the SPA plates were scooped up, treated with glusulase and ethanol to kill vegetative cells and to release spores from asci and the spores were plated on YEA. The spore colonies were then phenotyped using standard approaches. For some control loci, heterozygosity in the diploid test described above could not be easily verified. For those loci heterozygosity of the parent diploid in the progeny was verified. If the parent diploid proved not to be heterozygous, the diploid was eliminated. For each cross, at least two independently created diploids were assayed. The number of progeny scored varied between experiments. To map Sk wtf4, at least 100 viable progeny per cross were assayed. To characterize Sk wtf4, at least 200 viable gametes per cross were assayed. The one exception was the Sk wtf4$^{poison}$/Sk wtf4$^{antidote}$ cross in which allele transmission by PCR and sequencing (described below) was used to assay. For that cross, 50 viable progeny were assayed. The raw data underlying the major crosses are presented in FIG. 6 and FIG. 7.

Figure 6:
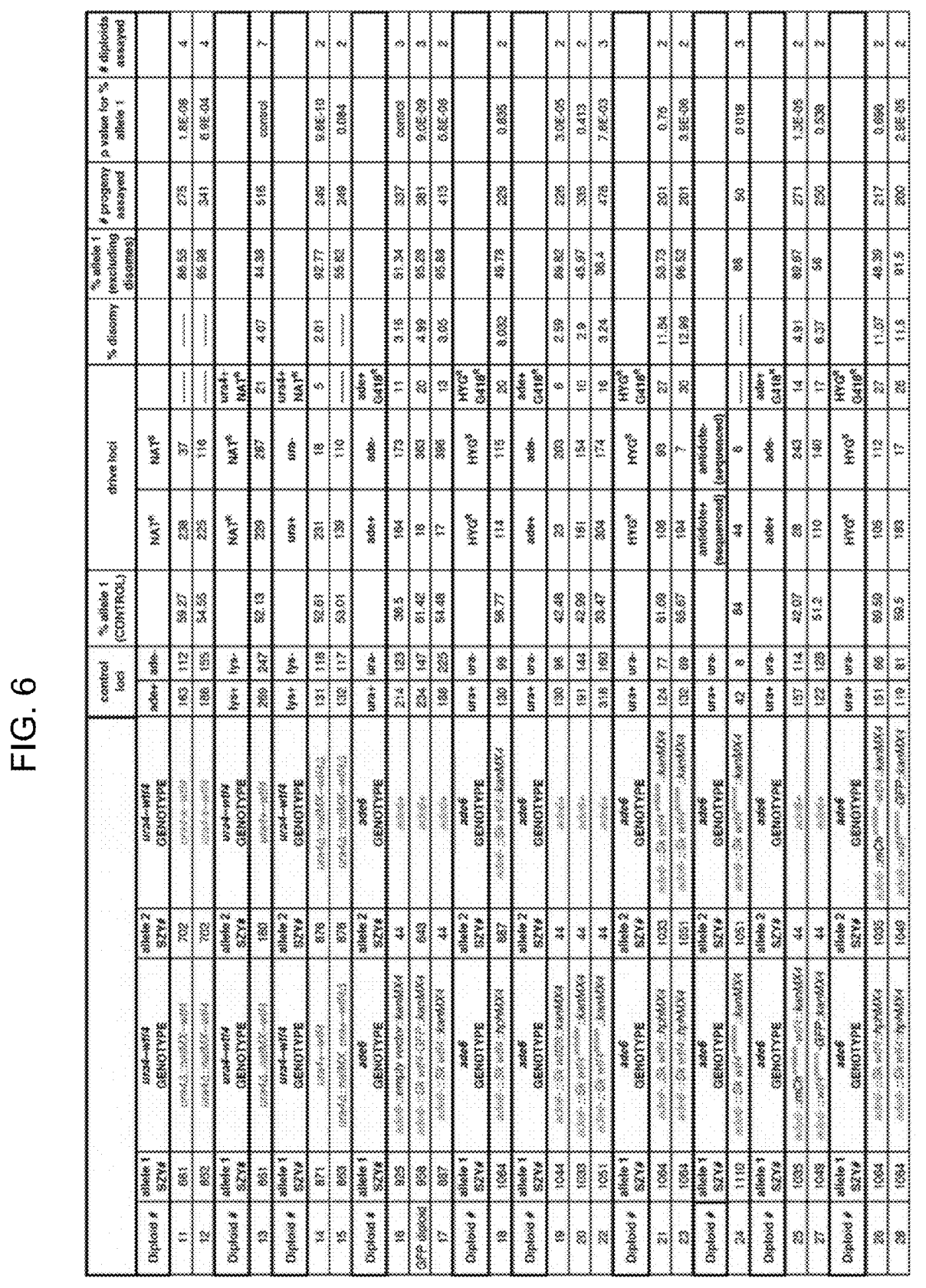

FIG. 6 shows raw data of allele transmission from FIGS. 2-5. Each horizontal entry represents the relevant genotype and allele transmission of the indicated diploids. The first column represents the diploid number, which matches the numbers shown in FIGS. 2-5. In columns 2-5, the two haploid parent strains (SZY #s) are indicated as are the alleles contributed by those parent strains at the experimental locus monitored for drive. Alleles derived from Sp are green whereas those from Sk are purple. For diploids 11-15, transmission of the wtf4 locus was followed using alleles of ura4, which is fortuitously closely linked to wtf4. Columns 9 and 10 indicate which phenotypes were followed at the drive loci and the number of progeny that displayed each phenotype. Some progeny inherited both alleles at a given drive locus and when the markers were codominant we could detect those disomes. The number of those disomes, which are likely heterozygous diploids or aneuploids, are shown in column 11 and their overall frequency is shown in column 12. If we did not have codominant markers, columns 11 and 12 are filled with ---. Column 13 is a measure of meiotic drive. It shows the fraction of the non-disomic progeny that inherited allele 1 (column 3). Column 14 shows the total number of progeny assayed for each diploid and column 15 is the p value calculated from a G-test comparing the allele transmission of allele 1 to a control. Diploid 13 served as the control for diploids 11, 12, 14 and 15. Diploid 16 served as the control for the rest of the diploids. Columns 6-8 are internal controls for each diploid. These controls represent an additional heterozygous locus unlinked to the meiotic drive locus that should undergo Mendelian allele transmission. The lys locus is lys4, the ade locus is ade6, and the ura locus is ura4. The final column indicates the number of independently generated diploids that were tested for each genotype. FIG. 7 shows raw data for PI-staining phenotypes from FIGS. 2-5. Each horizontal entry represents the relevant genotype and allele transmission of the indicated diploids. The first column represents the diploid number, which matches the numbers shown in FIGS. 2-5. In columns 2-5, the two haploid parent strains (SZY #s) are indicated as are the alleles contributed by those parent strains at the experimental locus monitored for drive. Alleles derived from Sp are green whereas those from Sk are purple. Columns 6 and 7 indicate the number of spores that stained with PI (dead spores) and those that did not (likely living spores) and column 8 shows the percentage of spores that did not stain with PI. Column 9 shows the number of stained asci that were scored for each diploid type. Spores not contained within 4-spore asci were not scored. Column 10 shows the p value from a G test comparing the number of stained and unstained spores for each diploid to a control diploid. Diploid 13 served as a control for diploids 11, 12, 14 and 15. Diploid 16 served as a control for all other diploids. The number of independently generated diploid strains that were tested is indicated in the last column.

Mapping the Sk Wtf4 Region

All strains used and their genotypes can be found in Table III. Table III shows the various yeast strains. The ura4-X allele (e.g. SZY382) listed in the table is either ura4-D18 or ura4-294. The wtf4Δ::kanMX4 (truncated drug S) allele is described in the methods. It does not confer resistance to G418. The precise location of the ura4$^+$ allele in strain SZY863 is unknown. It is not at the endogenous locus, although it is closely linked to the endogenous locus. The ade6-::gene1::gene2::ade6-allele naming structure is used in many strains. This indicates that a plasmid derived from pSZB188 bearing two genes (e.g. wtf4 and kanMX4) was integrated into the ade6$^+$ locus. This recombination event generates two mutant copies of ade6 flanking the contents of the plasmid. The Sk wtf4(357A>T, 358T>A, 359G>C) nomenclature denotes that the ATG sequence beginning at position 357 of the wtf4 gene has been changed to TAC. This is the ATG within what is intron 1 of the antidote that used as the start codon for the poison transcript. The Sk wtf4 (M1X,M12X) nomenclature denotes that the first two methionines in the antidote coding sequence have been mutated to stop codons (TAG).

TABLE III

| Strain | Species | Genotype |
|---|---|---|
| SZY44 | Sp | h-, lys4-95 |
| SZY120 | Sk | h90, rec12Δ::ura4+, ura4Δ::kanMX4 |
| SZY80 | Sk | h90, lys1Δ::kanMX4 |
| SZY192 | Sk | h90, rec12Δ::ura4+, ura4Δ::kanMX4, his5Δ::natMX4MX4 |
| SZY196 | Sk | h90, rec12Δ::ura4+, ura4Δ::kanMX4, lys1Δ::kanMX4 |
| SZY201 | Sp | h-, lys1-37, rec12-171::ura4+, ura4-x |
| SZY208 | Sk | h90, rec12Δ::ura4 , ade6Δ::hphMX4, his5Δ::natMX4, ura4Δ::kanMX4 |
| SZY210 | Sk | h90, ade6Δ::hphMX4, his5Δ::natMX4, ura4Δ::kanMX4 |
| SZY239 | hybrid with Sk karyotype | h-, rec12Δ::ura4+, ade6Δ::hphMX4, ura4Δ::kanMX4, |
| SZY247 | hybrid with Sk karyotype | h?, rec12Δ::ura4 , lys1-37, his5Δ::natMX4, ura4-x, |
| SZY320 | Sk | h90, ura4Δ::natMX4 |
| SZY382 | hybrid with Sk karyotype | h-, rec12Δ::ura4 , lys1-37, ura4-x |

TABLE III-continued

| Strain | Species | Genotype |
| --- | --- | --- |
| SZY547 | hybrid with Sk karyotype | h-, rec12Δ::ura4 , lys1-37, ura4-x, arg12Δ:hphMX4 |
| SZY558 | hybrid with Sk karyotype | h90, rec12Δ::ura4 , his5Δ::natMX4, ura4-x, arg12Δ::natMX4 |
| SZY562 | hybrid with Sk karyotype | hybrid chr3, Sk chr1 and chr2. h90, rec12Δ::ura4+, his5Δ::natMX4, ura4-x, ade6Δ::hphMX4 |
| SZY563 | hybrid with Sk karyotype | hybrid chr3, Sk chr1 and chr2. h90, rec12Δ::ura4+, his5Δ::natMX4, ura4-x, ade6Δ::hphMX4 |
| SZY564 | hybrid with Sk karyotype | hybrid chr3, Sk chr1 and chr2. h90, rec12Δ::ura4+, his5Δ::natMX4, ura4-x, ade6Δ::hphMX4 |
| SZY565 | hybrid with Sk karyotype | hybrid chr3, Sk chr1 and chr2. h90, rec12Δ::ura4+, his5Δ::natMX4, ura4-x, ade6Δ::hphMX4 |
| SZY566 | hybrid with Sk karyotype | hybrid chr3, Sk chr1 and chr2. h90, rec12Δ::ura4+, his5Δ::natMX4, ura4-x, ade6Δ::hphMX4 |
| SZY567 | hybrid with Sk karyotype | hybrid chr3, Sk chr1 and chr2. h90, rec12Δ::ura4+, his5Δ::natMX4, ura4-x, ade6Δ::hphMX4 |
| SZY574 | hybrid with Sk karyotype | hybrid chr3, Sk chr1 and chr2. h90, rec12Δ::ura4+, his5Δ::natMX4, ura4-x, ade6Δ::hphMX4 |
| SZY581 | hybrid with Sk karyotype | hybrid chr3, Sk chr1 and chr2. h90, rec12Δ::ura4+, his5Δ::natMX4, ura4-x |
| SZY582 | hybrid with Sk karyotype | hybrid chr3, Sk chr1 and chr2. h90, rec12Δ::ura4+, his5Δ::natMX4, ura4-x |
| SZY589 | hybrid with Sk karyotype | hybrid chr3, Sk chr1 and chr2. h90, rec12Δ::ura4+, his5Δ::natMX4, ura4Δ::kanMX4 |
| SZY591 | hybrid with Sk karyotype | hybrid chr3, Sk chr1 and chr2. h90, rec12Δ::ura4+, his5Δ::natMX4, ura4Δ::kanMX4 |
| SZY643 | Sp | h90, leu1-32, ura4-D18 |
| SZY649 | hybrid with Sk karyotype | h90, rec12Δ::ura4+, ura4-x, ade6Δ::hphMX4 |
| SZY659 | hybrid with Sk karyotype | h90, rec12Δ::ura4+, ura4-x, ade6Δ::hphMX4, kanMX4@chr3 position 214,500 bp |
| SZY661 | Sk | h90, ura4Δ::natMX4, leu1Δ::hphMX4 |
| SZY679 | hybrid with Sk karyotype | ura4Δ::natMX4, kanMX4@chr3 position 214500 bp, ade6Δ::hphMX4, rec12Δ::ura4+ |
| SZY684 | hybrid with Sk karyotype | ura4Δ::natMX4, kanMX4@chr3 position 214500 bp, ade6Δ::hphMX4, rec12Δ::ura4+ |
| SZY685 | hybrid with Sk karyotype | ura4Δ::natMX4, kanMX4@chr3 position 214500 bp, ade6Δ::hphMX4, rec12Δ::ura4+ |
| SZY686 | hybrid with Sk karyotype | ura4Δ::natMX4, kanMX4@chr3 position 214500 bp, ade6Δ::hphMX4, rec12Δ::ura4+ |
| SZY702 | hybrid with Sk karyotype | h90, ura4-x, ade6Δ::hphMX4 |
| SZY862 | Sk | h90, wtf4Δ :kanMX4truncation(drugS), ura4Δ::natMX4, leu1Δ::hphMX4 |
| SZY863 | Sk | h90, wtf4Δ::kanMX4truncation(drugS), ura4Δ::natMX4, leu1Δ::hphMX4, ura4+ |
| SZY871 | Sk | h90, leu1Δ::hphMX4 |
| SZY873 | Sk | h90, ura4Δ::natMX4 |
| SZY876 | Sk | h90, ura4Δ::natMX4, lys1Δ::kanMX4, wtf4Δ::kanMX4(truncated drug S) |
| SZY887 | Sp | h90, leu1-32, ura4-D18, ade6-::Skwtf4::kanMX4::ade6- |
| SZY925 | Sp | h90, leu1-32, ura4-D18, ade6-::kanMX4::ade6- |
| SZY960 | Sp | h90, leu1-32, ura4-D18, ade6-::Skwtf4-GFP::kanMX4::ade6- |
| SZY958 | Sp | h-, lys4-95, ade6-::Skwtf4-GFP::kanMX4::ade6- |
| SZY1030 | Sp | h?, hht1-RFP::kanMX6, lys1-37 |
| SZY1033 | Sp | h90, leu1-32, ura4-D18, ade6-::Skwtf4(357A > T, 358T > A, 359G > C)::kanMX4::ade6- |
| SZY1035 | Sp | h90, leu1-32, ura4-D18, ade6-::mCherry5Xglycine-Skwtf4::kanMX4::ade6- |
| SZY1044 | Sp | h90, leu1-32, ura4-D18, ade6-::Skwtf28::kanMX4::ade6- |
| SZY1049 | Sp | h90, leu1-32, ura4-D18, ade6-::Skwtf4(M1X, M12X)-GFP::kanMX4::ade6- |
| SZY1051 | Sp | h90, leu1-32, ura4-D18, ade6-::Skwtf4(M1X, M12X)::kanMX4::ade6- |
| SZY1064 | Sp | h-, lys4-95, ade6-::Skwtf4::hphMX4::ade6- |
| SZY1072 | Sp | h90, ura4-D18, leu1-32, hht1-RFP::kanMX4, ade6-::Skw tf4::hphMX4::ade6- |
| SZY1095 | Sp | h-, lys4-95, ade6-::Skwtf4-GFP::kanMX4::ade6-, his5Δ::ade6+ |
| SZY1110 | Sp | h-, ade6-::Skwtf4(357A > T, 358T > A, 359G > C)::kanMX4::ade6-, lys4-95 |
| SZY1140 | Sp | h90, hht1-CFP::hphMX4, his3-D1 |
| SZY1142 | Sp | h90, ura4-D18, his5Δ::ade6+, lys1-37, ade6-::mCherry5Xglycine-Skwtf4::kanMX4::ade6- |

Figure 1B:
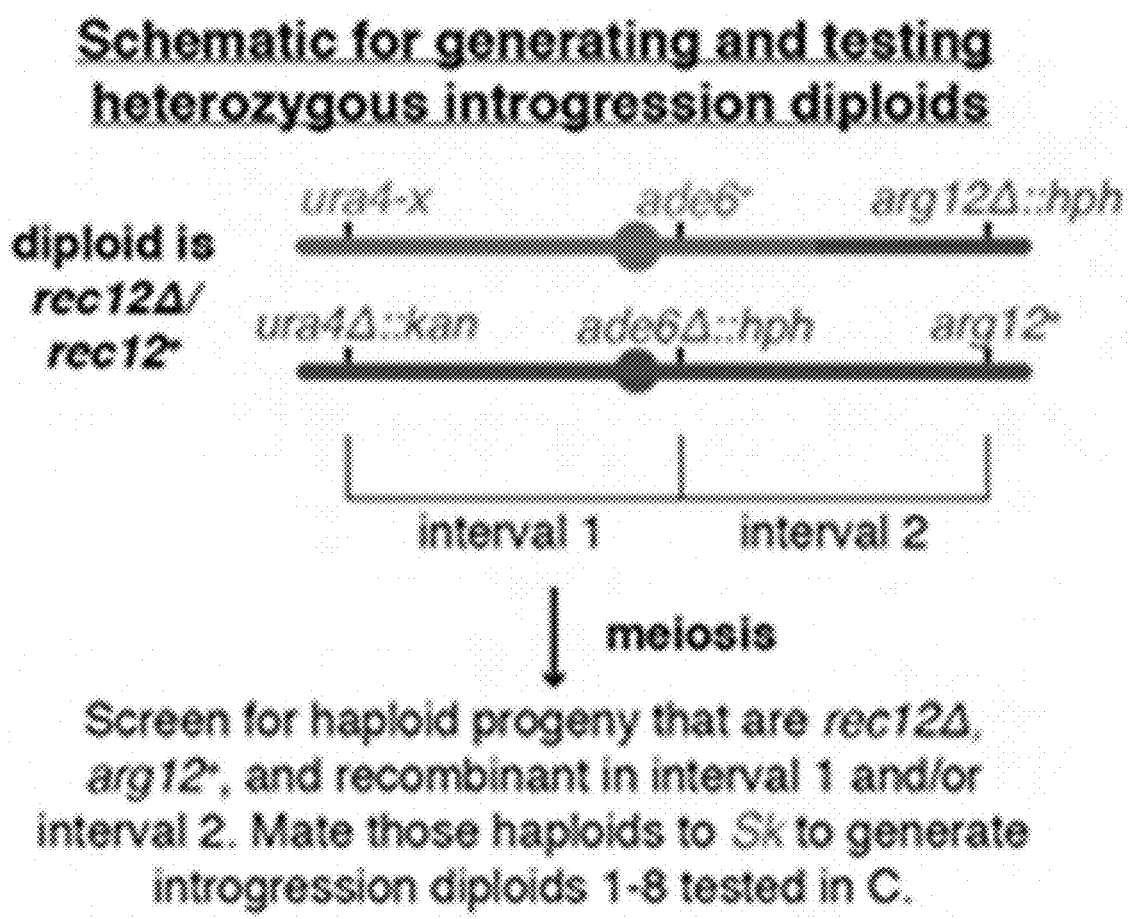

Sequencing data from all high-throughput sequencing was deposited to GenBank accession number PRJNA376152. A drive allele present on Sk chromosome 3 was first chosen to map via recombination mapping. To eliminate the effects of drivers and gross chromosome rearrangements from chromosomes 1 and 2, the mapping effort was begun using a strain (SZY558) that contains chromosomes 1 and 2 from Sk, but in which most of chromosome 3 was derived from Sp (the mosaic chromosome illustrated in FIG. 1B is from SZY558). A complete Sp chromosome 3 was not used because such a strain lacks essential genes due to a translocation between chromosomes 2 and 3 that occurred in the Sk lineage (18). Sequencing revealed that chromosome 3 in SZY558 was generated by a crossover event between Sp and Sk chromosomes somewhere between positions 1,804,477 and 1,810,659 on the Sp chromosome. The region to the right of this point contains Sk alleles and the strain has the Sk karyotype (FIG. 1B).

Figure 1D:
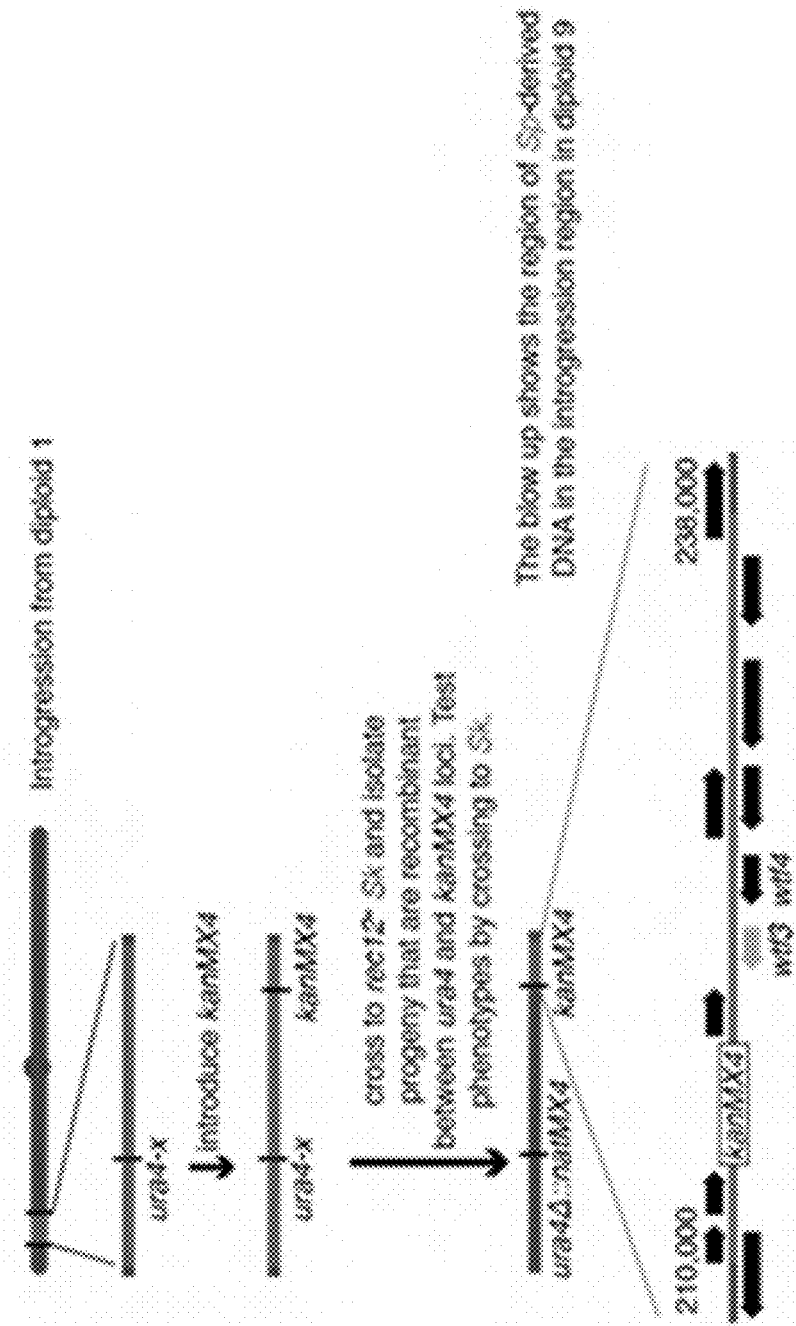
Figure 1E:
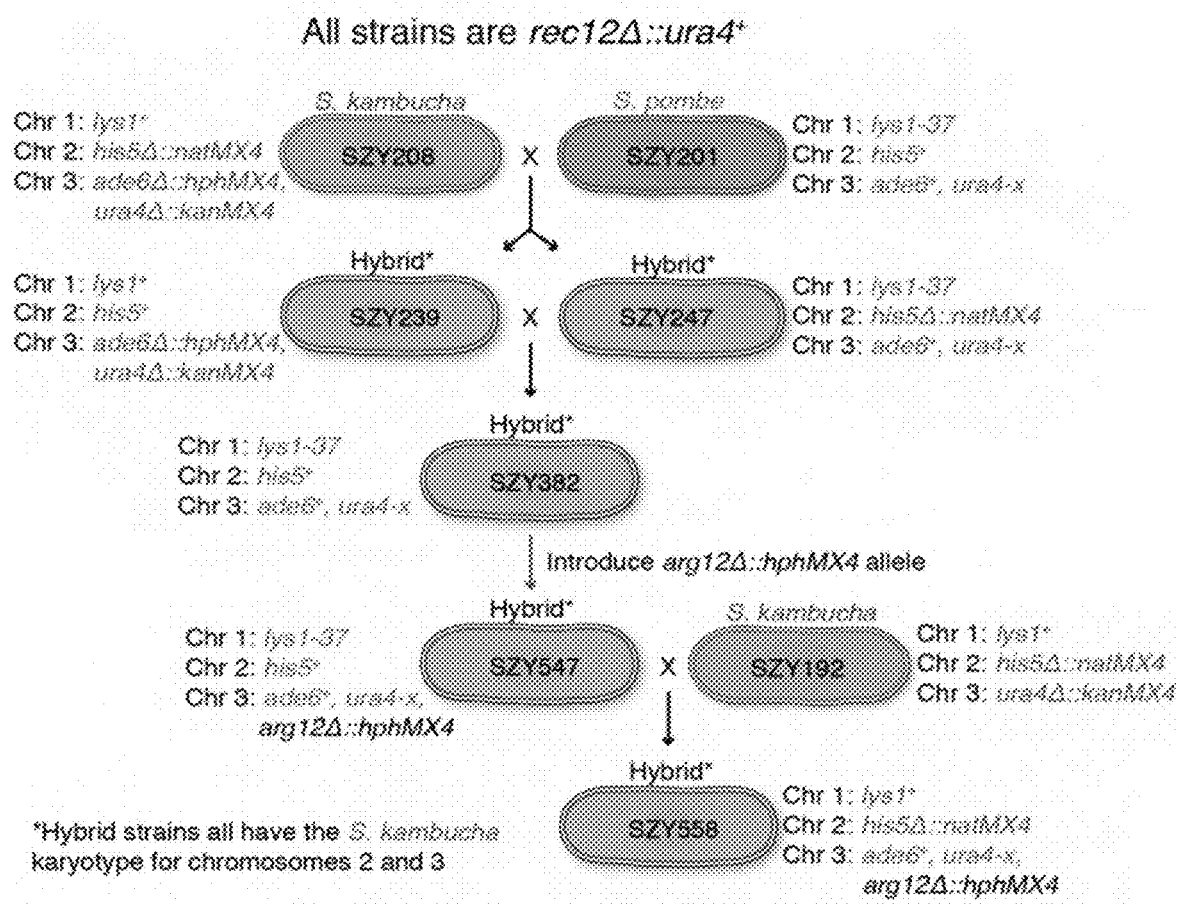

The generation of SZY558 is described in FIG. 1E. SZY558 was generated by first crossing SZY201 (Sp) to SZY208 (Sk) to generate SZY239 and SZY247. Although no recombination was expected in this cross because the two parental strains are rec12Δ, both SZY239 and SZY247 must contain a recombinant chromosome 2 and/or a recombinant 3 because they inherited non-parental combinations of markers on chromosomes 2 and 3, and the two species karyotypes are incompatible (18, 38). Such recombinant spores are quite rare (18), but were obtained via selection for nonparental combination of markers on chromosome 2 and 3 (e.g., His$^+$ hygromycin resistant). Most such selected progeny are chromosome 3 aneuploids, so the strains were then streaked to single colonies to allow them to lose the additional copy of chromosome 3. SZY239 to SZY247 were crossed to generate a strain (SZY382) that contained the recombinant chromosome 3, but also had the lys1-37 and his5$^+$ markers on chromosomes 1 and 2 respectively. The lys1-37 and $^{his5+}$ markers in this strain were useful for following chromosomes 1 and 2 in a subsequent cross. SZY382 was transformed with a PCR fragment generated with oligos 255 and 256 using plasmid pAG32 as a template to generate a strain (SZY547) with arg12Δ::hphMX4 (39). The arg12 locus is on chromosome 3 in Sk and in strain SZY547, which has the Sk karyotype. SZY547 to SZY192 (Sk) was then crossed to generate strain SZY558. The purpose of this cross was to move the recombinant chromosome 3 into a strain background with pure Sk chromosomes 1 and 2 (marked with lys1$^+$ and his5Δ::natMX4).

For mapping Sk wtf4, SZY558 was crossed to a differentially marked Sk strain (SZY210) to generate recombinant haploid progeny (introgression stains) that contained a smaller fraction of chromosome 3 from Sp (FIG. 1B). Genetic markers (ura4, ade6 and arg12) were used to select only true haploid recombinants for our introgression strains. Matings were performed between the introgression strains and Sk (SZY196) to generate diploids 1-8 (FIG. 1C). The mapping scheme was designed such that diploids generated by the matings were homozygous rec12Δ, so recombination would infrequently separate the drive allele from the genetic markers used to distinguish the introgression and Sk chromosomes (38). At least one introgression was sequenced representing each phenotype observed amongst these strains and distinguished Sp and Sk SNPs as in (FIG. 1F) (18).

SZY565 (the haploid parent that contributed the mosaic chromosome 3 to diploid 1 in FIG. 1C) is the introgression strain that contains the smallest region of Sp-derived DNA, from position 55,555 to 237,572 (FIG. 1F). The Sk chromosome drove against this introgression in test crosses. It was assumed that whatever feature of the Sp genome (either the presence of a target of killing or the absence of an antidote to killing) that conferred the sensitive phenotype (i.e. susceptibility to being destroyed by the Sk driver) must be within that region and, correspondingly, that the Sk drive allele must also be within or very near that region. This is because a drive allele that acts to kill gametes that do not inherit it should target the homologous locus or a closely linked site to prevent self-killing. A drive allele that killed gametes that inherit a locus not linked to the drive allele would be an evolutionary dead-end because it would kill gametes bearing the drive allele as often as it would kill gametes bearing the competing allele.

To narrow in on the key drive locus, SZY565 to SZY196 (Sk) were crossed to get a strain (SZY649) with the same chromosome 3 as SZY565, but with his5$^+$ rather than his5Δ::natMX4 on chromosome 2. The ura4 locus, at position 116,726-115,589 on chromosome 3, is within the Sp-derived region. An additional marker (kanMX4) was added within the Sp-derived region at position 214,491 to generate strain SZY659. To do this, plasmid pSZB134 was first generated which contains ~1 kb of DNA (amplified from Sp genomic DNA with oligos 380 and 381) upstream of the target site (214,491) cloned into the BamHI and BglII sites of pFA6a, and ~1 kb of DNA (amplified with oligos 382+383) downstream of the target site cloned into the Sac and SpeI sites of the pFA6a (40). The transformation cassette was released from pSZB134 via NotI digest and used to make SZY659.

SZY659 was then crossed to a differentially marked Sk strain (SZY320; rec12$^+$) and screened for haploid progeny that had experienced a crossover within the Sp-derived region between the ura4Δ::natMX4 allele from SZY320 and the kanMX4 allele in SZY659 (FIG. 1D). Nine such haploids were tested by test crossing them to Sk (SZY196). Two haploids had an Sk-like phenotype in that they showed Mendelian transmission of the ura4 locus; the other six showed the sensitive phenotype. SNPs of the haploids were genotyped at a few sites within the region to roughly estimate where the recombination event(s) occurred (18). Amongst the haploids with the sensitive phenotype, SZY679 and SZY685 have the most Sk-derived DNA; they contain Sp DNA only between position 210,000 (between 207,954 and 210,312) to 237,572 (FIG. 1C, diploid 9; FIG. 1F). The two strains with the Mendelian phenotype (SZY684 and SZY686) contain very little Sp-derived DNA. The Sp DNA begins between positions 210,312 and 214,500 and ends before 215,926. Comparing these two classes suggested that the key drive locus is located between positions 210,000 and 237,572 (but not within the small region surrounding 214,000). The annotated features of this region include all or part of ten genes plus one pseudogene in Sp (FIG. 1D).

Table IV shows the various plasmid constructs.

TABLE IV

| plasmids | short description | reference |
|---|---|---|
| pFA6 | contains kanMX4 | 40 |
| pAG32 | contains hphMX4 | 39 |
| pSZB134 | contains cassette to target kanMX to position 214,491 in Sp chr 3 | this work |
| pSZB184 | pMZ283 expressing guide RNA to target wtf4 | this work |
| pMZ222 | contains Cas9 | 44 |

TABLE IV-continued

| plasmids | short description | reference |
|---|---|---|
| pMZ283 | empty vector for expressing Cas9 guide RNA | 44 |
| pSZB136 | contains cassette to generate leu1Δ::hphMX4 | this work |
| pKT127 | contains yEGFP | 30 |
| pSZB188 | derivative of pFA6a that integrates at ade6, yielding ade6- | this work |
| pSZB189 | pSZB188 with Sk wtf4 cloned into SacI site | this work |
| pSZB209 | pSZB188 with Sk wtf21 and wtf26 cloned into SacI site | this work |
| pSZB212 | pSZB188 with Sk wtf2 cloned into SacI site | this work |
| pSZB217 | pSZB188 with Sk wtf5 cloned into SacI site | this work |
| pSZB215 | pSZB188 with Sk wtf6 and wtf28 cloned into SacI site | this work |
| pSZB252 | pSZB188 with Sk wtf6 cloned into SacI site | this work |
| pSZB254 | pSZB188 with Sk wtf28 cloned into SacI site | this work |
| pSZB203 | pSZB188 with Sk wtf4-GFP cloned into SacI site | this work |
| pSZB204 | pSZB188 with Sk wtf4-GFP cloned into SacI site | this work |
| pSZB215 | pSZB188 with Sk wtf6 and wtf28 cloned into SacI site | this work |
| pSZB246 | pSZB188 with Sk wtf4antidote (ATG to TAC at nucleotide position 356) cloned into SacI site | this work |
| pSZB244 | pSZB188 with Sk wtf4 (ATG to TAG at nucleotide position 1) cloned into SacI site | this work |
| pSZB248 | pSZB188 with Sk mCherry-wtf4 cloned into SacI site | this work |
| pSZB252 | pSZB188 with Sk wtf6 cloned into SacI site | this work |
| pSZB254 | pSZB188 with Sk wtf28 cloned into SacI site | this work |
| pSZB257 | pSZB188 with Sk wtf4poison (ATG to TAG at nucleotide position 1 and ATG to TAG at position 34)-GFP cloned into SacI site | this work |
| pSZB258 | pSZB188 with Sk wtf4poison (ATG to TAG at nucleotide position 1 and ATG to TAG at position 34) cloned into SacI site | this work |
| pAG25 | contains natMX4 | 39 |

Sequencing of the Sk wtO4 Locus

Using oligos MESZ176 and MESZ177, the region corresponding to the wtf3+wtf4 locus in Sp was amplified from Sk genomic DNA. The product amplified is at least 1.5 kb smaller than the corresponding product from Sp. The PCR product was then sequenced using oligos 557, 560, 565, 566, 567, 568, 569, 570, 595, 597, 598, 599, 601, 602, and 603, and assembled a 2,943 bp contig. This sequence has been deposited to GenBank, accession number KY652738. A BLAST search was performed comparing the Sk sequence contig to all Sp protein sequences and got Sp wtf13 and wtf4 as top hits. The Sk region contains only one wtf-like gene, whereas the Sp region has the complete wtf4 gene and the wtf3 pseudogene. As the Sk gene appears to be orthologous to Sp wtf4 based on synteny and sequence similarity, the gene was named Sk wtf4.

The Sp PacBio meiotic transcriptome sequences were used to predict intron/exon boundaries in Sk wtf4 (29). wtf genes are not well-represented in the splice isoform summary tables generated for the Kuang et al. study due to the very high nucleotide identity between wtf paralogs and stringent filtering of multiply-mapping reads. Therefore the Iso-Seq data was re-mapped to the Sp reference genome assembly using GMAP (41), reporting only alignments with ≥99% identity and covering ≥99% of the length of the isoform sequence, and using the parameter "-suboptimal-score 20" to reduce secondary matches (this parameter choice successfully eliminates cross-mapping between wtf4 and wtf13). IGV (42) was used to visualize splice isoforms for each gene. These data reveal a coding sequence that is slightly different from that of the currently annotated Sp wtf4 gene (www.pombase.org/spombe/result/SPCC548.03c). The long form of Sk wtf4 has six predicted exons and encodes a 337 amino acid protein with 82% amino acid identity to the 366 amino acid protein encoded by Sp wtf4. The TMHMM model predicts six transmembrane helices with high probability (>80%) and one with lower probability (<50%) (43).

Table V shows the various sequencing oligonucleotides.

TABLE V

| Oligo | Sequence (5'→3') | SEQ ID NO: |
|---|---|---|
| 255 | TATTACATCAGTGCGCTATCAGTTTAAAAGGTTGGGCCTACTAACTTAACATATACTACACCTCAAGAAAAAGAAAGAACACATACGATTTAGGTGACAC | SEQ ID NO: 5 |
| 256 | TTTGCACAGCAGAAATTTGATTATTGCTTGGCTCAAGTACATGGTGAGTATGACATTATTATTGAGAACGACCTGGCATAATACGACTCACTATAGGGAG | SEQ ID NO: 6 |
| 380 | GTCGGATCCCATTCGTTATCGTTCCAAGTGTGCTGCCGTCG | SEQ ID NO: 7 |
| 381 | GTCAGATCTCTGTTTTGGAAACTTTTTTATCCTCTAACGATGACGATAAASTTTAC | SEQ ID NO: 8 |
| 382 | GTCGAGCTCAATACAGGTAAATGGTCTAAATCAGTATGTAAGCC | SEQ ID NO: 9 |

TABLE V-continued

| Oligo | Sequence (5'→3') | SEQ ID NO: |
|---|---|---|
| 383 | GTCACTAGTGCTATGATTCCGGGAATTGATGTTTCTTCTGAC | SEQ ID NO: 10 |
| 413 | CTCTGAAGACGCAGGTAGTAAAAAACCCG | SEQ ID NO: 11 |
| 414 | GTGAGTATGTACCTTCAATACACCCTTGATG | SEQ ID NO: 12 |
| 557 | CTGCGTAGCTGACATGTTATTGCGATAAC | SEQ ID NO: 13 |
| 560 | GCATTGCTTGAAAGATTCTGCGATGTTGG | SEQ ID NO: 14 |
| 565 | GGTTAGAGTAAATTACAGGAATATATAACGAACCC | SEQ ID NO: 15 |
| 566 | GGGTTCGTTATATATTCCTGTAATTTACTCTAACC | SEQ ID NO: 16 |
| 567 | CTACCTTGCCGAATATCGACTTCTCCAAC | SEQ ID NO: 17 |
| 568 | GTTGGAGAAGTCGATATTCGGCAAGGTAG | SEQ ID NO: 18 |
| 569 | CTGAACGAGGCAGTGGATTGCTTCTG | SEQ ID NO: 19 |
| 570 | CAGAAGCAATCCACTGCCTCGTTCAG | SEQ ID NO: 20 |
| 571 | GTTATGATGGAGAACCCGGAAATTAGAGGC | SEQ ID NO: 21 |
| 572 | GTGTCACCTAAATCGTATGTGGGGAACAGAAATAAACAAGTCTAAAGTGCC | SEQ ID NO: 22 |
| 573 | CTCCCTATAGTGAGTCGTATTAAACTGCGTAGCTGACATGACACTGAATTTC | SEQ ID NO: 23 |
| 574 | CCAGGCAACATCCATTCTCATCAGATGAGG | SEQ ID NO: 24 |
| 575 | ATTTCTGTTCCCCACATACGATTTAGGTGACAC | SEQ ID NO: 25 |
| 576 | CAGCTACGCAGTTTAATACGACTCACTATAGGGAG | SEQ ID NO: 26 |
| 577 | CATTTTCACAAATGGTTCGAGT | SEQ ID NO: 27 |
| 578 | TCGAACCATTTGTGAAAATGTT | SEQ ID NO: 28 |
| MESZ176 | TGGTTAAGCATGTGATCTTCATACGACGC | SEQ ID NO: 29 |
| MESZ177 | AGAAATTCAGTGTCATGTCAGCTACGCAG | SEQ ID NO: 30 |
| 588 | ATGAGCGAAAAACAGGTTGTAGGGATC | SEQ ID NO: 31 |
| 589 | GGTACCTGACCTGAATTGTGAGGCCGAGG | SEQ ID NO: 32 |
| 590 | CCATAGCAGCCAAAAGGGAGGGTTG | SEQ ID NO: 33 |
| 591 | CACAATTCAGGTCAGGTACCCAACACCCAACTCTCGACTTCCAC | SEQ ID NO: 34 |
| 595 | GGGTTGTAATGTTACCTATCACTAATATAGCTC | SEQ ID NO: 35 |

TABLE V-continued

| Oligo | Sequence (5'→3') | SEQ ID NO: |
|---|---|---|
| 597 | GCTTAATTATCATTTTTTCCATTTGTTTAATGGTTTAC | SEQ ID NO: 36 |
| 598 | CGGGTAAGTAAAGAATCATTCATACAGTTGG | SEQ ID NO: 37 |
| 599 | CCGCTAACACGCAGTTCGTCTTCC | SEQ ID NO: 38 |
| 601 | CCCTTCTGAGACTACTAATATCAGTTCTTG | SEQ ID NO: 39 |
| 602 | GGAATCGAGTCAGCAGTTGTTATCAACGGG | SEQ ID NO: 40 |
| 603 | CCCGTTGATAACAACTGCTGACTCGATTCC | SEQ ID NO: 41 |
| 604 | CTGAATATGGAGGCAATGTGCTCTCATC | SEQ ID NO: 42 |
| 605 | ATGAAGAATAAAGATTATCCCTTGAGGTCGTCTATGG | SEQ ID NO: 43 |
| 606 | TAAACCAGCACCGTCACCGACTTCGCTTTCAACTTCCATTTCCCCC | SEQ ID NO: 44 |
| 607 | GGGGGAAATGGAAGTTGAAAGCGAAGTCGGTGACGGTGCTGGTTTA | SEQ ID NO: 45 |
| 619 | AATATAGGAGCTCTGGTTAAGCATGTGATCTTCATACGACGC | SEQ ID NO: 46 |
| 620 | AATATAGGAGCTCAGAAATTCAGTGTCATGTCAGCTACGCAG | SEQ ID NO: 47 |
| 633 | AATATAGAGCTCAGAAATTCAGTGTCATGTCAGCTACGCAG | SEQ ID NO: 48 |
| 634 | AATATAGAGCTCCGGGGACGAGGCAAGCTAAAC | SEQ ID NO: 49 |
| 643 | AATATAGAGCTCAATGCTTCAAAATAATTTTGTAAATCATGTTATGCCG | SEQ ID NO: 50 |
| 644 | AATATAGAGCTCTCTATCACAAAAAAGGTTGCAGCGGAGC | SEQ ID NO: 51 |
| 647 | AATATAGAGCTCCGGCTACTGATAATTGCCTTGCACTCTTC | SEQ ID NO: 52 |
| 648 | AATATAGAGCTCCGAATTGAGTTTGTAGGAAGAAACAAAGTTCC | SEQ ID NO: 53 |
| 649 | AATATAGAGCTCGGCTCTTCGATGCAAAGTAAGGTAAGTAGTTG | SEQ ID NO: 54 |
| 650 | AATATAGAGCTCCATCTCTAAACCCGTATTTGGTAGAAACGGC | SEQ ID NO: 55 |
| 651 | AATATAGAGCTCCCGAAGTATCATATCAACGTAGTACACCATG | SEQ ID NO: 56 |
| 652 | AATATAGAGCTCGGAGGCAAAGCCAAACGTTCTAGC | SEQ ID NO: 57 |
| 686 | AATATAGGAGCTCTATAATAGATCACAAAGGAAAACTCGCCGCAG | SEQ ID NO: 58 |
| 687 | AATATAGGAGCTCCTGCGTAGCTTACATGTTATTGCGATAACATTTCG | SEQ ID NO: 59 |
| 701 | GTGTATATCATTCAATAATAGATTGTTTTTAAGAATAGAAGAATAAAGATTATCCC | SEQ ID NO: 60 |
| 702 | GGGATAATCTTTATTCTTCTATTCTTAAAAACAATCTATTATTGAATGATSATACAC | SEQ ID NO: 61 |

TABLE V-continued

| Oligo | Sequence (5'→3') | SEQ ID NO: |
|---|---|---|
| 732 | AATATAGAGCTCGCGTTATTAATGTAGTTGTCGCTACAGTTGG | SEQ ID NO: 62 |
| 733 | AATATAGAGCTCCTTCTTATTCACCCCAACTTAGATTTCCTTATGCATC | SEQ ID NO: 63 |
| 735 | CCAAATTTCAAAAGTTATTTATTTTATTATACCTTTCAGAAATTTGGAAAATATATTAAAACTGTATCTGAAG | SEQ ID NO: 64 |
| 736 | CTTCAGATACAGTTTTAATATATTTCCAAATTTCTGAAAGGTATAATAAAAATAAATAACTTTTGAAATTTGG | SEQ ID NO: 65 |
| 739 | GTACTCAATTCATCCtTAAGACGACCTCAAGGG | SEQ ID NO: 66 |
| 740 | CCCTTGAGGTCGTCTTAGGATGAATTGAGTAC | SEQ ID NO: 67 |
| 795 | AAATGGAATGCCCATCCTGATCTTAACTTG | SEQ ID NO: 68 |
| 796 | TCCCTACAACCTGTTTTTCGCTCATCGTGATGCAAAACTACTCTTTTCAATTAGA | SEQ ID NO: 69 |
| 797 | AAAGTTGGTTGGAAAAATTATTCTGCATAGAGATGAATTGGATTATGTCAGGAAAAGAAC | SEQ ID NO: 70 |
| 798 | GTGAACGATTAGGGACGAATTATCAACTGT | SEQ ID NO: 71 |
| 799 | TCTAATTGAAAAGAGTAGTTTTGCATCACGATGAGCGAAAAACAGGTTGTAGGGA | SEQ ID NO: 72 |
| 800 | GTTCTTTTCCTGACATAATCCAATTCATCTCTATGCAGAATAATTTTTCCAACCAACTTT | SEQ ID NO: 73 |
| A01112 | TAACGCCGCCATCCAGTGTCG | SEQ ID NO: 74 |
| 678 | GCCGAATATCGACTTCTCCAACGGG | SEQ ID NO: 75 |
| 861 | GCCCTGTTAGACGAATTTATGCTCGTAATATGTC | SEQ ID NO: 76 |

Generation of Sk wtf4Δ Mutants

To generate the Sk wtf4Δ mutant, the CRISPR-Cas9 system was used after first failing to generate the mutant via the standard homologous recombination approach (36). This system requires the starting strain to be ura4⁻ and leu1⁻. A Sk mutant (SZY661) was generated in which leu1 was replaced with hphMX4 in strain SZY320 by first cloning a leu1Δ::hphMX4 cassette (pSZB 136). This plasmid was made by first cloning leu1⁺ (amplified from Sk genomic DNA with oligos 413 and 414) into pFA6a cut with NdeI and ClaI and blunted with Klenow fragment of DNA polymerase 1. This new vector was then cut with ClaI and NdeI (within leu1) and blunted with Klenow: the hphMX4 cassette liberated from pAG32 with PvuII and ClaI was ligated into the gap (39). Oligos 413 and 414 were used again to amplify the leu1Δ::hphMX4 cassette for transformation.

To generate plasmid pSZB184, which encodes a guide RNA targeting the Sk wtf4 region, oligos 577 and 578 were annealed and cloned into the CspCI site of pMZ283 (44). Overlap-PCR was used to generate a repair cassette containing ~1 kb of homology upstream and downstream of the Sk wtf4 region flanking the kanMX4 cassette from pFA6a (40). The products of PCRs generated with oligos 571 and 572, 575 and 576, and 573 and 574 were stitched together to make the repair cassette. Strain SZY661 was then transformed with pMZ222, pSZB184, and the repair cassette. Ura⁺Leu⁺ transformants were screened containing both plasmids for wtf4 deletions via PCR and sequencing. It was found that strain SZY862 contained a deletion of wtf4, but unexpectedly was not resistant to G418. Sequencing of the region revealed a truncation of the kanMX4 gene. SZY863 contains the same deletion as SZY862, but is Ura⁺ due to retention of the ura4⁺ cassette from pSZB184 at an unknown location closely linked to the endogenous ura4 locus, although the strain retains the ura4Δ::natMX4 allele at the endogenous ura4 locus.

Generation of the Ade6-Targeted Constructs

First generated was pSZB188, a plasmid containing the kanMX4 selectable marker and a mutant ade6 allele that has 5', central, and 3' deletions. This vector can be cut with KpnI within the mutant ade6 gene and then integrated into ade6⁺ to generate Ade-G418-resistant transformants. Other genes can be added to the vector to introduce them into the genome at the ade6 locus. To construct pSZB188, first a mutant ade6 cassette was made via overlap PCR stitching a PCR product made from oligos 588 and 589 to one made from oligos 591 and 590. This ade6 cassette was then digested with BamHI and XhoI and cloned into the BamHI and SalI sites of pFA6a (40). The Sk wtf4 region was cloned into pSZB188 by first amplifying the region with oligos 619 and 620. The PCR product was digested with SacI and cloned into the SacI site of pSZB188 to generate pSZB189. KpnI-digested pSZB189 was introduced into yeast and transformants were selected on YEA with G418 plates. Red colonies were picked, as proper integrants should harbor a mutant ade6 allele flanking the sides of the plasmid sequence. The duplicated ade6 gene makes the locus unstable and Ade+ revertants that have 'popped out' all plasmid-derived sequences are readily obtained.

The Sk wtf4-GFP allele was made using overlap PCR. The promoter region from Sk genomic DNA was amplified using oligos 633 and 604 and the open reading frame sequence using oligos 605 and 606. pKT127 was used as a template to amplify yEGFP using oligos 607 and 634 (30). The three PCR products were then stitched together using overlap PCR. The resulting cassette was cut with SacI and cloned into the SacI site of pSZB188 to generate pSZB204. This construct was integrated at ade6 as described above.

For the Sk wtf4$^{antidote}$ allele, using overlap PCR, the two PCR products generated with oligo pairs 735 and 686, and 620 and 736, both using pSZB189 as a template, were stitched together. The stitched PCR product was cloned into the SacI site of pSZB188 to generate pSZB246. pSZB246 was then cut and introduced into yeast as described above.

The Sk wtf4$^{poison}$ allele was generated using overlap PCR. Sk wtf4 has two in-frame start codons in the annotated exon 1. Mutating the first start codon had no phenotype (data not shown), so both were mutated. To mutate the first start codon, overlap PCR was used to stitch together two PCR products made by oligo pairs 701 and 686, and 620 and 702; both reactions used pSZB189 as a template. The stitched PCR product was cloned into the SacI site of pSZB188 to generate pSZB244. pSZB244 was used as a template to mutate the second start codon via overlap PCR. PCR fragments generated by oligo pairs 620 and 739, and 686 and 740 were stitched together and cloned into the SacI site of pSZB188 to generate pSZB258. pSZB258 was cut and introduced into yeast as described above.

The Sk mCherry$^{antidote}$-wtf4 allele was cloned using overlap PCR. First was purchased, from IDT (Coralville, IA), a synthetic double-stranded DNA gene block including the Sk wtf4 promotor, the mCherry coding sequence (28), five glycine codons, and the first part of Sk wtf4 exon 1. That fragment was amplified with oligos 620 and 604 and then stitched to another that contained the rest of the Sk wtf4 gene amplified with oligos 605 and 687 from plasmid pSZB189. That product was then cloned into the SacI site of pSZB188 to generate pSZB248, which was cut and introduced into yeast as described above.

For the Sk wtf4$^{poison}$-GFP allele, the 5' end of the gene was amplified with oligos 620 and 739 using plasmid pSZB244 as a template. The 3' end of the gene was amplified with oligos 740 and 634 using pSZB203 as a template. Overlap PCR was then used to stitch those PCR fragments together and the product was cloned into the SacI site of pSZB188 to generate pSZB257, which we cut and introduced it into yeast as described above.

The same strategy was used to integrate other Sk wtf genes into Sp. Sk genomic DNA was used as a template to amplify wtf21+wtf26 with oligos 643 and 644, wtf2 with oligos 647 and 648, wtf5 with oligos 649 and 650, and wtf6+wtf28 with oligos 651 and 652. Each cassette was cut with SacI and cloned into the SacI site of pSZB188 to generate: pSZB209 (wtf21+wt26), pSZB212 (wtf2), pSZB217 (wtf5), and pSZB215 (wtf6+wtf28). Sk wtf6 and Sk wtf28 were subcloned from pSZB215 by first amplifying the individual genes using oligo pairs 732+652 and 651+733, respectively. The genes were then cloned into the SacI site of pSZB188 to generate pSZB252 (wtf6) and pSZB254 (wtf28). All sequences of these genes have been deposited in GenBank, accession numbers KY652739-KY652742. These constructs were all integrated at ade6 as described above.

Assaying Allele Transmission in Wtf4$^{poison}$/Wtf$^{antidote}$ Diploid

Because the alleles wtf4$^{poison}$ (SZY1051) and wtf4$^{antidote}$ (SZY1110) are marked with the same drug marker, to score transmission of alleles for this cross, sequencing was used. Diploids and spores were generated as described above. Spores were then plated on YEA, the colonies picked to a YEA master plate and replicated to score control markers. Lysates for PCR from the master plate were also prepared by scraping cells off the master plate into 20 µl of 20 mM NaOH. The cells were boiled for 5 minutes, frozen in liquid nitrogen, boiled again for 10 minutes, and then the debris spun down. Using the supernatant lysate, the wtf4 region was amplified using oligos A01112 and 678. The exon 1 region was then sequenced using oligo 861, and analyzed for the start codon mutations mentioned above (FIG. 4A). If the exon 1 mutations were present, this was quantified as a poison allele; if not present, as an antidote.

Introducing Ade6+ at His5

To avoid ade6− mutant auto-fluorescence in cytology, ade6+ at the his5 locus was introduced. A region upstream of his5 was amplified to generate piece A using oligo pair 795 and 796. A region downstream of his5 was amplified to generate piece C using oligo pair 797 and 798, and to amplify ade6+, piece B was generated using oligo pair 799 and 800. Pieces A, B and C were stitched together using oligo pair 795 and 798 and the product introduced into yeast.

Cytology

For the fertility assay, 5-10 µl of propidium iodide (PI, 1 mg/ml) was added to 50 µl of H$_2$O, and the yeast scraped from the SPA plate into the PI mix. The yeast plus PI mixture was incubated at room temperature for 20 minutes. Images were taken on a Zeiss Observer Z1 wide-field microscope with a 40× (1.2 NA) water-immersion objective and the emission collected onto a Hamamatsu ORCA Flash 4.0 using µManager software. The PI images were acquired with BP 530-585 nm excitation and LP 615 emission, using an FT 600 dichroic filter.

For all other fluorescence microscopy, images were taken on a LSM-700 AxioObserver microscope (Zeiss), with a 40× C-Apochromat water-immersion objective (NA 1.2), with 488 and 555 nm excitation. GFP fluorescence was collected through a 490-55 nm bandpass filter and mCherry fluorescence through a 615 nm longpass filter. The continuously variable secondary dichroic filter was positioned at 578 nm. Images were also taken using a LSM-780 (Zeiss) microscope, with a 40× C-Apochromat water-immersion objective and 100× alpha Plan-Apochromat oil-immersion objective (NA 1.2 and 1.46, respectively), in photon-counting channel mode with 488 and 561 nm excitation. GFP fluorescence was collected through a 481-552 bandpass filter and mCherry through a 572 longpass filter. For all images acquired on the LSM-780 (Zeiss) microscope, using the same objectives as described above, images were also acquired in photon-counting lambda mode, with 488 and 561 nm excitation. Fluorescence emission was collected over the entire visible range. After acquisition, the images were linear unmixed using an in-house custom written plugin for ImageJ (imagej.nih.gov/ij/). Unmixing was achieved using spectra obtained from control cells. Unmixing was performed to verify that there was no auto-fluorescence in the cells (FIG. 5D) scored. Auto-fluorescent cells were not scored. Brightness and contrast is not the same for all images. At least 35 asci (but usually >100) were assayed for each genotype represented in FIGS. 3 and 5.

Example 2

Results

Genetic Mapping Reveals a Complex Landscape of Drive Loci and Modifiers

To study meiotic drive in fission yeast, haploids were mated to generate diploids, the diploids induced to undergo meiosis and allele transmission into the gametes monitored using genetic markers. In Sk Sp hybrid diploids, drive of loci on all three Sk chromosomes is due to the preferential death of gametes inheriting the corresponding Sp alleles (18) (FIG. 1A). In this example, chromosome 3 was focused on because it is the smallest chromosome and the drive phenotype is strong: greater than 80% of viable haploid gametes inherit an Sk marker allele from Sk Sp hybrids (18).

To genetically map a drive locus on chromosome 3, it was beneficial to generate a strain with Sk chromosomes 1 and 2, but Sp chromosome 3. Because Sp and Sk have different karyotypes on chromosomes 1 and 2 due to translocation (18), such a strain could not be generated as it would lack essential genes. Instead, a haploid strain with an Sk karyotype containing Sk chromosomes 1 and 2 and most, but not all, of chromosome 3 derived from Sp was generated (see FIG. 1E and Methods). This haploid strain was backcrossed to Sk to generate a series of haploid strains that have mosaic (Sp and Sk-derived DNA sequences) versions of chromosome 3 generated by recombination. These strains are referred to herein as 'introgressions' (FIG. 1B). Recombinant haploid were then crossed Sk to generate a series of introgression diploids (FIGS. 1B and 1C, diploid 1-8). The introgression diploids were all homozygous null mutants for rec12, the fission yeast ortholog of *S. cerevisiae* SPO11, which is required for inducing DNA breaks to initiate meiotic recombination (20). As meiotic recombination is not induced in the introgression diploids, any genetic marker could be used on chromosome 3 to assay this chromosome for the presence of drive loci. The codominant markers ade6+ and ade6Δ::hphMX4 were used to follow transmission of each chromosome into viable gametes (FIG. 1C).

Three phenotypic classes were observed amongst our introgression diploids (diploids 1-8, FIG. 1C). In the first class (diploids 1-3) the allele from the pure Sk chromosome exhibited drive over the allele from the Sp/Sk mosaic chromosome. In the second class (diploids 4-7), we were surprised to observe the opposite phenotype: the allele from the Sp/Sk mosaic chromosome exhibited drive over that from the pure Sk chromosome. In the third class (diploid 8) we observed unbiased allele transmission.

The finding of three distinct phenotypic classes amongst the introgression diploids (diploids 1-8) is inconsistent with the simple model of a single drive locus on Sk chromosome 3. A single gene model predicts two phenotypic classes: 1) introgression diploids in which the pure Sk chromosome exhibits drive because the Sk Sp mosaic chromosome lacks the Sk drive allele and 2) introgression diploids in which the chromosomes show Mendelian transmission because the Sk Sp mosaic contains the Sk drive allele.

Instead, the data is more consistent with the presence of a meiotic drive allele (or alleles) found on both Sk and Sp chromosome haplotypes and the existence of at least one genetically separable drive suppressor. The drive of the Sk/Sp mosaic chromosome over the pure Sk chromosome in class 2 (diploids 4-7) is consistent with the presence of an Sp drive allele in these strains. The full effects of this Sp drive locus could have been missed previously in Sk/Sp hybrid crosses due to the actions of an Sp drive suppressor not found in the class 2 introgressions (18).

Similar to what we previously observed in crosses between pure Sk/Sp hybrids (both rec12+ and rec12Δ), we found that viable gametes produced by diploids of all three classes frequently inherited both alleles at the ade6 locus (FIG. 1C) (18). This indicates they are not haploid at this locus, as is expected for gametes. These gametes likely represent a mix of heterozygous diploids and heterozygous chromosome 3 aneuploids. In diploid 8, the phenotype was extreme, with almost all the viable gametes inheriting both ade6 alleles (FIG. 1C). Although the frequency of meiotic chromosome missegregation is elevated in rec12Δ mutants (20), we see significantly higher levels of viable gametes that inherit both alleles in diploids 1-8 than we did in a homozygous Sk rec12Δ control (FIG. 1C, diploid 10).

The high level of chromosome 3 aneuploidy and/or diploidy observed in the viable progeny of Sk/Sp hybrid crosses and our introgression diploids (1-8) is also consistent with the existence of both Sk and Sp active meiotic drive loci. It was previously shown in Sk/Sp hybrids that this phenotype was not due to elevated chromosome missegregation in meiosis, but rather preferential death of haploid gametes (18). As was proposed previously, this phenotype could result from distinct competing Sk and Sp driver loci on chromosome 3 (18, 21). In the absence of recombination, a given haploid gamete can inherit only the Sk or Sp drive locus and is thus sensitive to being killed by the one it does not inherit. Heterozygous diploids and heterozygous aneuploids, however, would inherit both loci and be resistant to both killers.

To map driver location(s) from the phenotypic data described above, the haplid strains were sequenced that contributed the Sk/Sp mosaic chromosomes to the introgression diploids (diploids 1-8) and combined genotype information with the phenotypic data described above. It was determined which regions of chromosome 3 were derived from Sk and which were from Sp in each strain (FIGS. 1C and 1F). It was clear from the data that one or two loci were not sufficient to explain the phenotypes of all of these strains. The Sk/Sp mosaic chromosome found in diploid 1 was focused on. This strain has the smallest amount of Sp DNA (−180 kb), and drive of Sk in the introgression/Sk diploid suggested the strain lacks a drive allele found in Sk (FIG. 1C). A haploid isolate containing this chromosome was crossed to a rec12+Sk strain to generate recombinant progeny containing smaller segments of Sp-derived DNA (FIG. 1D and Methods). SNP-genotyping was performed for those recombinants and tested their phenotypes by mating them to Sk to generate additional introgression diploids (See Methods). Diploid 9 was selected for further analysis, as it contains the Sk/Sp mosaic chromosome with the smallest region of Sp-derived DNA (~30 kb) that a pure Sk chromosome can drive against (FIG. 1C and FIG. 1D). After excluding aneuploid/diploid progeny (those that inherit both ade6 markers), the allele from the pure Sk chromosome shows essentially the same transmission bias in diploids 1 and 9. These results suggest the Sk drive allele active in diploid 1 is found in this ~30 kb region. Curiously, this locus is in a region that is transmitted in a Mendelian manner (to ~50% of progeny) in pure Sk/Sp hybrids (18), suggesting that other loci can mask the effects of the driver within this ~30 kb region. In addition, it is unclear why the fraction of viable progeny that inherit both ade6 alleles drops between diploids 1 and 9. These puzzles likely reflect the complexity of the drivers and suppressor loci acting in these yeasts (18).

To verify the candidate drive locus using a recombination-competent (rec12+) diploid, we generated introgression diploid 11 which contains the same Sk/Sp mosaic chromosome as diploid 1, but is rec12+. To follow the transmission of the candidate locus, a closely linked marker gene was needed, so we engineered heterozygous markers at the linked ura4 locus (FIG. 6). It was found that the ura4 allele from the pure Sk chromosome is transmitted to 87% of the viable gametes produced by diploid 11, which is not significantly different from the 88% transmission of the Sk allele in diploid 1 (FIG. 1C and FIG. 2A). This result shows that ura4 is closely linked to an Sk drive locus and is consistent with that locus being within the ~30 kb candidate region.

To test whether the transmission bias observed in diploid 11 might be caused by increased cell death amongst gametes inheriting the Sp locus, propidium iodide (PI) was used to stain the meiotic sacs (asci) that hold the spores. PI efficiently stains dead cells that have lost their membrane integrity but fails to stain viable cells (FIGS. 2B and 2C) (22). We found that only 81% of spores generated by diploid 11 excluded PI, while wild-type strains (e.g. diploid 13) have rates >90% (FIG. 2A). Together, our findings support the hypothesis that the Sk ~30 kb region encodes a gamete-killing meiotic driver.

Example 3

Sk Wtf4 is a Meiotic Drive Locus

Near the center of the Sk 30 kb candidate region is wtf4 (FIG. 1D), a member of the mostly uncharacterized wtf gene family. This family contains 25 members in Sp whose name is derived from the genes' genomic association with Tf transposons (20). wtf genes are not found outside *Schizosaccharomyces* species (23). Sk wtf4 is a 1,427 bp gene (from the start to stop codon, including introns) with six exons and encodes a protein with six predicted transmembrane domains. Sk wtf4 shares only 89% DNA sequence identity (82% amino acid identity) with the gene in the orthologous locus in Sp (Sp wtf4); this divergence is much higher than expected given the 99.5% average DNA sequence identity between the two genomes (17, 18). It was reasoned that wtf genes in general, were good candidates for meiotic drive loci because of their rapid evolution and their transcription during meiosis (23-26).

To test if Sk wtf4 is a meiotic drive gene, Sk wtf4 was deleted (Sk wtf4l) in a pure Sk background and that haploid mated to one containing the same Sk/Sp mosaic found in diploid 11 (FIG. 2A) to produce diploid 12. A significant increase in the number of spores that could exclude PI in diploid 12 (Sk wtf4Δ), compared to diploid 11 (Sk wtf4+) from 81% to 96%, suggesting Sk wtf4+ promotes spore death in progeny of heterozygous diploids. In addition, Sk wtf4Δ showed more equitable allele transmission. While Sk wtf4+ is transmitted to 87% of the viable gametes produced by diploid 11, the transmission rate of Sk wtf4l is reduced to 66% in diploid 12 (FIG. 2). Although some residual transmission bias remains in this background, the results clearly implicate Sk wtf4 as a large contributor to gamete-killing meiotic drive.

Example 4

Sk Wtf4 Drive is Consistent with a Poison/Antidote Mechanism

There are two known means by which gamete-killers act to eliminate competing alleles (5, 26). Under one model, meiotic drivers kill gametes containing a particular target locus (7). For example, the Segregation Distorter (SD) system in *Drosophila melanogaster* kills sperm bearing an expansion of the Responder satellite DNA (12, 27). The second model is a poison/antidote model in which a gamete killing entity (the poison) is encoded at a position that is closely linked to that encoding a second substance (the antidote) which specifically protects gametes that inherit the drive locus. For example, the unidentified rfk gene (required for killing) acts as a poison and the rsk gene (resistance to spore killing) gene acts as an antidote in the Spore killer-2 drive locus from *Neurospora intermedia* (16, 28).

It was first tested if Sk wtf4 acts analogously to SD to kill gametes that inherit a particular Sp chromosomal locus. To test this idea, the effect of deleting Sk wtf4Δ/Sk wtf4+ heterozygosity in a pure Sk strain background was analyzed (diploid 14, FIG. 2A). As this Sk wtf4Δ/Sk wtf4+ heterozygote contains no Sp DNA, there should be no drive if wtf4 can only target and drive against Sp sequence. However, strong drive (93% transmission) was observed of Sk wtf4 relative to Sk wtf4Δ in diploid 14 and a concomitant decrease in the percent of spores that could exclude PI (59% versus 92% fertility in wild-type; FIG. 2A, Diploids 14 and 13). These results demonstrate that the drive of Sk wtf4 does not require an Sp target sequence.

The results are, however, consistent with a poison/antidote model of meiotic drive. The phenotype of the Sk wtfΔ/Sk wtf4 heterozygote (FIG. 2A, diploid 14) suggests that Sk wtf4 acts as the antidote because gametes lacking the gene die. If this was true and a separate gene acted as the poison, it was predicted that Sk wtf4Δ homozygotes (diploid 15) should have very low fertility because they would generate a poison, but no antidote. Contrary to this expectation, it was found that an Sk wtf4Δ homozygote is healthy, with the same ability to exclude PI from the spores as wild-type Sk (92% of spores; FIG. 2A, diploid 13 and 15). This finding rules out the possibility that Sk wtf4 encodes a gene important for meiosis or spore development. Instead, the results suggest that Sk wtf4 acts as both poison and antidote, similar to the Spok genes of *Podospora anserina* (10). It remains unclear, however, why the phenotype of Sk wtf4 is slightly weaker in the hybrid background (assayed in diploids 11 and 12) compared to the phenotypes in pure Sk (diploids 13-15) or pure Sp (diploids 16-18). It is speculated that it could be due to the composition (chromatin state or a sequence variant) of the mosaic chromosome (allele 2 in diploids 11 and 12).

To further test the idea that Sk wtf4 encodes an autonomous poison/antidote drive locus, the gene was moved to a naïve genome and tested to determine if it could induce drive. Sk wtf4 was integrated into the Sp genome at the ade6 locus, which is unlinked to the endogenous wtf4 locus. An Sp diploid that is hemizygous for Sk wtf4 (Sk wtf4/ade6) produces fewer viable spores (54% PI-excluding spores, versus 96% in the vector-only control) and showed a marked transmission bias (96%) favoring Sk wtf4+ (FIG. 2A, diploids 16 and 17). In contrast, Sp diploids homozygous for Sk wtf4+ produced viable spores that excluded PI at the same frequency as spores from wild-type diploids and showed unbiased allele transmission (FIG. 2A, diploids 18 and 16). These results are consistent with Sk wtf4 acting as a complete one-gene poison-antidote drive system that causes the death of gametes that fail to inherit the locus from heterozygote.

Example 5

Sk Wtf4 Generates a Poison and an Antidote from Alternate Transcripts

Figure 3A:
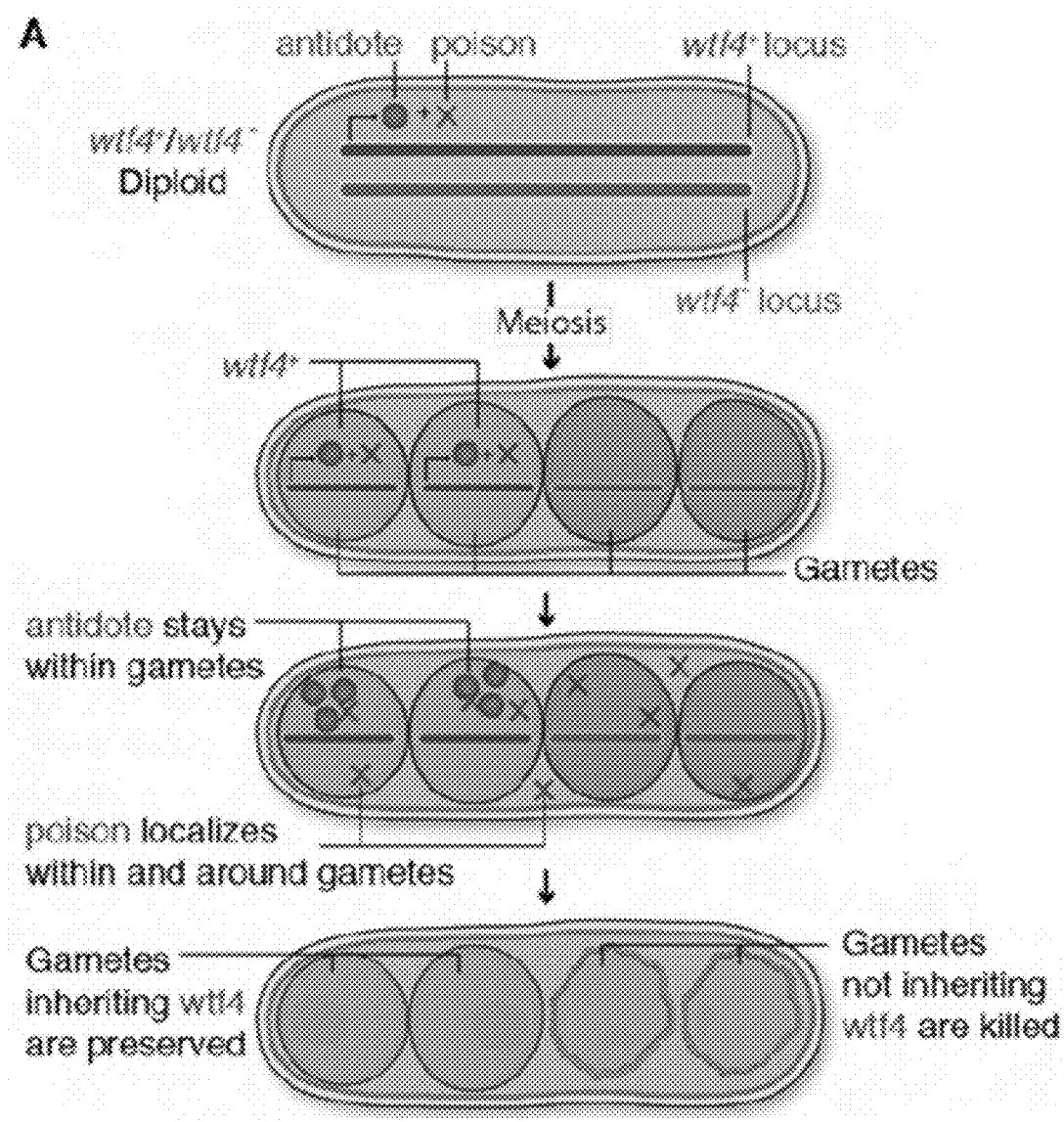
FIG. 3A to FIG. 3D shows that Sk wtf4 has the capacity to make two proteins and Wtf-GFP shows a dual localization pattern.
Figure 3B:
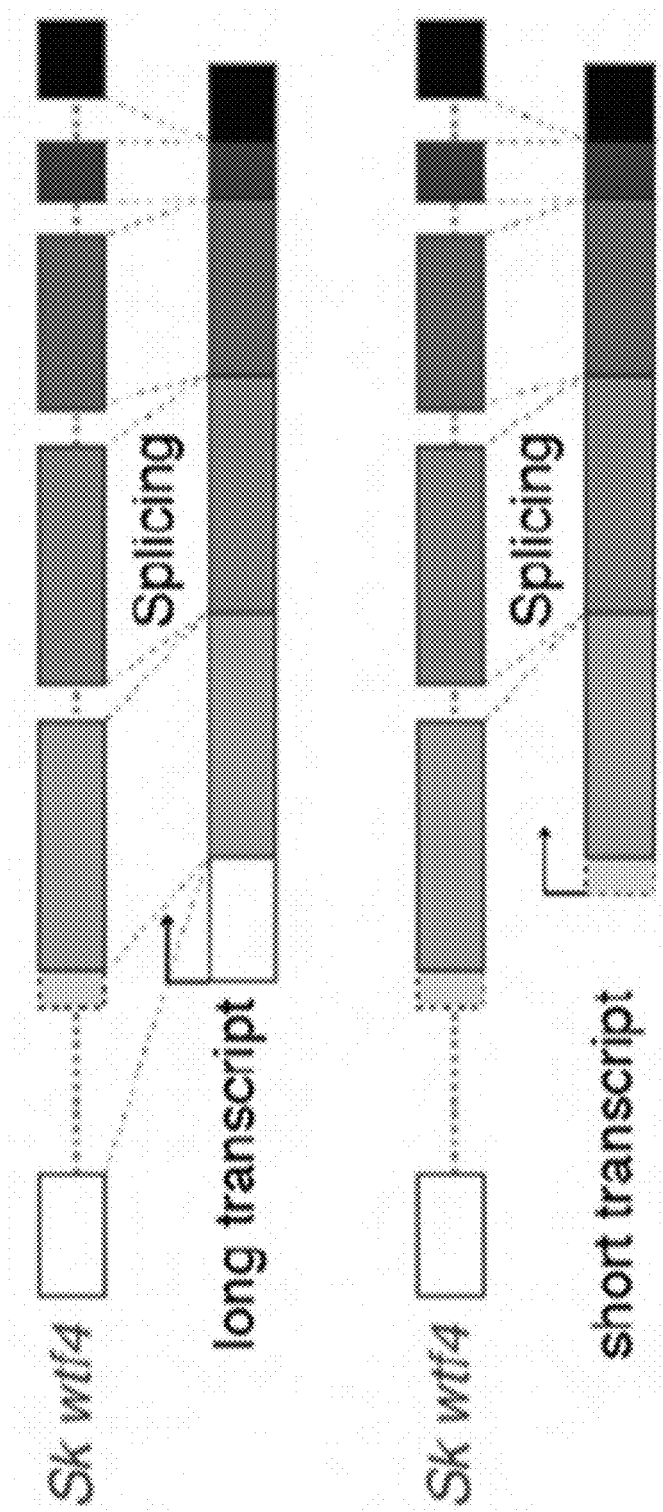
Figure 3C:
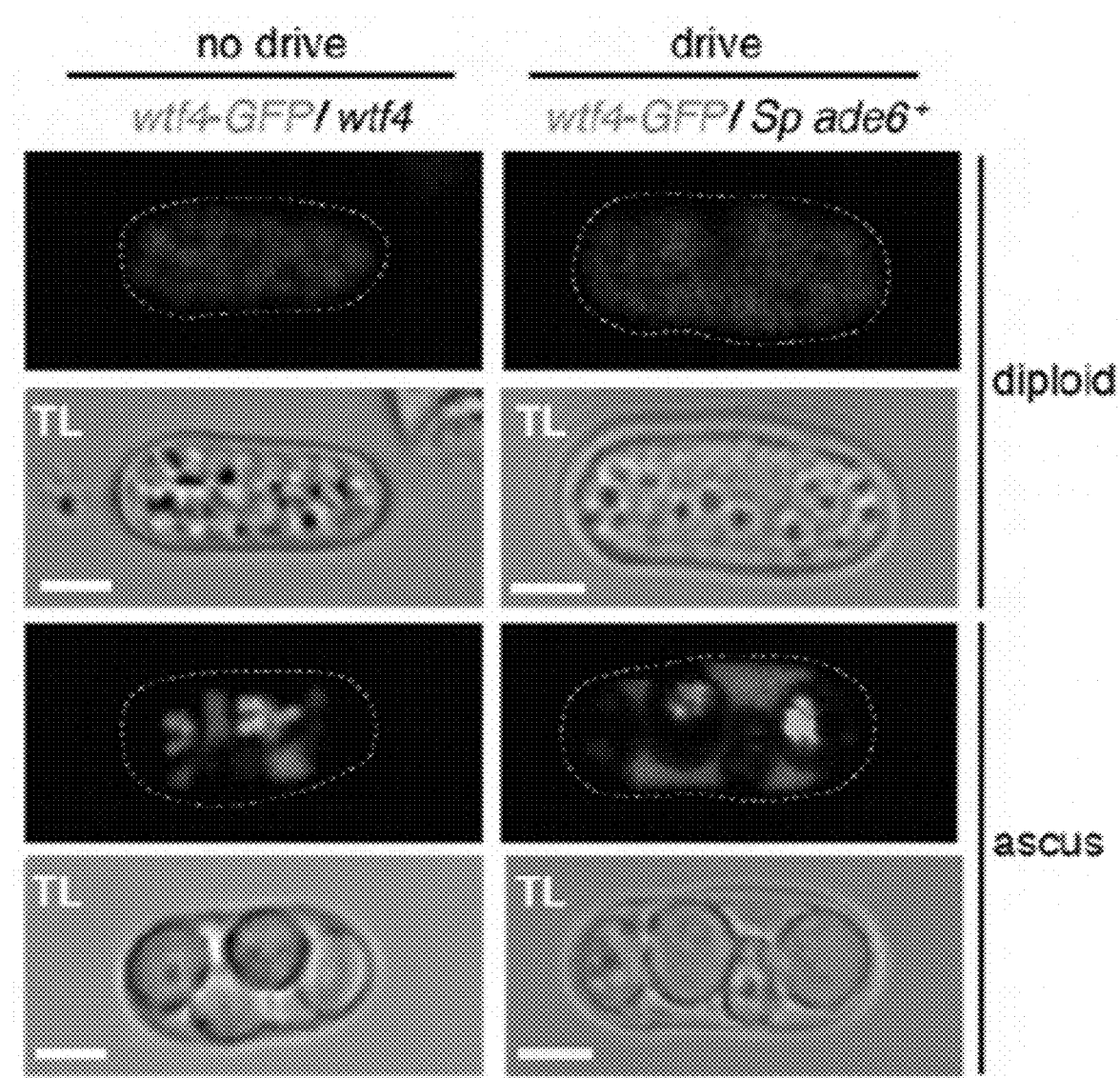
Figure 3D:
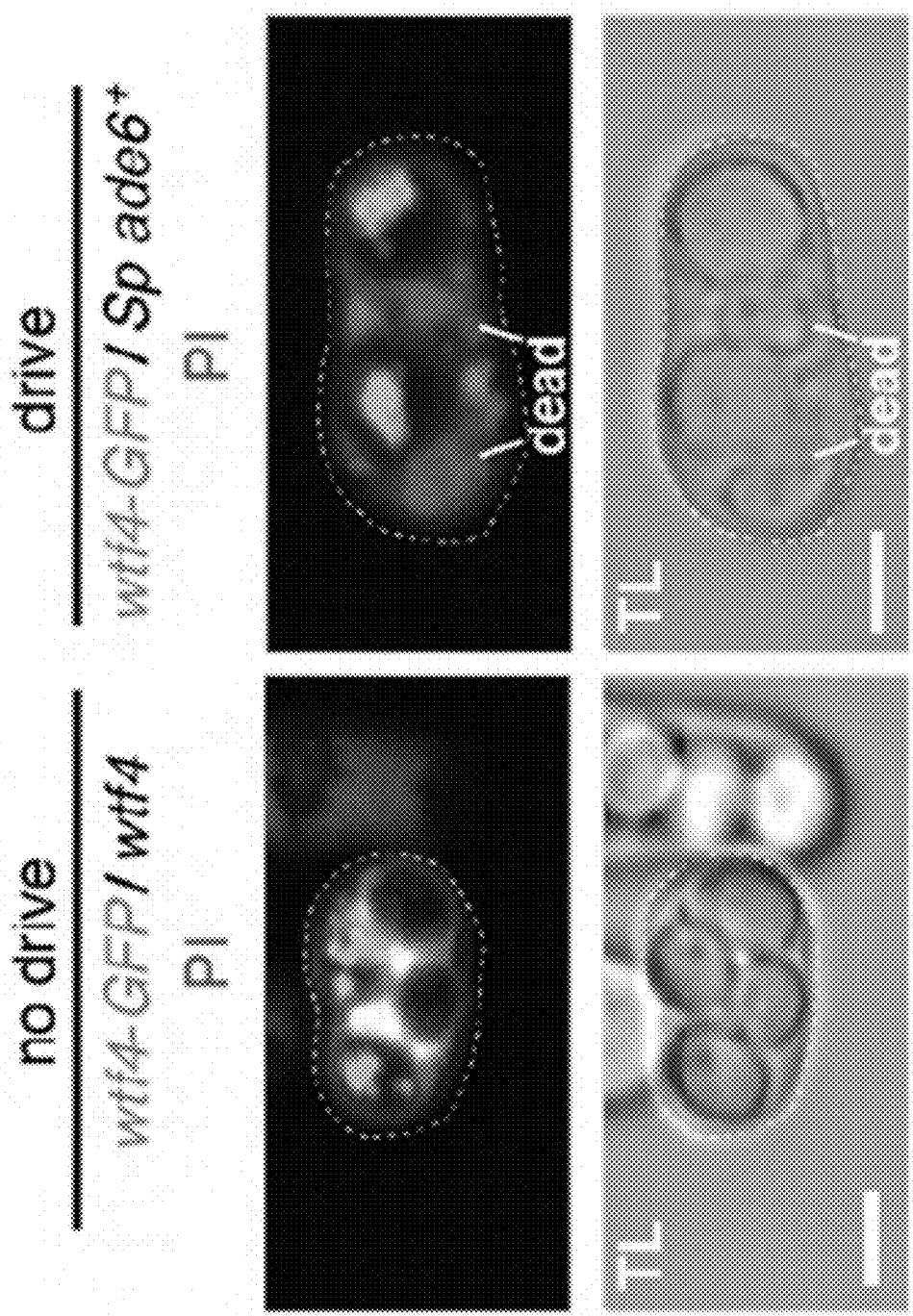
Figure 3E:
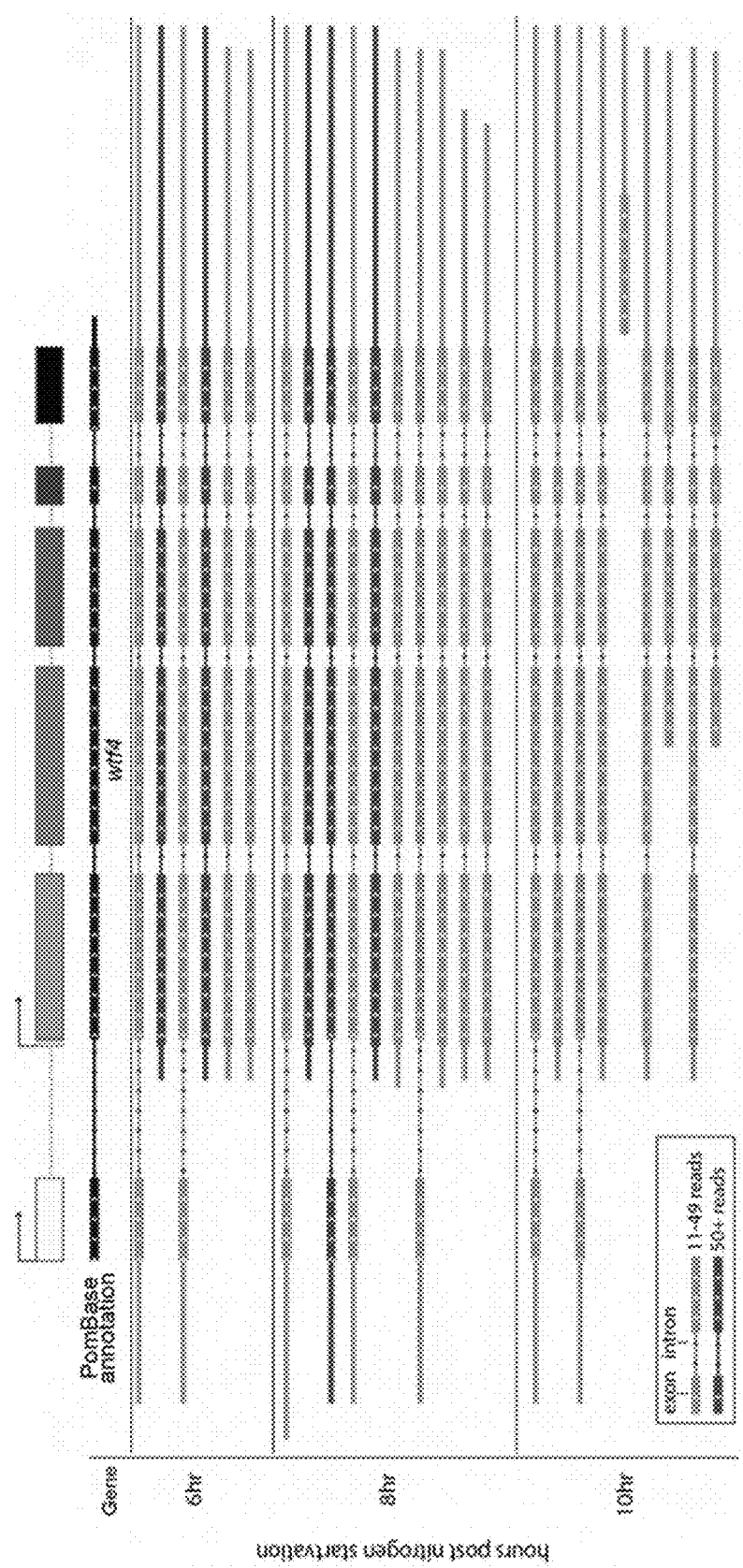
FIG. 3E shows Sp wtf4 has alternate transcriptional start sites. The annotation of the wtf4 gene with alternate start sites predicted is shown at the top in the same format as FIGS. 3-5. The PomBase annotation for Sp wtf4 is shown below that in blue. The transcript locations from one replicate of the meiotic transcript time courses sequenced by Kuang et al. (29) are shown below in red and orange. The IsoSeq consensus reads shown should represent full-length transcripts, and each represents a number of individual sequencing reads. Only transcripts represented by 11 or more reads are displayed. Many of the transcripts vary by only a few nucleotides at the 5' or 3' ends and appear identical in the image. The time the samples were taken after meiotic induction are shown on the left. No transcripts with 11 or more reads were observed at earlier time points. Introns are represented by thin lines with blue arrows and the coding sequences are represented by the thick boxes. There are two major transcriptional start sites and the splice sites of intron 5 are different from those in the PomBase annotation. We did not verify two possible additional transcript types observed only at 10 hrs, or explore their possible functional relevance. The data were visualized using IGV (42).

It was hypothesized that Sk wtf4 encodes two products to achieve drive (FIG. 3A). The first of these is a gamete-killing poison, which acts indiscriminately on all spores. The second product is an antidote that specifically rescues only the gametes encoding Sk wtf4 from the poison. To investigate how Sk wtf4 could make two products, long-read sequence data was analyzed from Sp meiotic mRNAs (29) (See Methods). This revealed that Sp wtf4 is transcribed during meiosis and generates two major overlapping transcripts with different start sites (FIG. 3E). Since the region starting 500 bp upstream of the annotated Sp wtf4 start codon until the putative second start codon is fairly well conserved (98% identical) between Sp and Sk wtf4, it was hypothesized that Sk wtf4 is likely to produce similar alternate isoforms to Sp wtf4. These alternative transcripts of Sk wtf4 could encode the two meiotic drive components—a poison and an antidote (FIG. 3B).

To test the feasibility of this model, the localization of Sk Wtf4-GFP was investigated in Sp diploids induced to undergo meiosis (30). The gene was c-terminally tagged to visualize proteins generated by both the putative Sk wtf4 isoforms; this tag does not interfere with Sk wtf4's ability to function as a drive allele (see data for 'GFP diploid' in FIGS. 6 and 7). Visualizing Sk wtf4-GFP/ade6 heterozygous diploids, there was observed faint cytoplasmic Wtf4-GFP signal before the first meiotic division, which intensified throughout gamete development and filled the ascus surrounding the mature gametes (FIG. 3C). In mature asci, a strong enrichment of Wtf4-GFP was observed within only two of the four spores. The same spore enrichment pattern was observed in Sk wtf4-GFP/Sk wtf4 diploids in which drive does not occur (FIG. 3C).

It was hypothesized that the diffuse Wtf4-GFP localization in the ascus corresponded to the poison whereas the enrichment within the mature spores might reflect the localization of the antidote. If this hypothesis is correct, Wtf4-GFP should be enriched in the two spores that inherit the chromosome carrying Sk wtf4-GFP. Consistent with this idea, it was observed in stained asci from Sk wtf4-GFP/ade6 diploids with PI that the surviving PI-negative spores (95% of which inherit Sk wtf4-GFP) are indeed those with the strong Wtf4-GFP signal (FIG. 3D; FIG. 6). The localization pattern of Wtf4-GFP is consistent with the model of Sk wtf4 encoding two protein isoforms (FIG. 3A).

Figure 4A:
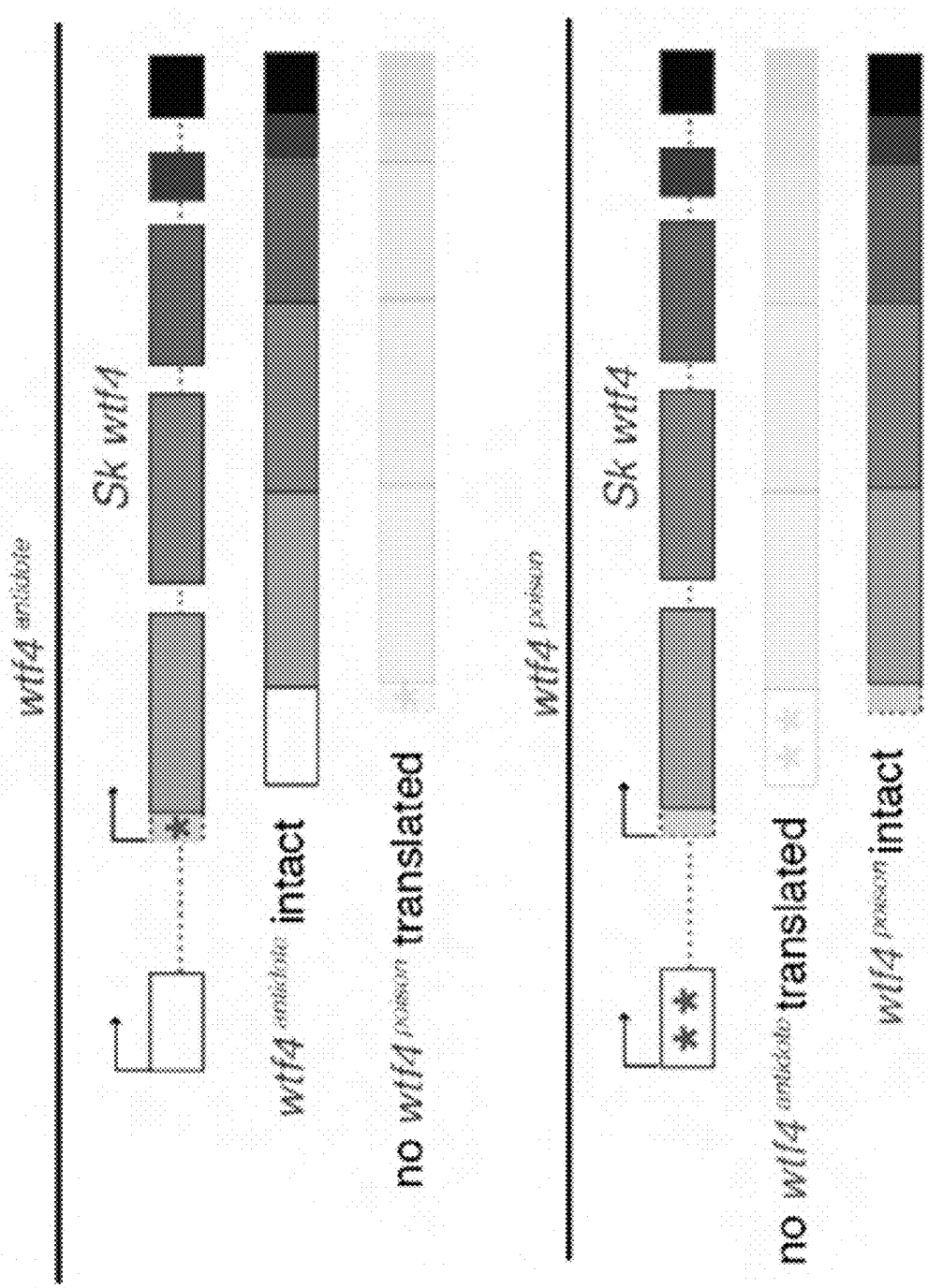

To further test the poison-antidote model, alleles were generated that could produce only the poison or only the antidote. First, the start codon was mutated (ATG to TAC) that is present only in the putative short transcript. The results suggest that this mutant allele retains the antidote function but no longer functions as a poison: this allele is called Sk wtf4$^{antidote}$ (FIG. 4A). In hemizygous diploids (Sk wtf4$^{antidote}$/ade6$^+$), Sk wtf4$^{antidote}$ does not cause spore death (increased frequency of PI-stained spores) or the transmission bias that is observed with the wild-type Sk wtf4 allele, suggesting the mutant can no longer drive (compare FIG. 4B, diploid 20 to FIG. 2A, diploid 17). However, this allele still protects from meiotic drive since Sk wtf4$^+$/Sk wtf4$^{antidote}$ heterozygotes produce PI-excluding spores at the same frequency as wild-type and show unbiased allele transmission (FIG. 4B, diploid 21). These data assign an antidote function to the long transcript.

Next a Sk wtf4$^{poison}$ allele was generated by mutating the two putative start codons (ATG to TAG) found in exon 1 of the long transcript (FIG. 4A). This mutant should be able to generate only the short polypeptide. If this allele retained the ability to poison spores but lost the antidote function, it would be expected that all progeny would be killed in Sk wtf4$^{poison}$/ade6 hemizygotes. Indeed, most spores generated by these diploids die (14% exclude PI-stain, FIG. 4B, diploid 22). Interestingly, the Sk wtf4$^{poison}$ allele was modestly underrepresented (38% transmission) in the few surviving spores generated by diploid 22, indicating that the spores that inherit that allele are especially likely to be destroyed by their own poison (FIG. 4B).

To confirm that the toxicity of the Sk wtf4$^{poison}$ allele was due to its lacking the Sk wtf4$^{antidote}$, Sk wtf4$^{poison}$ Sk wtf4$^+$ heterozygotes were generated. As expected, the spores that inherited the complete Sk wtf4$^+$ gene from these diploids were immune to Sk wtf4$^{poison}$ toxicity, while those that inherit Sk wtf4$^{poison}$ die (FIG. 4B, diploid 23). These results support the model that the short Sk wtf4 transcript encodes a trans-acting gamete poison.

As a final test of the model, the separated poison and antidote mutant alleles were brought back together in one diploid, but on opposite haplotypes. If they function as expected, it is predicted that the Sk wtf4$^{poison}$ spores will die but the spores that inherit the Sk wtf4$^{antidote}$ will survive. This was indeed the case. Only 45% of the spores produced by Sk wtf4$^{antidote}$ Sk wtf4$^{poison}$ heterozygotes can exclude PI stain and 88% of the surviving gametes inherit the Sk wtf4$^{antidote}$ allele (FIG. 4B, diploid 24).

Example 6

The Sk Wtf4 Poison is Trans-Acting, Whereas the Wtf4$^{antidote}$ is Gamete-Specific Next, the localization patterns of the antidote and poison polypeptides were specifically determined. To visualize the antidote peptide, an Sk mCherry$^{antidote}$-wtf4 allele (FIG. 5A) was generated and found to act similarly to the wild-type wtf4 allele (FIG. 5B, diploids 25 and 26) (31). PI staining could not be used to assay fertility of mCherry tagged strains because both signals are red, so viable spore yield assays (VSY) (32) were used to confirm that the fertility of the Sk mCherry$^{antidote}$-wtf4 allele was similar to untagged wtf4 in heterozygotes. Sk mCherry$^{antidote}$-wtf4/ade6 hemizygotes had a VSY of 0.8±0.2 (standard deviation) compared to 1.0±0.4 of Sk wtf4$^+$/ade6, and Sk mCherry$^{antidote}$-wtf4wtf4$^+$ diploids had a VSY of 1.4±0.1 compared to 1.7±0.1 of wild-type.

Figure 5A:
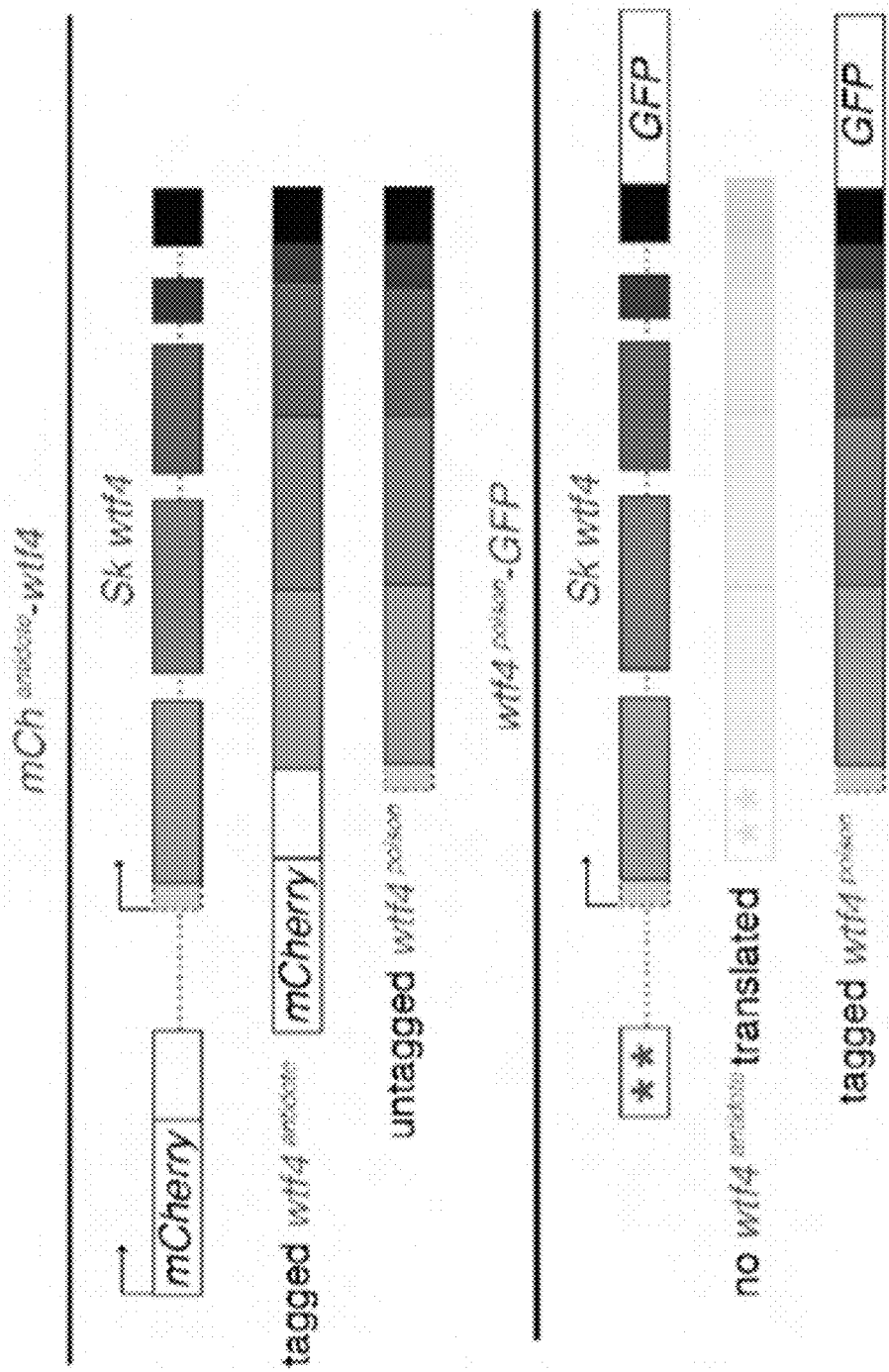
Figure 5C:
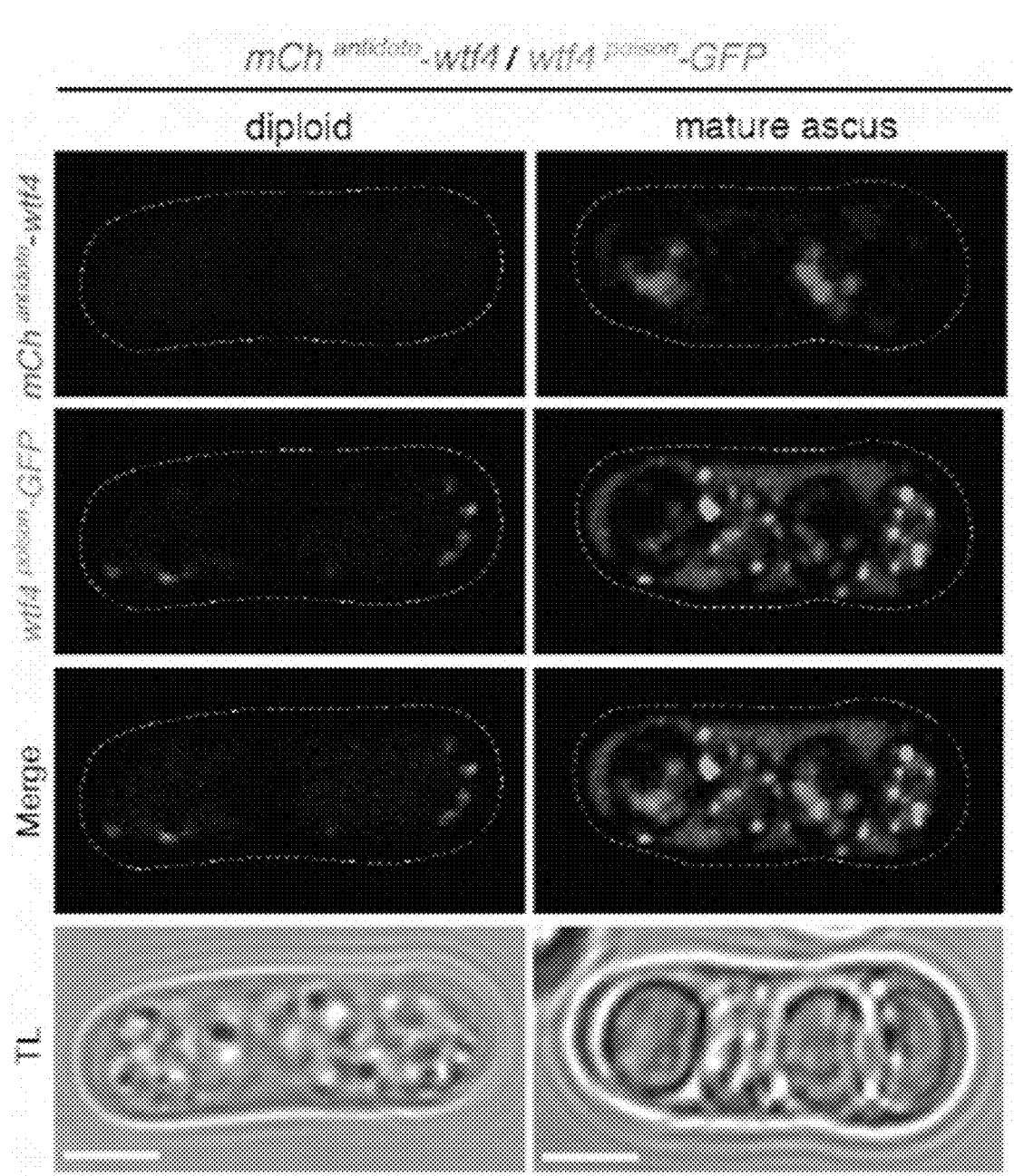
Figure 5D:
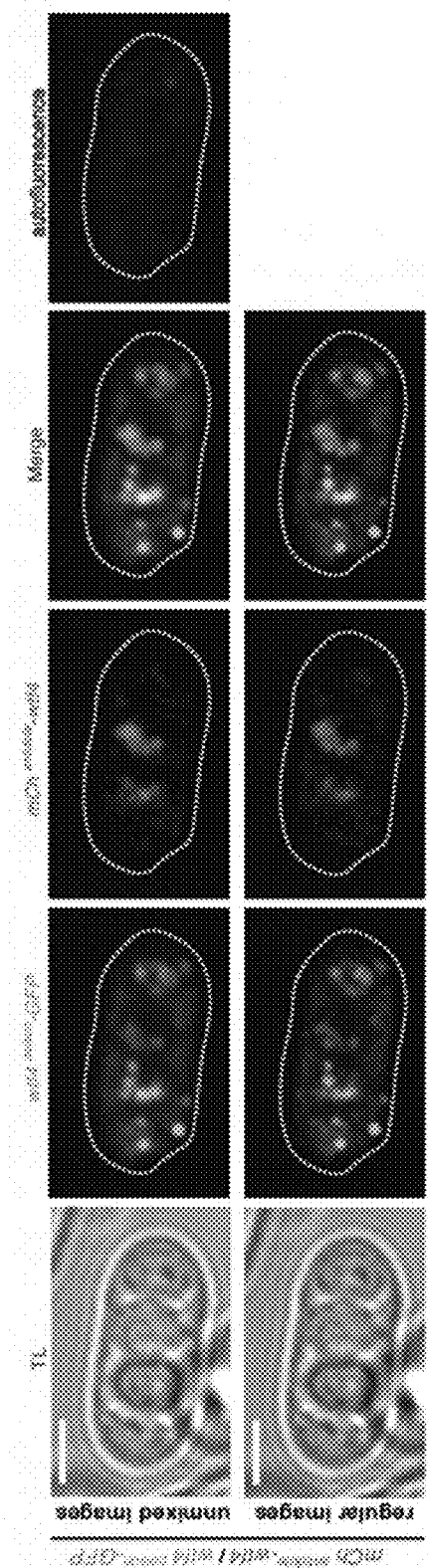

To observe the localization of the poison peptide, a Sk wtf4$^{poison}$-GFP allele was generated (FIG. 5A) (30). While this Sk wtf4$^{poison}$-GFP allele is not as penetrant as the untagged Sk wtf4$^{poison}$ allele, it does have a poison-only phenotype (FIG. 5B, diploids 27 and 28). In Sk mCherry$^{antidote}$-wtf4Sk wtf4$^{poison}$-GFP heterozygotes, Sk wtf4$^{poison}$-GFP expression was observed before the meiotic divisions and later filling mature asci. In contrast, Sk mCherry$^{antidote}$-Wtf4 was observed enriched only in two of the four mature spores (FIG. 5C). Together, these data reconstitute the dual localization patterns observed with Sk Wtf4-GFP and support our model of a poison-antidote system encoded by the same gene (FIG. 3A).

Example 7

Expansion and Rapid Evolution of the Wtf Family is Consistent with a Role in Meiotic Drive It was hypothesized that if Sk wtf4 is not unusual amongst the wtf genes in its ability to drive, meiotic drive could explain the 'driving' force behind the expansion of the wtf gene family (23). The large number of wtfs could also explain the complex drive landscape revealed in our recombination mapping (FIG. 1). To test these ideas, additional wtf genes from Sk were analyzed.

Six Sk wtf genes (wtf2, wtf5, wtf6, wtf28, and wtf21 plus wtf26 together) were cloned and tested for evidence of meiotic drive. As for the tests of Sk wtf4, the above Sk wtf genes were integrated at the ade6 locus of Sp, which disrupted the ade6$^+$ gene. Those haploids were then mated to ade6$^+$ to generate heterozygous diploids and the transmission of the Sk wtf gene(s) into viable progeny was monitored using the heterozygous ade6 markers. Five of the six genes had no observable drive phenotype. Sk wtf2 was transmitted to 47% (n=114) of progeny, Sk wtf5 was transmitted to 44% (n=454), Sk wtf6 was transmitted to 51% (n=471) and the combination of Sk wtf21 and wtf26 (cloned and integrated together) was transmitted to 46% (n=111). However, like Sk wtf4, Sk wtf28 caused strong drive (90% transmission bias and only 57% of spores excluded PI; FIG. 2A, diploid 19).

The sequences of each of these Sk wtfs were also compared to the Sp wtf genes at the syntenic loci. wtf26 and wtf28 are not found in Sp, so have either been lost in Sp, or gained in Sk since divergence. While Sk wtf2 is a 1,036 bp full length gene, Sp wtf2 is likely a 388 bp pseudogene (it has a large deletion relative to other wtf genes and multiple in-frame stop codons). Sk wtf21 is likely a pseudogene (multiple in frame stop codons) whereas Sp wtf21 is intact. The two loci share 83% DNA sequence identity. The wtf5 gene is intact in both species, and the loci share 99% DNA sequence identity and 97% amino acid identity. Sp and Sk wtf6 share 82% nucleotide identity, but only 74% amino acid identity. Altogether, the wtf loci show much greater sequence divergence than the 99.5% genome average identity between Sp and Sk. Such rapid evolution is a hallmark of genes involved in genetic conflicts, such as loci involved in causing or suppressing meiotic drive (25, 26, 33).

Intriguingly, the Sk wtf28 drive gene is also the only one of the six genes tested that also has a putative alternate start codon in exon two that could be used to make a short putative short poison isoform. Additionally, Hu et al. (34) also identified two different wtf drivers in another Sp isolate (CBS5557) and both have a potential alternate start codon in exon 2. Of the 25 wtf loci in Sp, four (wtf4, wtf13, wtf19 and wtf23) also appear to be capable of encoding two proteins and it is predicted that these are active drive genes. In contrast, the intact genes tested that did not confer drive, Sk wtf2, wtf5, wtf6, and wtf26, all encode genes similar to the antidote isoform of Sk wtf4 but appear to lack a shorter poison isoform. Together, the results shown here and those of Hu et al. (34) are consistent with the hypothesis that the ancestral function of the wtf family is to confer meiotic drive.

Example 8

Sk Wtf4 Uses Distinct Transcripts to Encode a Meiotic Drive System

The present disclosure demonstrates that Sk wtf4 is a novel, gamete-killing meiotic drive locus. The present disclosure shows that wtf4 achieves these disparate functions by a previously undescribed mechanism in which the gene encodes a poison protein from one transcriptional start site and an antidote protein from an alternative transcriptional start site. Also shown, is that the poison protein is trans-acting and has the capacity to destroy all gametes, but that the antidote remains in the gametes that inherit the wtf4 locus and specifically rescues them from destruction.

The poison-antidote mechanism of Sk wtf4 is comparable to the bacterial toxin-antitoxin (TA) systems. These systems are found in most prokaryotes and have been extensively studied. TA systems consist of a toxin that will prevent cell growth or viability and an antitoxin that neutralizes the toxin using a wide variety of mechanisms, typically being classified into six different types (35). Interestingly, some toxins are stable, transmembrane proteins that act by disrupting membrane integrity and are counteracted by either an unstable small RNA (35, 36) or a protein that degrades the toxin mRNA (37). In the poison-antidote meiotic drive system disclosed here, Sk wtf4 creates two putative transmembrane proteins: a trans-acting poison and spore-specific antidote. While the exact mechanism of toxicity of Wtf4$^{poison}$ is unknown, it is hypothesize that it could be disrupting membrane integrity in a similar manner to the membrane-lytic toxins of some TA systems (35, 36). In contrast, it is speculated that Wtf4$^{antidote}$ protects the spores that inherited Sk wtf4 by sequestering the poison for degradation. The spore specificity of Wtf4$^{antidote}$ could be due to late translation or a spore retention signal within exon 1, because that is the only region that Wtf4$^{poison}$ is lacking. In addition, work by Hu et al. suggests that the C-termini of Wtf proteins may be more important for the poison than for the antidote functions, despite both proteins being generated by a single given wtf gene sharing a common C-terminus (34).

Outside of its role in meiotic drive, wtf4 has no apparent role in promoting fertility (FIG. 2A, diploid 15). Instead, the gene causes about half of all gametes to be destroyed in heterozygotes. In other words, the wild-type allele of wtf4 causes infertility to promote its own fitness. This puts wtf4 into a state of genetic conflict with the rest of the genome because infertility is clearly bad for fitness of loci unlinked to wtf4. Unlinked variants that can suppress drive would be favored by natural selection because they increase fitness (7). Novel wtf4 variants that can evade this suppression to reestablish drive would then be favored. This evolutionary dynamic is analogous to that observed between viruses and host immune systems and is well known to foster a 'molecular arms race' in which both sides must continually innovate (25, 26). Consistent with the idea that the gene is locked in such an arms race, the DNA sequence divergence between Sk and Sp at the wtf4 locus is more than 20-fold higher than the genome-wide average (17, 18).

The evolution of wtf4 elicits the question of how the gene can rapidly evolve while maintaining specificity between the poison and antidote it encodes. Uncoupling these components leads to sterility, an evolutionary dead-end. It is possible that such variants do arise and are quickly purged from populations. The present disclosure provides that the coding sequence overlap between the poison and antidote could promote specificity between the two components, e.g., by the antidote acting as a dominant suppressor of the poison. In this manner, the poison could diverge without losing the self-protection conferred by the antidote. Using a shared sequence to confer specificity between drive components may be a recurring theme amongst gamete-killers.

The present disclosure provides that the varied phenotypes of our Sp chromosome 3 introgressions reveal a complex landscape of meiotic drive loci in the Sk and Sp genomes (15). As Sk wtf4 is a member of the large wtf gene family, the most likely candidates underlying these drive phenotypes are wtf genes. Consistent with the idea that the Sk wtf4 drive phenotype is not unique, it is shown that Sk wtf28 can also cause drive.

Although not all wtfs are capable of autonomously causing meiotic drive, their rapid evolution is still consistent with their involvement in meiotic drive (23). The present disclosure provides that different wtf genes represent distinct evolutionary stages. The putative ancestral type (Sk wtf4 and wtf28) are still active as meiotic drivers and encode both poison and antidote proteins. The next stratum represent genes (Sk wtf2, wtf5, wtf6 and wtf26) that have lost poison, but not antidote function. As shown for the Sk wtf4$^{antidote}$ allele, such alleles are unlikely to cause meiotic drive as they have lost their poison-coding capacity, but they still have protective function against the ancestral drive allele and thus may have been selectively retained as 'domesticated parasites.' Over time, when the protective function is no longer beneficial and selected for (e.g., if the ancestral drive allele is lost from the population), such antidote genes may also eventually degenerate. Therefore, the final stratum represents putative wtf pseudogenes such as Sk wtf21, in which both the poison and antidote function have decayed.

There are 25 wtf loci in the Sp genome and the present disclosure provides that these genes cause and or modify meiotic drive (23, 24). Meiotic drive has therefore played a significant role in the evolution of the Sp group of fission yeasts, in despite the heavy fitness costs these selfish loci can levy.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes can be made by those skilled in the art without departing from the spirit of this disclosure. Those skilled in the art will appreciate that the inventive principles can be practiced in other than the described embodiments, which are presented for purposes of illustration and not limitation.

CITED DOCUMENTS

The following documents, to the extent they provide exemplary procedural or other details supplementary to those set forth herein, are specifically incorporated herein by reference.
1. M. E. Thoma et al., Prevalence of infertility in the United States as estimated by the current duration approach and a traditional constructed approach. Fertil Steril 99, 1324-31 e1321 (2013).
2. L. Segurel, E. M. Leffler, M. Przeworski, The case of the fickle fingers: how the PRDM9 zinc finger protein specifies meiotic recombination hotspots in humans. PLoS Biol 9, e1001211 (2011).
3. D. C. Presgraves, The molecular evolutionary basis of species formation. Nat Rev Genet 11, 175-80 (2010).
4. N. A. Johnson, Hybrid incompatibility genes: remnants of a genomic battlefield? Trends Genet 26, 317-25 (2010).
5. A. K. Lindholm et al., The Ecology and Evolutionary Dynamics of Meiotic Drive. Trends Ecol Evol 31, 315-26 (2016).
6. L. Sandler, E. Novitski, Meiotic Drive as an Evolutionary Force. The American Naturalist 91, 105-110 (1957).
7. J. F. Crow, Why is Mendelian segregation so exact? Bioessays 31, 305-12 (1991).
8. J. P. Didion et al., A multi-megabase copy number gain causes maternal transmission ratio distortion on mouse chromosome 2. PLoS Genet 11, e1004850 (2015).
9. C. S. Ottolini et al., Genome-wide maps of recombination and chromosome segregation in human oocytes and embryos show selection for maternal recombination rates. Nat Genet 47, 727-35 (2015).
10. P. Grognet et al., Genes that bias Mendelian segregation. PLoS Genet 10, e1004387 (2014).
11. A. Burt, R. Trivers, Genes in conflict: the biology of selfish genetic elements. (Belknap Press of Harvard University Press, Cambridge, Mass., 2006), pp. viii, 602 p., 608 p. of plates.
12. A. M. Larracuente, D. C. Presgraves, The selfish Segregation Distorter gene complex of Drosophila melanogaster. Genetics 192, 33-53 (2012).
13. H. Bauer et al., The nucleoside diphosphate kinase gene Nme3 acts as quantitative trait locus promoting non-Mendelian inheritance. PLoS Genet 8, e1002567 (2012).
14. H. Bauer, N. Veron, J. Willert, B. G. Herrmann, The t-complex-encoded guanine nucleotide exchange factor Fgd2 reveals that two opposing signaling pathways promote transmission ratio distortion in the mouse. Genes Dev 21, 143-147 (2007).
15. H. Bauer, J. Willert, B. Koschorz, B. G. Herrmann, The t complex-encoded GTPase-activating protein Tagap1 acts as a transmission ratio distorter in mice. Nat Genet 37, 969-973 (2005).
16. T. M. Hammond, D. G. Rehard, H. Xiao, P. K. Shiu, Molecular dissection of Neurospora Spore killer meiotic drive elements. Proc Natl Acad Sci USA 109, 12093-12098 (2012).
17. N. Rhind et al., Comparative functional genomics of the fission yeasts. Science 332, 930-936 (2011).
18. S. E. Zanders et al., Genome rearrangements and pervasive meiotic drive cause hybrid infertility in fission yeast. Elife 3, e02630 (2014).
19. A. T. Avelar, L. Perfeito, I. Gordo, M. G. Ferreira, Genome architecture is a selectable trait that can be maintained by antagonistic pleiotropy. Nat Commun 4, 2235 (2013).
20. N. Phadnis, R. W. Hyppa, G. R. Smith, New and old ways to control meiotic recombination. Trends Genet 27, 411-421 (2011).
21. K. Bomblies, Cheaters divide and conquer. Elife 3, e03371 (2014).
22. A. Moore, C. J. Donahue, K. D. Bauer, J. P. Mather, Simultaneous measurement of cell cycle and apoptotic cell death. Methods Cell Biol 57, 265-278 (1998).
23. N. J. Bowen, I. K. Jordan, J. A. Epstein, V. Wood, H. L. Levin, Retrotransposons and their recognition of pol II promoters: a comprehensive survey of the transposable elements from the complete genome sequence of Schizosaccharomyces pombe. Genome Res 13, 1984-1997 (2003).
24. J. Mata, R. Lyne, G. Burns, J. Bahler, The transcriptional program of meiosis and sporulation in fission yeast. Nat Genet 32, 143-147 (2002).
25. M. D. Daugherty, H. S. Malik, Rules of engagement: molecular insights from host-virus arms races. Annu Rev Genet 46, 677-700 (2012).
26. R. N. McLaughlin, Jr., H. S. Malik, Genetic conflicts: the usual suspects and beyond. J Exp Biol 220, 6-17 (2017).

27. C. I. Wu, T. W. Lyttle, M. L. Wu, G. F. Lin, Association between a satellite DNA sequence and the Responder of Segregation Distorter in *D. melanogaster*. Cell 54, 179-189 (1988).
28. A. M. Harvey et al., A critical component of meiotic drive in *Neurospora* is located near a chromosome rearrangement. Genetics 197, 1165-1174 (2014).
29. Z. Kuang, J. D. Boeke, S. Canzar, The dynamic landscape of fission yeast meiosis alternative-splice isoforms. Genome Res (2016).
30. M. A. Sheff, K. S. Thom, Optimized cassettes for fluorescent protein tagging in *Saccharomyces cerevisiae*. Yeast 21, 661-670 (2004).
31. D. W. Hailey, T. N. Davis, E. G. Muller, Fluorescence resonance energy transfer using color variants of green fluorescent protein. Methods Enzymol 351, 34-49 (2002).
32. G. R. Smith, Genetic analysis of meiotic recombination in *Schizosaccharomyces pombe*. Methods Mol Biol 557, 65-76 (2009).
33. S. Henikoff, K. Ahmad, H. S. Malik, The centromere paradox: stable inheritance with rapidly evolving DNA. Science 293, 1098-1102 (2001).
34. W. Hu et al., A large gene family in fission yeast encodes spore killers that subvert Mendel's law Submitted.
35. K. Y. Lee, B. J. Lee, Structure, Biology, and Therapeutic Application of Toxin-Antitoxin Systems in Pathogenic Bacteria. Toxins (Basel) 8, (2016).
36. S. J. Unterholzner, B. Poppenberger, W. Rozhon, Toxin-antitoxin systems: Biology, identification, and application. Mob Genet Elements 3, e26219 (2013).
37. X. Wang et al., A new type V toxin-antitoxin system where mRNA for toxin GhoT is cleaved by antitoxin GhoS. Nat Chem Biol 8, 855-61 (2012).
38. L. C. De Veaux, N. A. Hoagland, G. R. Smith, Seventeen complementation groups of mutations decreasing meiotic recombination in *Schizosaccharomyces pombe*. Genetics 130, 251-262 (1992).
39. A. L. Goldstein, J. H. McCusker, Three new dominant drug resistance cassettes for gene disruption in *Saccharomyces cerevisiae*. Yeast 15, 1541-1553 (1999).
40. A. Wach, A. Brachat, R. Pohlmann, P. Philippsen, New heterologous modules for classical or PCR-based gene disruptions in *Saccharomyces cerevisiae*. Yeast 10, 1793-1808 (1994).
41. T. D. Wu et al., GMAP and GSNAP for Genomic Sequence Alignment: Enhancements to Speed, Accuracy, and Functionality. Methods Mol Biol 1418, 283-334 (2016).
42. H. Thorvaldsdottir, J. T. Robinson, J. P. Mesirov, Integrative Genomics Viewer (IGV): high-performance genomics data visualization and exploration. Brief Bioinform 14, 178-92 (2013).
43. A. Krogh, B. Larsson, G. von Heijne, E. L. Sonnhammer, Predicting transmembrane protein topology with a hidden Markov model: application to complete genomes. J Mol Biol 305, 567-580 (2001).
44. J. Z. Jacobs, K. M. Ciccaglione, V. Tournier, M. Zaratiegui, Implementation of the CRISPR-Cas9 system in fission yeast. Nat Commun 5, 5344 (2014).
45. J. A. Young et al., Meiotic recombination remote from prominent DNA break sites in *S. pombe*. Mol Cell 9, 253-63 (2002).

What is claimed is:

1. A meiotic drive composition comprising:
a recombinant DNA sequence encoding a first peptide sequence and a second peptide sequence, the first peptide sequence capable of destroying a gamete and the second peptide sequence capable of rescuing a gamete from the first peptide sequence;
wherein the first peptide sequence is SEQ ID NO: 3;
wherein the second peptide sequence is SEQ ID NO: 4;
wherein the recombinant DNA sequence comprises a heterologous regulatory sequence;
wherein the first peptide sequence is transported outside of a cell and the second peptide sequence is not transported outside of a cell
wherein the first peptide sequence and the second peptide sequence are derived from alternative transcriptional start sites on the recombinant DNA sequence; and
wherein the recombinant DNA sequence, when expressed in a diploid organism, is effective to bias offspring toward having the recombinant DNA.

2. The meiotic drive composition of claim 1, wherein the recombinant DNA sequence does not naturally occur in the diploid organism.

3. The meiotic drive composition of claim 1, wherein the recombinant DNA sequence is adapted to integrate into the genome of the diploid organism.

4. A vector comprising the recombinant DNA sequence according to claim 1, and a heterologous DNA sequence.

5. A meiotic drive composition comprising:
a recombinant DNA sequence encoding a first peptide sequence and a second peptide sequence, the first peptide sequence capable of destroying a gamete and the second peptide sequence capable of rescuing a gamete from the first peptide sequence;
wherein the first peptide sequence is SEQ ID NO: 3;
wherein the second peptide sequence is SEQ ID NO: 4;
wherein the recombinant DNA sequence comprises a heterologous regulatory sequence;
wherein the first peptide sequence is transported outside of a cell and the second peptide sequence is not transported outside of a cell; and
wherein the recombinant DNA sequence, when expressed in a diploid organism, is effective to bias offspring toward having the recombinant DNA.

6. A meiotic drive composition comprising:
a recombinant DNA sequence encoding a first peptide sequence and a second peptide sequence, the first peptide sequence capable of destroying a gamete and the second peptide sequence capable of rescuing a gamete from the first peptide sequence;
wherein the first peptide sequence is SEQ ID NO: 3;
wherein the second peptide sequence is SEQ ID NO: 4;
wherein the recombinant DNA sequence comprises a heterologous regulatory sequence;
wherein the first peptide sequence and the second peptide sequence are derived from alternative transcriptional start sites on the recombinant DNA sequence; and
wherein the recombinant DNA sequence, when expressed in a diploid organism, is effective to bias offspring toward having the recombinant DNA.

* * * * *